United States Patent
Liu et al.

(10) Patent No.: US 11,718,610 B2
(45) Date of Patent: Aug. 8, 2023

(54) COMPOUNDS CONTAINING BENZOSULTAM

(71) Applicant: MEDSHINE DISCOVERY INC., Nanjing (CN)

(72) Inventors: Xile Liu, Shanghai (CN); Charles Z. Ding, Shanghai (CN); Shuhui Chen, Shanghai (CN); Lihong Hu, Shanghai (CN); Haiwen Wan, Shanghai (CN); Xiu Jiang, Shanghai (CN)

(73) Assignee: MEDSHINE DISCOVERY INC., Nanjing (CN)

( * ) Notice: Subject to any disclaimer, the term of this patent is extended or adjusted under 35 U.S.C. 154(b) by 0 days.

(21) Appl. No.: 17/922,195

(22) PCT Filed: Apr. 26, 2021

(86) PCT No.: PCT/CN2021/089889
§ 371 (c)(1),
(2) Date: Oct. 28, 2022

(87) PCT Pub. No.: WO2021/218912
PCT Pub. Date: Nov. 4, 2021

(65) Prior Publication Data
US 2023/0183230 A1      Jun. 15, 2023

(30) Foreign Application Priority Data

Apr. 30, 2020  (CN) .......................... 202010363156.1
Feb. 2, 2021   (CN) .......................... 202110145140.8

(51) Int. Cl.
*C07D 417/14*   (2006.01)
*A61P 35/00*    (2006.01)

(52) U.S. Cl.
CPC ............ *C07D 417/14* (2013.01); *A61P 35/00* (2018.01); *C07B 2200/05* (2013.01)

(58) Field of Classification Search
CPC .............................. C07D 417/14; A61P 35/00
See application file for complete search history.

(56) References Cited

U.S. PATENT DOCUMENTS

| | | |
|---|---|---|
| 4,263,393 A | 4/1981 | Chen |
| 2009/0298815 A1 | 12/2009 | Adams et al. |
| 2015/0274733 A1 | 10/2015 | Dillon |
| 2019/0047990 A1 | 2/2019 | Berdini et al. |

FOREIGN PATENT DOCUMENTS

| | | | |
|---|---|---|---|
| CN | 107635990 A | 1/2018 | |
| CN | 108617166 * | 2/2018 | .......... C07D 401/14 |
| CN | 108617166 A | 10/2018 | |
| CN | 110831939 A | 2/2020 | |
| JP | 2011519940 A | 7/2011 | |
| JP | 2015529248 A | 10/2015 | |
| JP | 2018532737 A | 11/2018 | |
| WO | 9941246 A1 | 8/1999 | |
| WO | 2015140717 A1 | 9/2015 | |
| WO | 2016147144 A1 | 9/2016 | |
| WO | 2018193410 A1 | 10/2018 | |
| WO | 2020107987 A1 | 6/2020 | |

OTHER PUBLICATIONS

International Search Report issued in International Patent Application No. PCT/CN2021/089889, dated Jul. 20, 2021.
Written Opinion issued in International Patent Application No. PCT/CN2021/089889, dated Jul. 20, 2021.
First Office Action issued in Canadian Patent Application No. 3,177,298, dated Jan. 24, 2023, 4 pages.
First Office Action issued in Korean Patent Application No. 10-2022-7041520, dated Apr. 3, 2023, 6 pages.
First Office Action issued in Japanese Patent Application No. 2022-566606, dated Apr. 7, 2023, 3 pages.

* cited by examiner

*Primary Examiner* — Erich A Leeser
(74) *Attorney, Agent, or Firm* — Dilworth IP, LLC

(57) ABSTRACT

Disclosed is a class of compounds containing arylsultam, and specifically disclosed are a compound represented by formula (II), and a pharmaceutically acceptable salt or an isomer thereof.

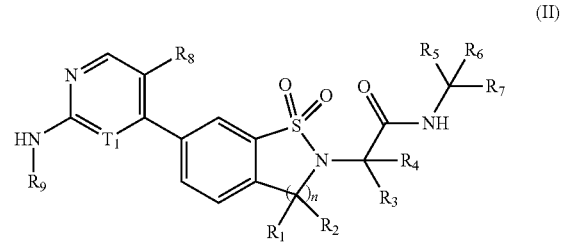

20 Claims, 1 Drawing Sheet

COMPOUNDS CONTAINING BENZOSULTAM

The present application claims the right of the priorities of Chinese patent application CN202010363156.1 filed on Apr. 30, 2020 and Chinese patent application CN202110145140.8 filed on Feb. 2, 2021. The contents of the above Chinese patent application are incorporated herein by reference in their entireties.

FIELD OF THE INVENTION

The present disclosure relates to a class of compounds containing benzosultam, and specifically relates to a compound represented by formula (ID), a pharmaceutically acceptable salt thereof or an isomer thereof.

BACKGROUND OF THE INVENTION

The mitogen-activated protein kinases (MAPK) pathway exists in a series of cellular processes such as cell proliferation, differentiation, apoptosis and stress response. Among them, the RAS-RAF-MEK-ERK pathway is one of the most widely known MAPK pathways. In this pathway, extracellular growth factors (PDGF or EGF) are combined with transmembrane receptors (EGFR or PDGFR, etc.) to activate the receptors, and binding and activation of RAS proteins in the membranes and GTP are made by the activated receptors through guanine nucleotide exchange factor (SOS); and the activated RAS further indirectly phosphorylates RAF; the activated RAF is phosphorylated on two serine residues of MEK1%2; the activated MEK1/2 in turn activates its downstream substrate ERK1/2; and then after dimerization, phosphorylated ERK1/2 moves into the cell nucleus and accumulates. ERK in the cell nucleus involves many cellular functions, including nuclear transport, signal transduction, DNA repairing, mRNA processing and translation, etc. If the genes involved in this pathway are mutated, or the growth factors, downstream signal proteins or protein kinases are over-expressed, it will lead to the continuous activation of the cell pathway, uncontrolled cell proliferation and eventually lead to tumor formation. For example, about 30% of human cancer cells belong to RAS mutation, wherein KRAS mutation is the most common subtype of RAS mutation, and KRAS mutated tumors account for about 22% of all human tumor cells, wherein 70-90% of pancreatic cancer, 10-20% of non-small cell lung cancer and 25-35% of colorectal cancer belong to KRAS mutation; and about 8% tumors belong to BRAF mutation, wherein 50-60% melanoma and 40-60% papillary thyroid cancer and the like all belong to BRAF mutation.

Extracellular signal-regulated kinase (ERK1/2) is an important member of MAPK family, and as the "final manager" downstream of RAF/RAF/MEK/ERK pathway, targeted inhibition of ERK1/2 is expected to be used for the treatment of cancer caused by abnormal activation of MAPK pathway (activation variation of RAF/RAF/MEK, etc.), and may also be effective for patients who are resistant to RAF or MEK inhibitors due to reactivation of ERK1/2. According to many preclinical reports, MAPK pathway inhibitors can effectively inhibit cancer cells with BRAF and RAS mutations, and for example, BRAF inhibitors Vemurafenib. Dabrafenib and MEK inhibitor Trametinib have been approved for the treatment of melanoma with BRAF mutations. However, these medicaments still have drug resistance problems. The resistance mechanism of BRA inhibitor has been confirmed, wherein, including MEK trans-activation of CRAF and RTK, up-regulation of NRAS signal, and MEK activation mutation: and the drug resistance mechanism of MEK inhibitors includes MEK mutation to reduce its binding to medicaments or enhance the activity of MEK itself, and BRAF or KRAS amplification and the like. Both RAF inhibitor resistance and MEK inhibitor resistance will reactivate the RAS-RAF-MEK-ERK pathway and lead to the continuous amplification of cancer cells. Therefore, the development of a new type of dual-mechanism ERK inhibitor will be effective not only for patients with MAPK signaling pathway mutation, but also for patients with BRAF and MEK inhibitors resistance.

SUMMARY OF THE INVENTION

The present disclosure provides a compound represented by formula (II) or a pharmaceutically acceptable salt thereof,

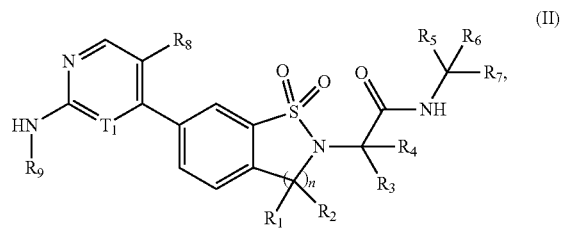

wherein,
$T_1$ is CH or N;
n is 1 or 2;
$R^1$ and $R^2$ are each independently H, D, F, Cl or $C_{1-3}$ alkyl, wherein the $C_{1-3}$ alkyl is optionally substituted by 1, 2 or 3 substituents independently selected from F, Cl, Br and I;
or $R_1$ and $R_2$ combining with the carbon atoms to which they are attached form

$R_3$ and $R_4$ are each independently H or $C_{1-3}$ alkyl, wherein the $C_{1-3}$ alkyl is optionally substituted by 1, 2 or 3 substituents independently selected from F, Cl, Br, I and —OH;
$R_5$ and $R_6$ are each independently H or $C_{1-3}$ alkyl, wherein the $C_{1-3}$ alkyl is optionally substituted by 1, 2 or 3 substituents independently selected from F, Cl, Br, I, —OH and —OCH$_3$;
$R_7$ is phenyl or pyridyl, wherein the phenyl and pyridyl are optionally substituted by 1, 2, 3 or 4 $R_a$;
$R_8$ is H, F, Cl or Br;
$R_9$ is tetrahydro-2H-pyranyl, wherein the tetrahydro-2H-pyranyl is optionally substituted by 1, 2, 3 or 4 $R_b$;
$R_a$ is each independently F, Cl, Br, I, $C_{1-3}$ alkyl, $C_{1-3}$ alkoxy, NH—$C_{1-3}$ alkyl or N—($C_{1-3}$ alkyl)$_2$, wherein the $C_{1-3}$ alkyl, $C_{1-3}$ alkoxy, —NH—$C_{1-3}$ alkyl and —N—($C_{1-3}$ alkyl)$_2$ are each independently and optionally substituted by 1, 2 or 3 substituents independently selected from F, Cl, Br, I and —OH;
$R_b$ is each independently F, Cl, Br, I, D or $C_{1-3}$ alkyl, wherein the $C_{1-3}$ alkyl is optionally substituted by 1, 2 or 3 substituents independently selected from F, Cl, Br, I and —OH.

The present disclosure also provides a compound represented by formula (II) or a pharmaceutically acceptable salt thereof,

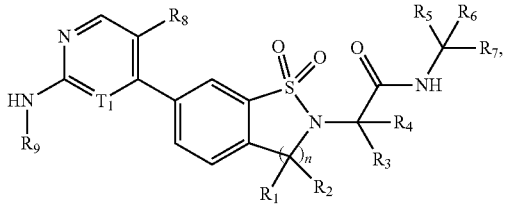

wherein, $T_1$ is CH or N;

n is 1 or 2;

$R_1$ and $R_2$ are each independently H, F, Cl or $C_{1-3}$ alkyl, wherein the $C_{1-3}$ alkyl is optionally substituted by 1, 2 or 3 substituents independently selected from F, Cl, Br and I;

or $R_1$ and $R_2$ combining with the carbon atoms to which they are attached form

$R_3$ and $R_4$ are each independently H or $C_{1-3}$ alkyl, wherein the $C_{1-3}$ alkyl is optionally substituted by 1, 2 or 3 substituents independently selected from F, Cl, Br, I and —OH;

$R_5$ and $R_6$ are each independently H or $C_{1-3}$ alkyl, wherein the $C_{1-3}$ alkyl is optionally substituted by 1, 2 or 3 substituents independently selected from F, Cl, Br, I, —OH and —OCH$_3$;

$R_7$ is phenyl or pyridyl, wherein the phenyl and pyridyl are optionally substituted by 1, 2, 3 or 4 $R_a$;

$R_8$ is H, F, Cl or Br;

$R_9$ is tetrahydro-2H-pyranyl, wherein the tetrahydro-2H-pyranyl is optionally substituted by 1, 2, 3 or 4 $R_b$;

$R_a$ is each independently F, Cl, Br, I, $C_{1-3}$ alkyl, $C_{1-3}$ alkoxy, NH—$C_{1-3}$ alkyl or N—($C_{1-3}$ alkyl)$_2$, wherein the $C_{1-3}$ alkyl, $C_{1-3}$ alkoxy, —NH—$C_{1-3}$ alkyl and —N—($C_{1-3}$ alkyl)$_2$ are each independently and optionally substituted by 1, 2 or 3 substituents independently selected from F, Cl, Br, I and —OH;

$R_b$ is each independently F, Cl, Br, I, D or $C_{1-3}$ alkyl, wherein the $C_{1-3}$ alkyl is optionally substituted by 1, 2 or 3 substituents independently selected from F, Cl, Br, I and —OH.

The present disclosure also provides a compound represented by formula (I) or a pharmaceutically acceptable salt thereof,

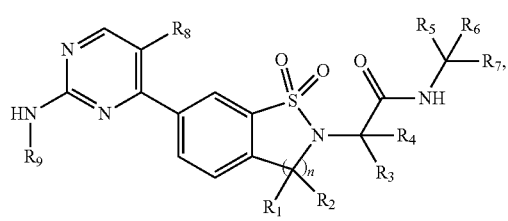

wherein, n is 1 or 2;

$R_1$ and $R_2$ are each independently H, F, Cl or $C_{1-3}$ alkyl, wherein the $C_{1-3}$ alkyl is optionally substituted by 1, 2 or 3 substituents independently selected from F, Cl, Br and I;

or $R^1$ and $R_2$ combining with the carbon atoms to which they are attached form

$R_3$ and $R_4$ are each independently H or $C_{1-3}$ alkyl, wherein the $C_{1-3}$ alkyl is optionally substituted by 1, 2 or 3 substituents independently selected from F, Cl, Br and I;

$R_5$ and $R_6$ are each independently H or $C_{1-3}$ alkyl, wherein the $C_{1-3}$ alkyl is optionally substituted by 1, 2 or 3 substituents independently selected from F, Cl, Br, I, —OH and —OCH$_3$;

$R_7$ is phenyl, wherein the phenyl is optionally substituted by 1, 2, 3 or 4 $R_a$;

$R_8$ is H, F or Cl;

$R_9$ is tetrahydro-2H-pyranyl, wherein the tetrahydro-2M-pyranyl is optionally substituted by 1, 2, 3 or 4 $R_b$;

$R_a$ is each independently F, Cl, Br, I, $C_{1-3}$ alkyl or $C_{1-3}$ alkoxy, wherein the $C_{1-3}$ alkyl and $C_{1-3}$ alkoxy are optionally substituted by 1, 2 or 3 substituents independently selected from F, Cl, Br, I and —OH;

$R_b$ is each independently F, Cl, Br, I or $C_{1-3}$ alkyl, wherein the $C_{1-3}$ alkyl is optionally substituted by 1, 2 or 3 substituents independently selected from F, Cl, Br, I and —OH.

In some embodiments of the present disclosure, the compound has the structure represented by formula (I-1) or (I-2):

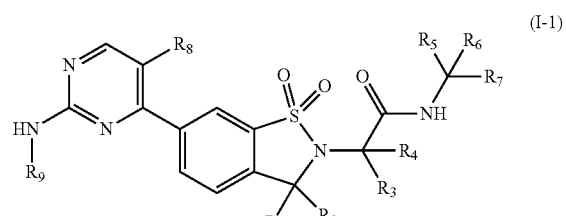

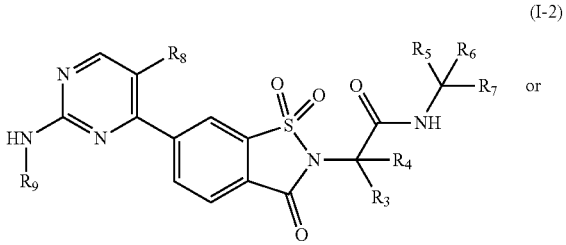

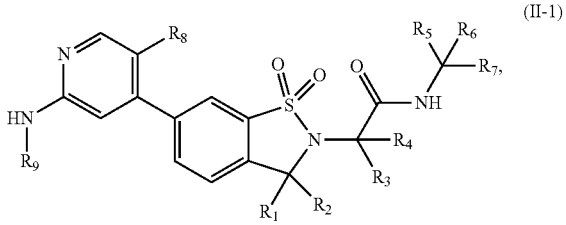

wherein, $R_1$, $R_2$, $R_3$, $R_4$, $R_5$, $R_6$, $R_7$, $R_8$ and $R_9$ are as defined herein.

In some embodiments of the present disclosure, the $R_b$ is each independently F, Cl, Br, I, D or —CH$_3$, and the other variables are as defined herein.

In some embodiments of the present disclosure, the $R_b$ is each independently F, Cl, Br, I or —CH$_3$, and the other variables are as defined herein.

In some embodiments of the present disclosure, the $R_9$ is wherein the is optionally substituted by 1, 2 or 3 $R_b$, and $R_b$ and the other variables are as defined herein.

In some embodiments of the present disclosure, the $R_9$ is and the other variables are as defined herein.

In some embodiments of the present disclosure, the $R_9$ is and $R_b$ and the other variables are as defined herein.

In some embodiments of the present disclosure, the compound has the structure represented by formula (III-1) or (III-2):

(III-1)

(III-2)

wherein, m is 0, 1, 2, 3 or 4;

$T_1$, $R_b$, $R_1$, $R_2$, $R_3$, $R_4$, $R_5$, $R_6$, $R_7$ and $R_8$ are as defined herein.

In some embodiments of the present disclosure, the compound has the structure represented by formula (I-3) or (I-4):

(I-3) or (I-4)

wherein, $R_1$, $R_2$, $R_3$, $R_4$, $R_5$, $R_6$, $R_7$ and $R_8$ are as defined herein.

In some embodiments of the present disclosure, the $R_1$ and $R_2$ are each independently H, D, F, Cl or —CH$_3$, and the other variables are as defined herein.

In some embodiments of the present disclosure, the $R_1$ and $R_2$ are each independently H, F, Cl or —CH$_3$, and the other variables are as defined herein.

In some embodiments of the present disclosure, the $R_1$ and $R_2$ are each independently H, and the other variables are as defined herein.

In some embodiments of the present disclosure, the $R_1$ and $R_2$ combining with the carbon atoms to which they are attached form and the other variables are as defined herein.

In some embodiments of the present disclosure, the $R_3$ and $R_4$ are each independently H or —CH$_3$, wherein the —CH₃ is optionally substituted by 1, 2 or 3 substituents independently selected from F, Cl, Br, I and —OH, and the other variables are as defined herein.

In some embodiments of the present disclosure, the R$_3$ and R$_4$ are each independently H or —CH₃, wherein the —CH₃ is optionally substituted by 1, 2 or 3 substituents independently selected from F, Cl, Br and I, and the other variables are as defined herein.

In some embodiments of the present disclosure, the R$_3$ and R$_4$ are each independently H or —CH₃, and the other variables are as defined herein.

In some embodiments of the present disclosure, the R$_5$ and R$_6$ are each independently H or —CH₃, wherein the —CH₃ is optionally substituted by 1, 2, or 3 substituents independently selected from F, Cl, Br, I —OH and —OCH₃, and the other variables are as defined herein.

In some embodiments of the present disclosure, the R$_5$ and R$_6$ are each independently H, —CH₃ or

and the other variables are as defined herein.

In some embodiments of the present disclosure, the R$_5$ and R$_6$ are each independently H or

and the other variables are as defined herein.

In some embodiments of the present disclosure, the compound has the structure represented by formula (III-3) or (III-4):

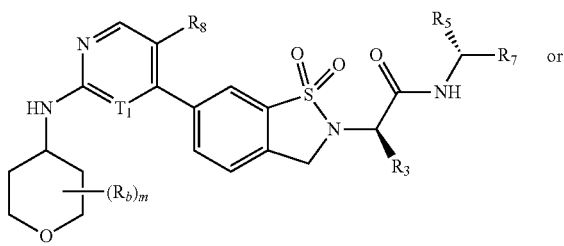

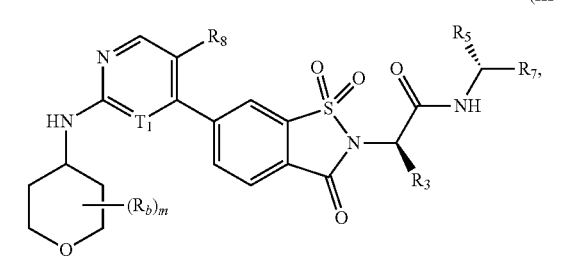

wherein,
m is 0, 1, 2, 3 or 4;
T$_1$, R$_b$, R$_7$ and R$_8$ are as defined herein;
R$_3$ is —CH₃, wherein the —CH₃ is optionally substituted by 1, 2 or 3 substituents independently selected from F, Cl, Br, I and —OH;

R$_5$ is —CH₃, wherein the —CH₃ is optionally substituted by 1, 2 or 3 substituents independently selected from F, Cl, Br, I, —OH and —OCH₃.

In some embodiments of the present disclosure, the compound has the structure represented by formula (I-5) or (I-6):

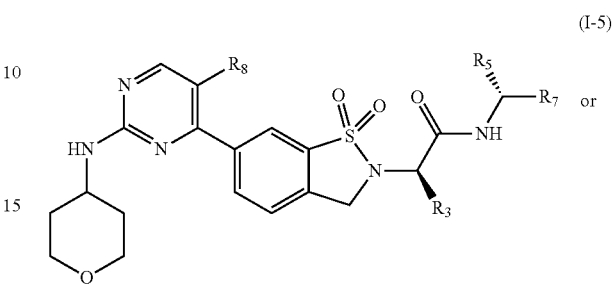

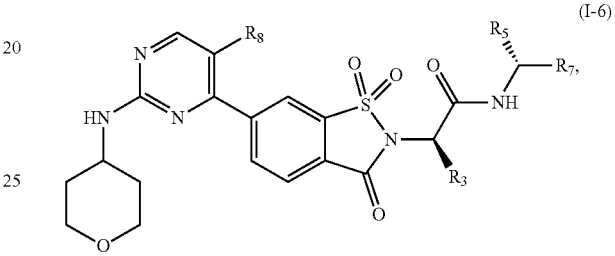

wherein, R$_7$ and R$_8$ are as defined herein;
R$_3$ is —CH₃, wherein the —CH₃ is optionally substituted by 1, 2 or 3 substituents independently selected from F, Cl, Br, I and —OR;
R$_5$ is —CH₃, wherein the —CH₃ is optionally substituted by 1, 2 or 3 substituents independently selected from F, Cl, Br, I, —OR and —OCH₃.

In some embodiments of the present disclosure, the compound has the structure represented by formula (I-5) or (I-6):

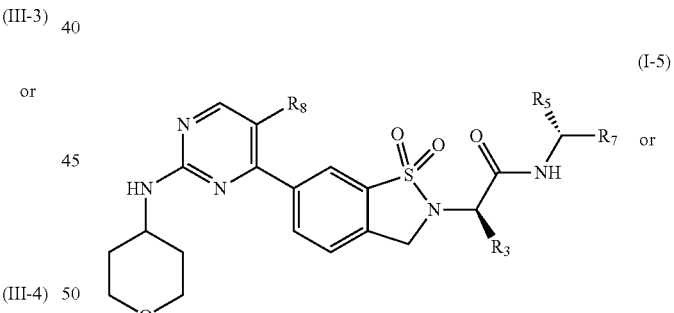

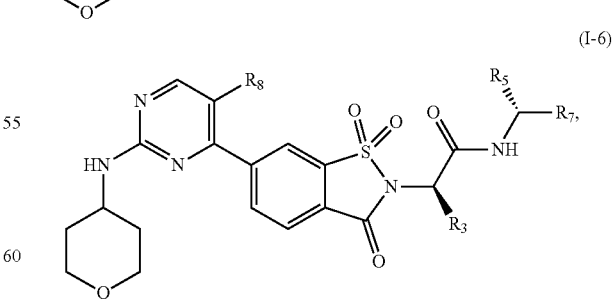

wherein, R$_7$ and R$_8$ are as defined herein;
R$_3$ is —CH₃, wherein the —CH₃ is optionally substituted by 1, 2 or 3 substituents independently selected from F, Cl, Br and I;

$R_5$ is —$CH_3$, wherein the —$CH_3$ is optionally substituted by 1, 2 or 3 substituents independently selected from F, Cl, Br, I, —OH and —$OCH_3$.

In some embodiments of the present disclosure, the $R_a$ is each independently F, Cl, Br, I, —CH, —$OCH_3$, —NH—$CH_3$ or

and the other variables are as defined herein.

In some embodiments of the present disclosure, the $R_a$ is each independently F, Cl, Br, I, —$CH_3$ or —$OCH_3$, and the other variables are as defined herein.

In some embodiments of the present disclosure, the $R_a$ is each independently F, Cl, —$CH_3$, —$OCH_3$ or

and the other variables are as defined herein.

In some embodiments of the present disclosure, the $R_a$ is independently F or —$OCH_3$, and the other variables are as defined herein.

In some embodiments of the present disclosure, the $R_7$ is

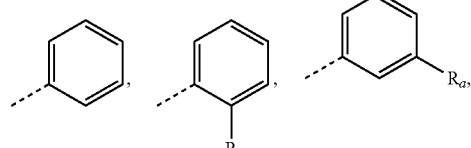

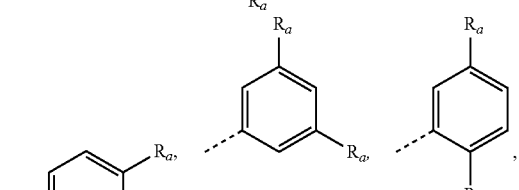

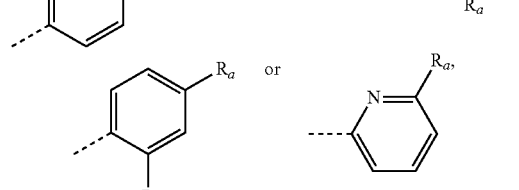

and $R_a$ and the other variables are as defined herein.

In some embodiments of the present disclosure, the $R_7$ is

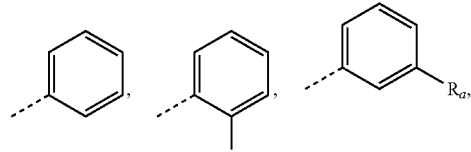

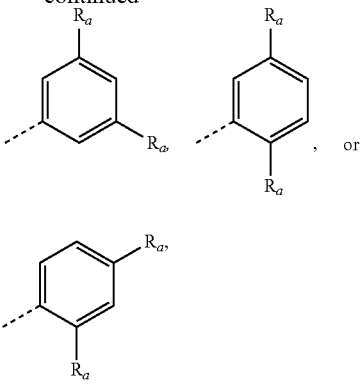

and $R_a$ and the other variables are as defined herein.

In some embodiments of the present disclosure, the $R_7$ is

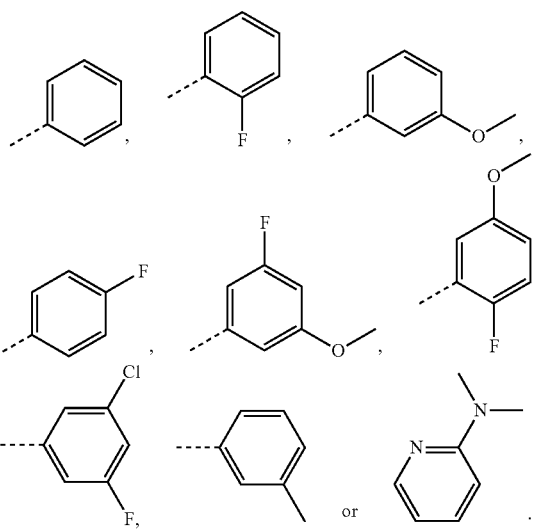

and the other variables are as defined herein.

In some embodiments of the present disclosure, the $R_7$ is

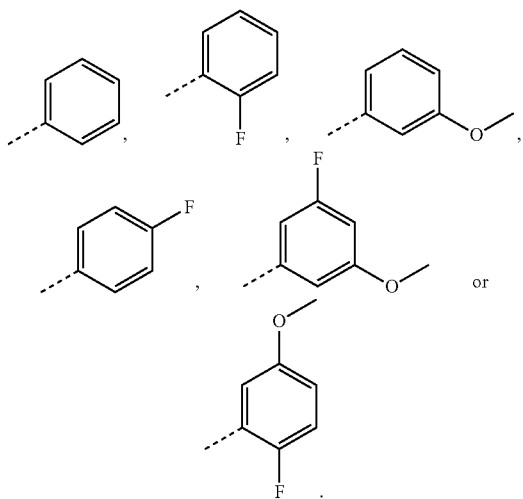

and the other variables are as defined herein.

In some embodiments of the present disclosure, the $R_7$ is

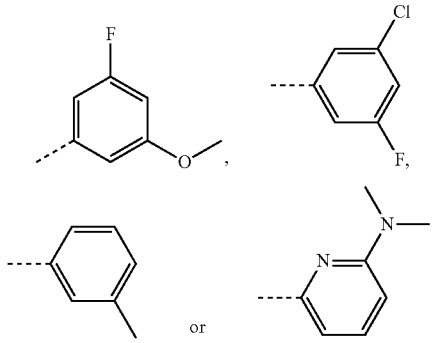

and the other variables are as defined herein.

In some embodiments of the present disclosure, the $R_7$ is

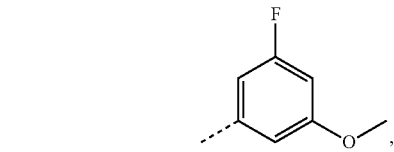

and the other variables are as defined herein.

Some embodiments of the present disclosure are formed by any combination of the above variables.

The present disclosure provides a compound represented by the following formula or a pharmaceutically acceptable salt thereof:

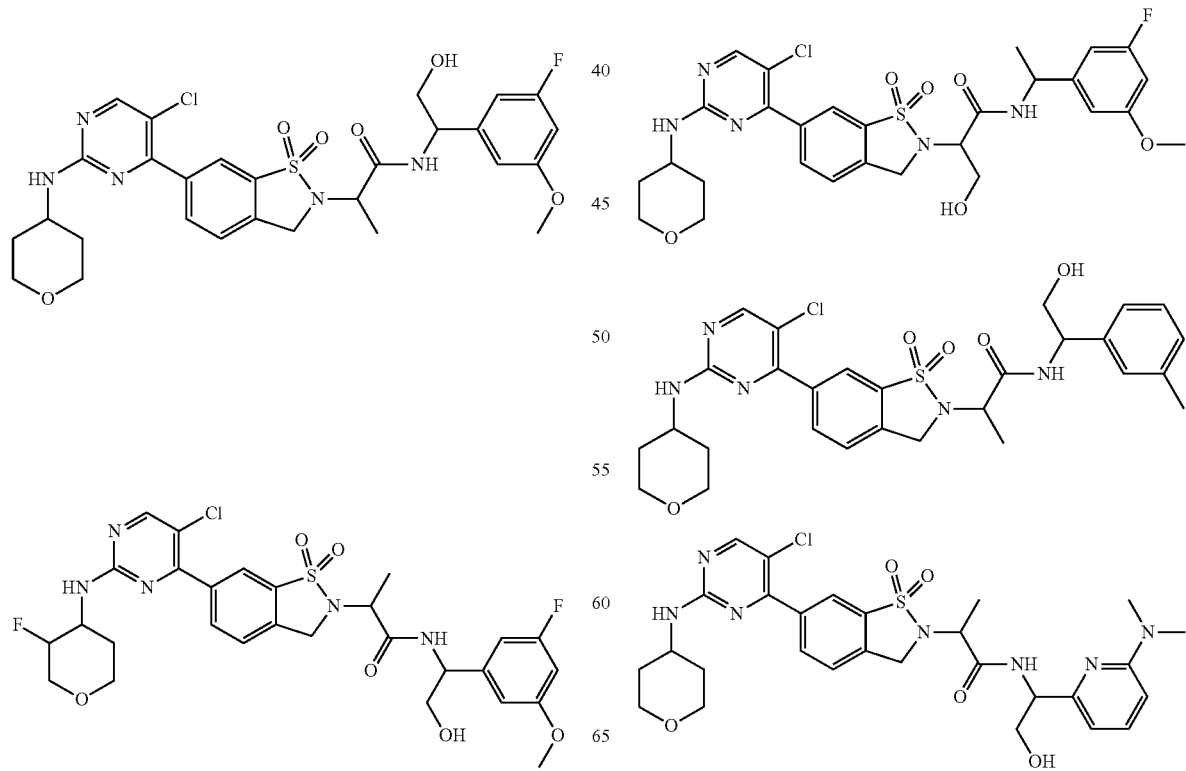

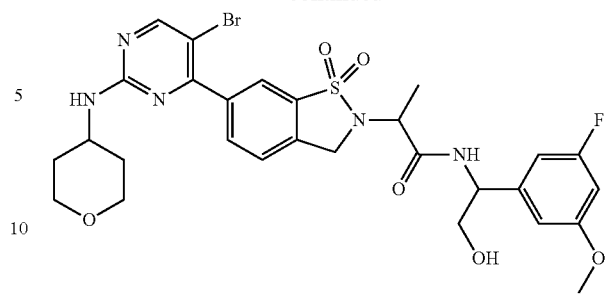

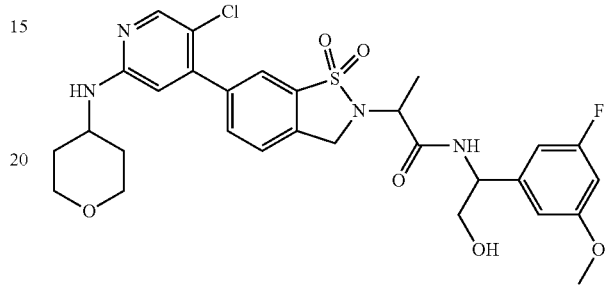

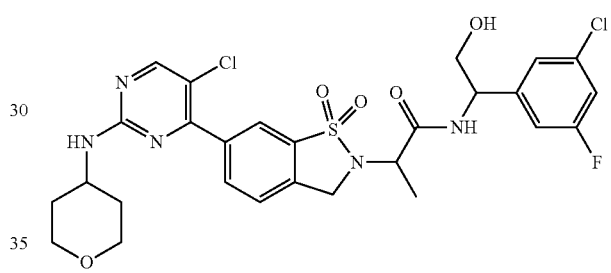

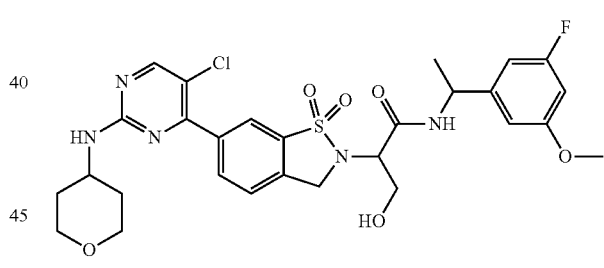

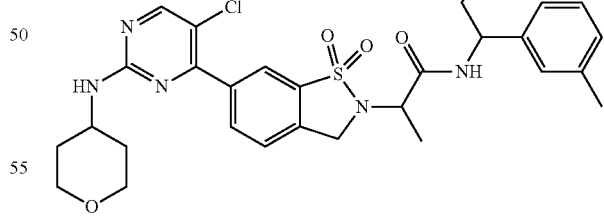

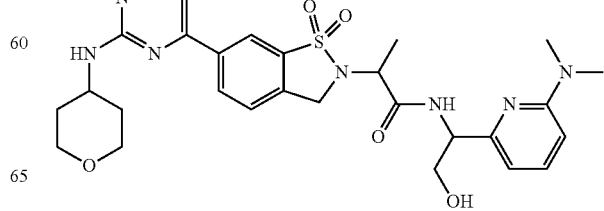

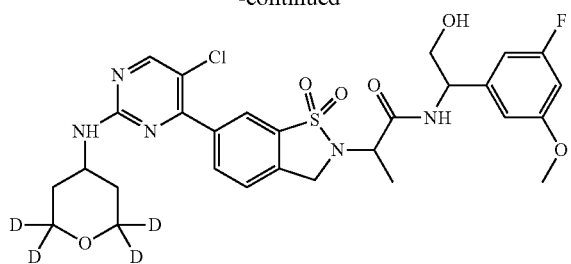
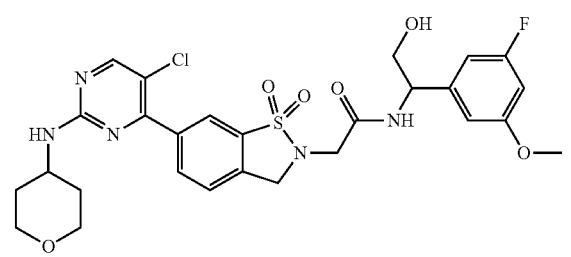
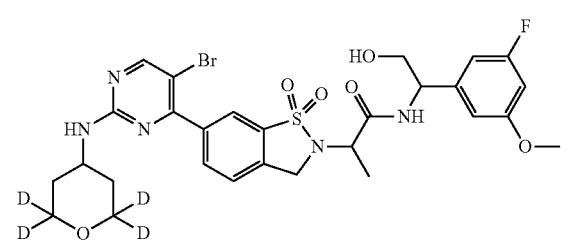
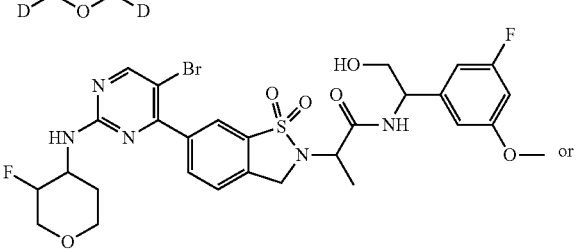
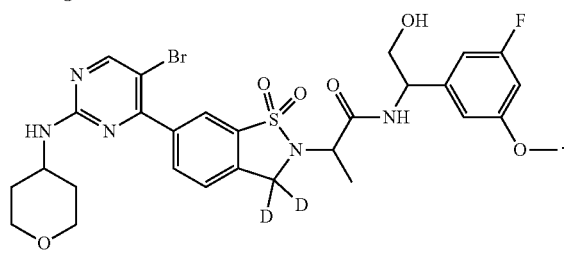
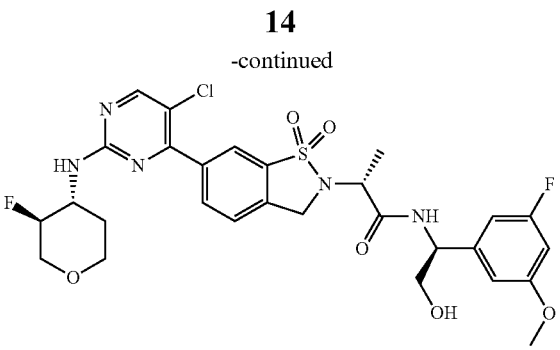
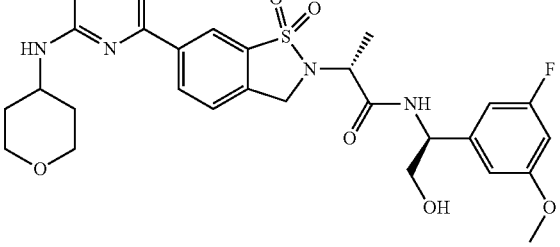
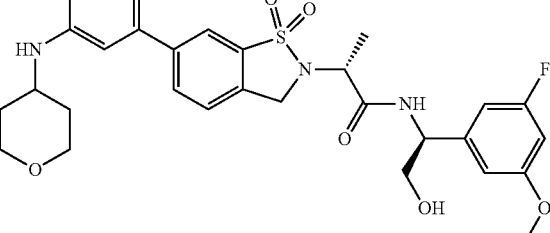
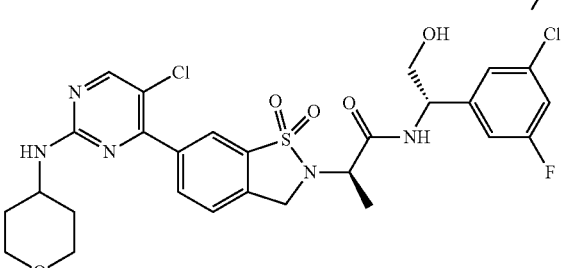
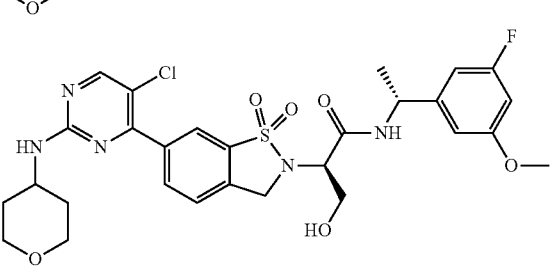
or
The present disclosure provides a compound represented by the following formula or a pharmaceutically acceptable salt thereof:
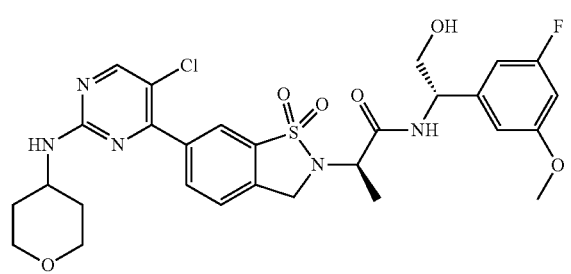
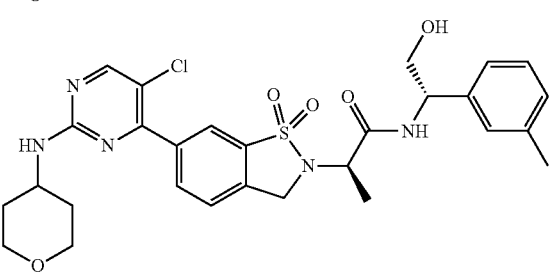

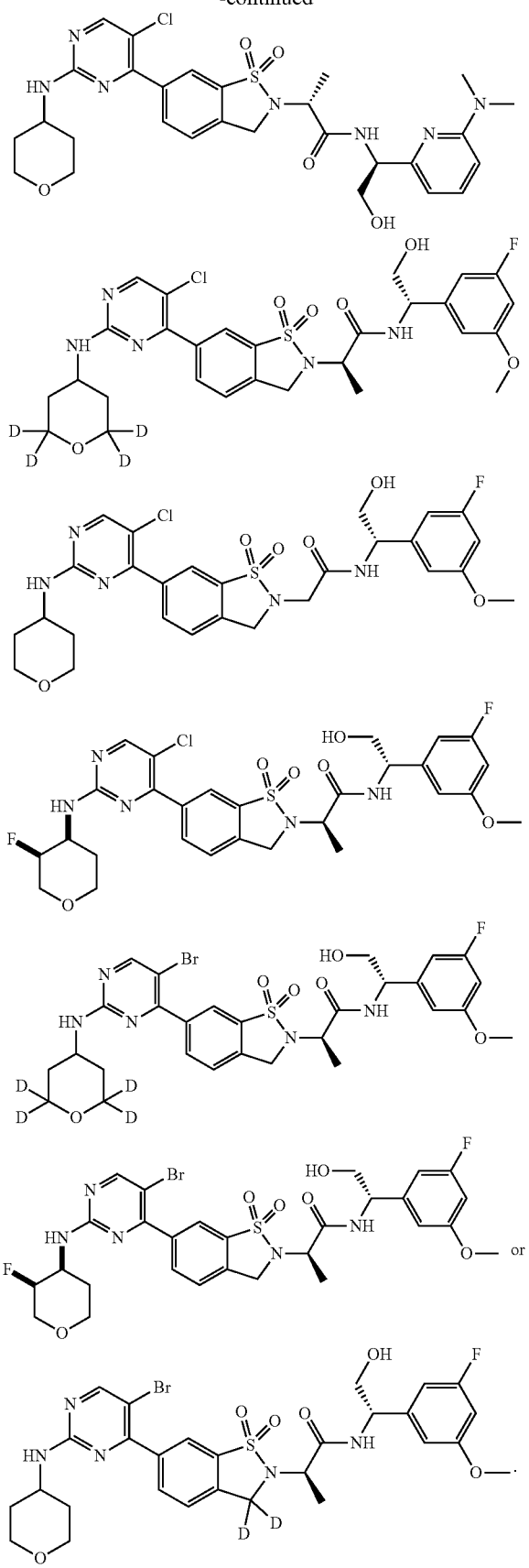

The present disclosure also provides use of the compound or the pharmaceutically acceptable salt thereof in the manufacture of an ERK1/2 inhibitor medicament.

Technical Effects

The compound of the present disclosure has a very good inhibitory activity on ERK1/2. It is expected to be used for canceration caused by abnormal activation of MAPK signaling pathway (activation variation such as RAS/RAF/MEK), and it may also be effective for patients with RAF or MEK inhibitor resistance due to ERK1/2 reactivation; the compound of the present disclosure has good oral absorption in mice and dogs, low clearance rate, high exposure and good bioavailability; the compound of the present disclosure has a significant inhibitory effect on the growth of human lung cancer Calu-6 cell subcutaneous xenograft tumor model tumor-bearing mice.

Definition and Description

Unless otherwise specified, the following terms and phrases when used herein have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, an allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the compound into contact with a sufficient amount of base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt can be obtained by bringing the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, nialeic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like: and salts of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers isomers, (D)-isomers, (L)-isomers, and racemic and other mixtures thereof, such as enantiomers or diastereomeric enriched mixtures, all of which are within the scope of the present disclosure. Additional asymmetric carbon atoms may be present in substituents such as alkyl. All these isomers and their mixtures are included within the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" is caused by the inability to rotate freely of double bonds or single bonds of ring-forming carbon atoms.

Unless otherwise specified, the term "diastereomer" refers to a stereoisomer in which a molecule has two or more chiral centers and the relationship between the molecules is not mirror images.

Unless otherwise specified, "(+)" refers to dextrorotation, "(−)" refers to levorotation, and or refers to racemic.

Unless otherwise specified, the absolute configuration of a stereogenic center is represented by a wedged solid bond ( ◢ ) and a wedged dashed bond ( ◌ ), and the relative configuration of a stereogenic center is represented by a straight solid bond ( ◢ ) and a straight dashed bond ( ◌ ), a wave line ( ◌ ) is used to represent a wedged solid bond ( ◢ ) or a wedged dashed bond ( ◌ ), or the wave line ( ◌ ) is used to represent a straight solid bond ( ◢ ) and a straight dashed bond ( ◌ ).

Unless otherwise specified, the terms "enriched in one isomer", "enriched in isomers", "enriched in one enantiomer" or "enriched in enantiomers" refer to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise specified, the term "isomer excess" or "enantiomeric excess" refers to the differential value between the relative percentages of two isomers or two enantiomers. For example, if the content of one isomer or enantiomer is 90%, and the content of the other isomer or enantiomer is 10%, the isomer or enantiomer excess (ee value) is 80%.

Optically active (R)- and (S)-isomer, or D and L isomer can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from amine). The compound of the present disclosure may contain an unnatural proportion of atomic isotope at one or more than one atom(s) that constitute the compound. For example, the compound can be radiolabeled with a radioactive isotope, such as tritium ($^3H$), iodine-125 ($^{125}I$) or C-14 ($^{14}C$). For another example, deuterated drags can be formed by replacing hydrogen with heavy hydrogen, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs, etc. All isotopic variations of the compound of the present disclosure, whether radioactive or not, are encompassed within the scope of the present disclosure. The term "optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variables, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —$(CRR)_0$—, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist, for example, when X is vacant in A-X, the structure of A-X is actually A. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring.

When the enumerative linking group does not indicate the direction for linking, the direction for linking is arbitrary, for example, the linking group L contained in

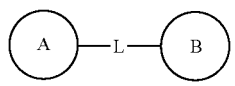

is -M-W-, then -M-W- can link ring A and ring B to form

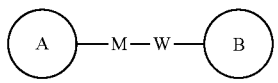

in the direction same as left-to-right reading order, and form

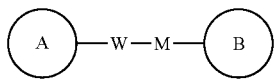

in the direction contrary to left-to-right reading order. A combination of the linking groups, substituents and/or variables thereof is allowed only when such combination can result in a stable compound.

Unless otherwise specified, when a group has one or more linkable sites, any one or more sites of the group can be linked to other groups through chemical bonds. The chemical bond between the site and other groups can be represented by a straight solid bond ( —— ), a straight dashed bond ( ---- ) or a wavy line ( ~~~ ). For example, the straight solid bond in —OCH$_3$ indicates that it is connected to other groups through the oxygen atom in the group; the straight dotted bond in

indicates that it is connected to other groups through both ends of the nitrogen atom in the group; the wavy line in

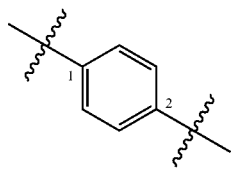 [SMILES: *c1ccc(*)cc1]

indicates that the phenyl group is connected to other groups through the 1 and 2 carbon atoms in the phenyl.

Unless otherwise specified, the number of atoms in a ring is generally defined as the number of ring members, e.g., "5- to 7-membered ring" refers to a "ring" of 5-7 atoms arranged around it.

Unless otherwise specified, "5-membered ring" refers to cycloalkyl, heterocycloalkyl, cycloalkenyl, heterocycloalkenyl, cycloalkynyl, heterocycloalkynyl, aryl or heteroaryl consisting of five ring atoms. The ring includes single ring, and also includes double ring systems such as spiro ring, fused ring and bridged ring. Unless otherwise specified, the ring optionally contains 1, 2 or 3 heteroatoms independently selected from O. S and N. The term "ring" also includes a ring system containing at least one ring, wherein each "ring" independently conforms to the above definition.

Unless otherwise specified, the term "$C_{1-3}$ alkyl" refers to a linear or branched saturated hydrocarbon group consisting of 1 to 3 carbon atoms. The $C_{1-3}$ alkyl includes $C_{1-2}$ and $C_{2-3}$ alkyl, etc; it can be monovalent (such as methyl), divalent (such as methylene) or multivalent (such as methine). Examples of $C_{1-3}$ alkyl include but are not limited to methyl (Me), ethyl (Et), propyl (including n-propyl and isopropyl), etc.

Unless otherwise specified, the term "$C_{1-3}$ haloalkyl" refers to a monohaloalkyl and polyhaloalkyl containing 1 to 3 carbon atoms. The $C_{1-3}$ haloalkyl includes $C_{1-2}$, $C_{2-3}$, $C_3$, $C_2$ and $C_1$ haloalkyl, etc. Examples of $C_{1-3}$ haloalkyl include, but are not limited to, trifluoromethyl, trichloromethyl, 2,2,2-trifluoroethyl, pentafluoroethyl, pentachloroethyl, 3-bromopropyl, etc.

Unless otherwise specified, the term "$C_{1-3}$ alkoxy" refers to an alkyl group containing 1 to 3 carbon atoms that are connected to the rest of the molecule through an oxygen atom. The $C_{1-3}$ alkoxy includes $C_{1-2}$, $C_{2-3}$, $C_3$ and $C_2$ alkoxy, etc. Examples of $C_{1-3}$ alkoxy include, but are not limited to, methoxy, ethoxy, propoxy (including n-propoxy and iso-propoxy), etc.

Unless otherwise specified, the term "$C_{6-10}$ aromatic ring" and "$C_{6-10}$ aryl" are used interchangeably, and the "$C_{6-10}$ aromatic ring" or "$C_{6-10}$ aryl" refers to a cyclic hydrocarbon group with conjugated π electron system consisting of 6 to 10 carbon atoms, which can be a monocyclic, fused bicyclic or fused tricyclic system, where each ring is aromatic. It may be monovalent, divalent or polyvalent, and $C_{6-10}$ aryl includes $C_{6-9}$, $C_9$, $C_{10}$ and $C_6$ aryl, etc. Examples of $C_{6-10}$ aryl include, but are not limited to, phenyl, naphthyl (including 1-naphthyl and 2-naphthyl, etc.).

Unless otherwise specified, $C_{n-n+m}$ or $C_n$-$C_{n+m}$, includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and any range from n to n+m is also included, for example $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$, etc.: similarly, n-membered to n+m-membered means that the number of atoms on the ring is from n to n+m, for example, 3- to 12-membered ring includes 3-membered ring, 4-membered ring, 5-membered ring, 6-membered ring, 7-membered ring, 8-membered ring, 9-membered ring, 10-membered ring, 11-membered ring, and 12-membered ring, and any range from n to n+m is also included, for example, 3- to 12-membered ring includes 3- to 6-membered ring, 3- to 9-membered ring, 5- to 6-membered ring, 5- to 7-membered ring, 6- to 7-membered ring, 6- to 8-membered ring, and 6- to 10-membered ring, etc.

The term "D" refers to deuterium, an isotope of hydrogen, and its chemical symbol can also be $^2$H, also known as heavy hydrogen, which is composed of a proton, a neutron and an electron.

The term "leaving group" refers to a functional group or atom which can be replaced by another functional group or atom through a substitution reaction (such as affinity substitution reaction). For example, representative leaving groups include triflate; chlorine, bromine, and iodine; sulfonate group, such as mesylate, tosylate, p-bromobenzenesulfonate, p-toluenesulfonates, etc; acyloxy, such as acetoxy, trifluoroacetoxy, etc.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl, such as benzyl (Bn), trityl (Tr), 1,1-bis-(4'-methoxyphenyl) methyl; silyl, such as trimethylsilyl (TMS) and tert-butyldimethylsilyl (TBS), etc. The term "hydroxy protecting group" refers to a protecting group suitable for blocking the side reaction on hydroxy. Representative hydroxy protecting groups include, but are not limited to: alkyl, such as methyl, ethyl, and tert-butyl: acyl, such as alkanoyl (e.g., acetyl); arylmethyl, such as benzyl (Bn), p-methoxybenzyl (PMB), 9-fluorenylmethyl (Fm), and diphenylmethyl (benzhydryl, DPM); silyl, such as trimethylsilyl (TMS) and tert-butyl dimethyl silyl (TBS), etc.

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The structure of the compounds of the present disclosure can be confirmed by conventional methods known to those skilled in the art, and if the disclosure involves an absolute configuration of a compound, then the absolute configuration can be confirmed by means of conventional techniques in the art. For example, in the case of single crystal X-ray diffraction (SXRD), the absolute configuration can be confirmed by collecting diffraction intensity data from the cultured single crystal using a Bruker D8 venture diffractometer with CuKα radiation as the light source and scanning mode: φ/ω scan, and after collecting the relevant data, the crystal structure can be further analyzed by direct method (Shelxs97) to confirm the absolute configuration.

The solvent used in the present disclosure is commercially available.

The present disclosure adopts the following abbreviations: $BF_3 \cdot Et_2O$ stands for boron trifluoride diethyl etherate complex; DMSO stands for dimethyl sulfoxide; DMF stands for N,N-dimethylformamide; DPBS stands for Dulbecco's phosphate buffered saline; EDCI stands for 1-(3-dimethylaminopropyl)-3-ethylcarbodiimide; HOBt stands for 1-hydroxybenzotriazole; HPLC stands for high-pressure liquid chromatography; LCMS stands for liquid chromatography-mass spectrometry; MeOH stands for methanol; NMM stands for N-methylmorpholine; $Pd(dppf)Cl_2 \cdot CH_2Cl_2$ stands for [1,1'-bis(diphenylphosphino)ferrocene]palladium dichloride dichloromethane complex; $Pd(PPh_3)_4$ stands for tetrakis(triphenylphosphine)palladium: PBS stands for phosphate buffer; HATU stands for O-(7-azabenzotriazol-1-yl)-N,N,N',N'-tetramethyluronium hexafluorophosphate; PMB stands for p-methoxybenzyl; NMP stands for N-methyl pyrrolidone; DIEA stands for N,N-diisopropylethylamine; $LiAlD_4$ stands for deuterated lithium aluminum hydride; MsCl stands for methanesulfonyl chloride: BNS stands for N-bromosuccinimide; AIBN stands for azodiisobutyronitrile.

DETAILED DESCRIPTION OF THE INVENTION

Figure 1:
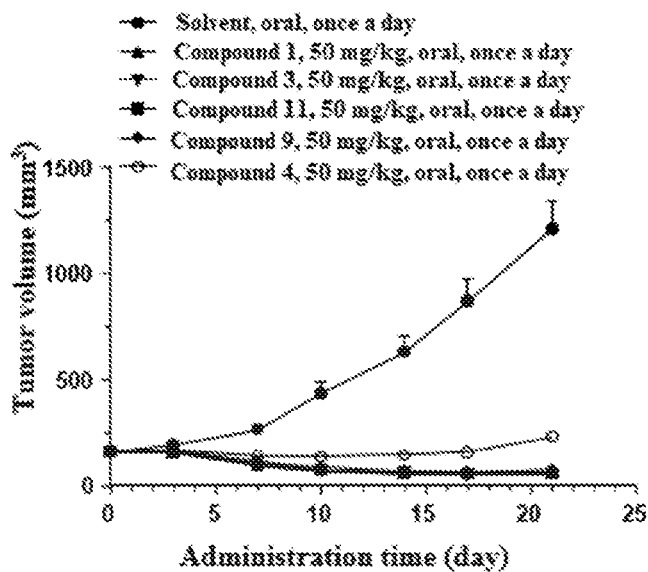
FIG. 1: The tumor volume of each group at different time point.

The present disclosure is described in detail by the embodiments below, but it does not mean that there are any adverse restrictions on the present disclosure. The present disclosure has been described in detail herein, wherein specific embodiments thereof are also disclosed, and it will be apparent to those skilled in the art that various variations and improvements can be made to specific embodiments of the present disclosure without departing from the spirit and scope of the present disclosure.

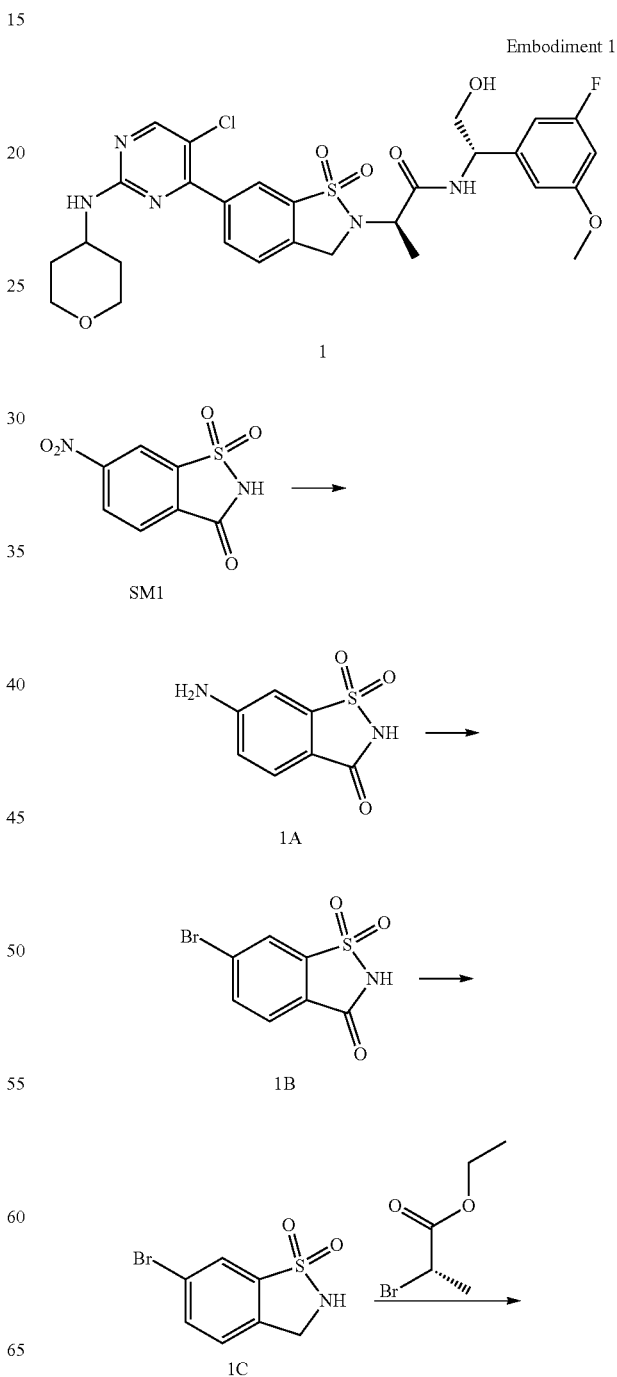

Embodiment 1

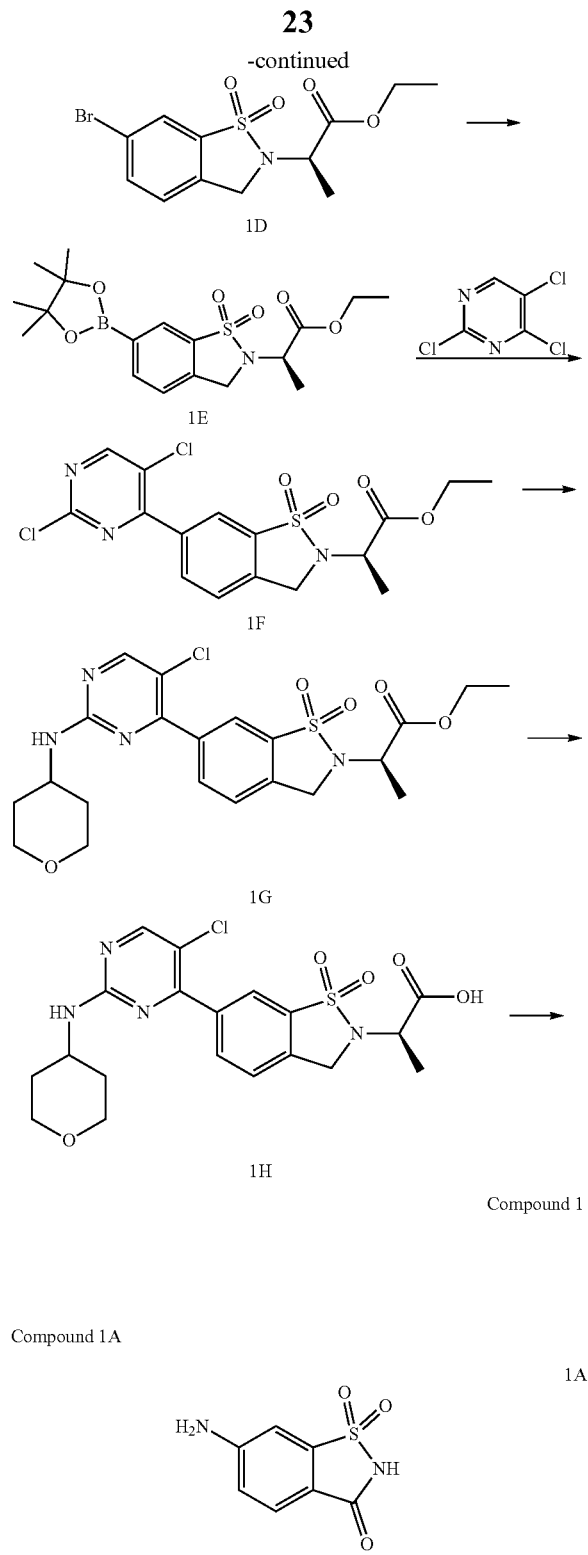

Compound 1A

Compound SM1 (4 g, 17.53 mmol) and Pd/C (400 mg, 17.53 mmol, 100% purity) were dissolved in methanol (40 mL), and the reaction solution was replaced with hydrogen for three times to discharge the air, and then stirred at 15° C. for 2 hours under the protection of hydrogen (15 psi). The reaction solution was filtered, and the filtrate was concentrated under reduced pressure to obtain a crude product of 1A, and the crude product was directly used in the next reaction. $^1$H NMR (400 MHz, DMSO-d$_6$) δ=7.59 (d, J=8.4 Hz, 1H), 6.94 (d, J=2.0 Hz, 1H), 6.89 (dd, J=1.9, 8.5 Hz, 1H).

Compound 1B

A solution of compound 1A (2.66 g, 13.42 mmol) in acetonitrile (30 mL) was added dropwise to a solution of compound copper bromide (3.00 g, 13.43 mmol, 628.93 μL) and tert-butyl nitrite (3.38 g, 32.79 mmol, 3.9 mL) in acetonitrile (30 mL) at 0° C. The reaction solution was stirred at 0° C. for 1 hour after the dropwise addition was completed. Then the mixture was stirred at 15° C. for 15 hours. The reaction solution was diluted with water (100 mL), and the pH was adjusted to 2 or less with hydrochloric acid solution (2 mol). Then the reaction solution was extracted with ethyl acetate (100 mL×2 times). The organic phases were combined and concentrated under reduced pressure to obtain compound 1B. $^1$H NMR (400 MHz, DMSO-d$_6$) δ=8.51 (d, J=1.2 Hz, 1H), 8.09 (dd, J=1.7, 8.2 Hz, 1H), 7.87 (d, J=8.2 Hz, 1H).

Compound 1C

Compound 1B (4.26 g, 16.25 mmol) was dissolved in tetrahydrofuran (50 mL), and sodium borohydride (6.40 g, 169.05 mmol) was added. The reaction solution was cooled to −8° C., and then BF$_3$·Et$_2$O (26.45 g, 186.36 mmol, 23 mL) was added dropwise at −8° C. And the mixture was stirred at −8° C. for 10 minutes. Then the mixture was stirred at 80° C. for 2 hours. The reaction solution was poured into ice water (120 mL), and the pH of the reaction solution was adjusted to 10 with 2 mol of sodium hydroxide (100 mL) solution. The reaction solution was extracted with ethyl acetate (100 mL). The organic phase was extracted with 2 mol of sodium hydroxide (50 mL×3 times) aqueous solution. The pH of the combined aqueous phase was adjusted to 2 with 2 mol of hydrochloric acid (500 mL) solution, then the aqueous phase was extracted with ethyl acetate (300 mL×2 times), and the combined organic phase was concentrated under reduced pressure to obtain a crude product of compound 1C. $^1$H NMR (400 MHz. DMSO-d$_6$) δ=8.12 (d, J=1.6 Hz, 1H), 7.97 (br s, 1H), 7.87 (dd, J=1.8, 8.2 Hz, 1H), 7.53 (d, J=8.3 Hz, 1H), 4.37 (br s, 2H).

Compound 1D

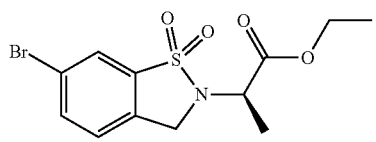

Under the protection of nitrogen, compound 1C (3.1 g, 12.50 mmol), ethyl (2S)-2-bromopropanoate (3.40 g, 18.78 mmol) and potassium carbonate (5.06 g, 36.65 mmol) were dissolved in DMF (30 mL), and the mixture was stirred for 1 hour at 20° C. The reaction solution was diluted with 50 mL of water and then extracted with ethyl acetate (50 mL×3 times). The organic phases were combined and concentrated under reduced pressure to obtain a crude product, and the crude product was purified by silica gel column chromatography (eluting with petroleum ether:ethyl acetate=10:1 to 5:1) to obtain compound ID. $^1$H NMR (400 MHz, CDCl$_3$) δ=7.93 (d, J=1.5 Hz, 1H), 7.72 (dd, J=1.8, 8.2 Hz, 1H), 7.30 (d, J=8.3 Hz, 1H), 4.82 (d, J=14.1 Hz, 1H), 4.59-4.46 (m, 2H), 4.20 (dq, J=1.4, 7.2 Hz, 2H), 1.63 (d, J=7.3 Hz, 3H), 1.26 (s, 3H).

Compound 1E

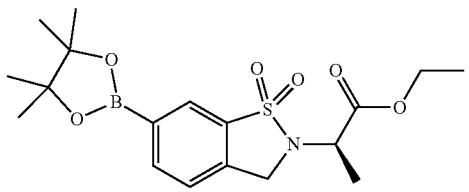

Under the protection of nitrogen, bis(pinacolato)diboron (1.19 g, 4.69 mmol), compound ID (1.36 g, 3.91 mmol), Pd(dppf)Cl$_2$·CH$_2$Cl$_2$ (319 mg, 390.63 μmol) and potassium acetate (767 mg, 7.82 mmol) were dissolved in dioxane (14 mL), and the mixture was stirred at 90° C. for 16 hours. The reaction solution was filtered, and the filtrate was concentrated under reduced pressure to obtain a crude product of compound 1E.

Compound 1F

Under the protection of nitrogen, compound 1E (2.53 g, 6.40 mmol), 2,4,5-trichloropyrimidine (2.35 g, 12.81 mmol), Pd(PPh$_3$)$_4$ (740 mg, 640.38 μmol) and sodium carbonate (1.36 g, 12.83 mmol) were dissolved in dioxane (24 mL) and water (8 mL), and the mixture was stirred at 90° C. for 2 hours. The reaction solution was filtered, and then ethyl acetate (50 mL) was added to the filtrate, and the solution was washed with saturated sodium chloride solution (50 mL×3 times). The organic phases were combined and concentrated under reduced pressure to obtain a crude product, and the crude product was purified by silica gel column chromatography (eluting with petroleum ether:ethyl acetate=10:1 to 4:1) to obtain compound 1F. $^1$H NMR (400 MHz, CDCl$_3$) δ=8.72 (s, 1H), 8.42 (d, J=1.1 Hz, 1H), 8.19 (dd, J=1.7, 8.1 Hz, 1H), 7.59 (d, J=8.1 Hz, 1H), 4.99 (d, J=14.5 Hz, 1H), 4.71-4.54 (m, 2H), 4.22 (dq, J=1.5, 7.2 Hz, 2H), 1.67 (d, J=7.2 Hz, 3H), 1.30-1.26 (m, 3H).

Compound 1G

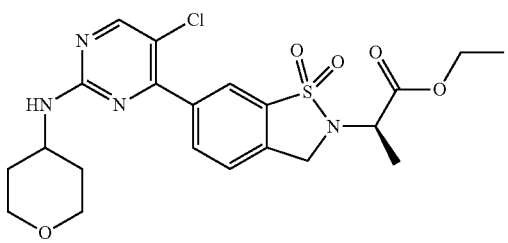

Under the protection of nitrogen, compound 1F (865 mg, 2.08 mmol), 4-aminotetrahydropyran (420 mg, 4.15 mmol) and DIEA (675.22 mg, 5.22 mmol, 910 μL) were dissolved in dioxane (9 mL), and the mixture was stirred at 90° C. for 16 hours. The reaction solution was diluted with ethyl acetate (20 mL) and washed with 1 mol of hydrochloric acid (20 mL×1 time) aqueous solution, and then the aqueous phase was extracted with ethyl acetate (20 mL×2 times), and the combined organic phase was washed with brine (20 mL×1 time), dried and concentrated under reduced pressure to obtain a crude product of compound 1G. $^1$H NMR (400 MHz, CDCl$_3$) δ=8.33 (s, 1H), 8.27 (s, 1H), 8.08 (dd, J=1.3, 8.1 Hz, 1H), 7.52 (d, J=8.1 Hz, 1H), 5.34 (br s, 1H), 4.95 (d, J=14.3 Hz, 1H), 4.64-4.58 (m, 2H), 4.22 (dq, J=1.4, 7.1 Hz, 2H), 4.03-3.98 (m, 2H), 3.56 (dt, J=1.7, 11.5 Hz, 2H), 2.07-2.02 (m, 2H), 1.67 (d, J=7.4 Hz, 3H), 1.61-1.55 (m, 2H), 1.31-1.27 (m, 3H).

Compound 1H

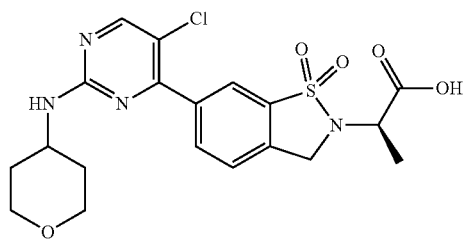

Lithium hydroxide monohydrate (4 mol, 1.1 mL) was added to a solution of compound 1G (1.03 g, 2.14 mmol) in tetrahydrofuran (10 mL) and methanol (10 mL). The reaction solution was stirred at 20° C. for 16 hours. The reaction solution was concentrated under reduced pressure, and the pH was adjusted to 4 with 2 mol of hydrochloric acid (2 mL) solution, and then the solution was extracted with ethyl acetate (20 mL×3 times). The combined organic phase was filtered, and the filtrate was concentrated under reduced pressure to obtain a crude product of compound 1H. $^1$H NMR (400 MHz, CDCl$_3$) δ=8.32 (br s, 1H), 8.23 (s, 1H), 8.03 (br d, J=7.5 Hz, 1H), 7.52 (d, J=8.0 Hz, 1H), 6.15-6.07 (m, 1H), 4.83 (br d, J=13.7 Hz, 1H), 4.67-4.55 (m, 3H), 4.02-3.96 (m, 3H), 3.58-3.51 (m, 2H), 2.02 (br d, J=10.7 Hz, 2H), 1.69 (d, J=7.3 Hz, 3H), 1.27 (t, J=7.2 Hz, 2H).

Compound 1

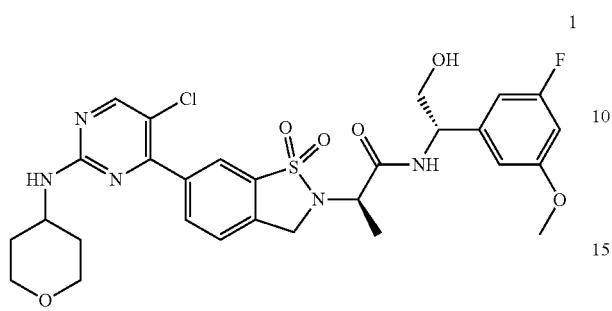

Under the protection of nitrogen, compound 1H (247 tug, 545.36 μmol), (2S)-2-amino-2-(3-fluoro-5-methoxy-phenyl) ethanol (101 mug, 545.37 μmol), HOBt (82 mg, 606.85 μmol), NMM (61 mg, 603.08 μmol, 66.30 μL) and EDCI (115 mg, 599.89 μmol) were dissolved in a mixed solvent of DMF (3 mL) and dichloromethane (6 mL), and the mixture was stirred at 20° C. for 16 hours. The reaction solution was concentrated under reduced pressure to obtain a residue, and the residue was diluted with dichloromethane (40 mL) and then washed with hydrochloric acid aqueous solution (2 mol, 40 mL×2 times). The combined organic phase was filtered, and the filtrate was concentrated under reduced pressure to obtain a crude product. The crude product was separated by preparative high performance liquid chromatography (trifluoroacetic acid system) to obtain a freebase of compound 1. $^1$H NMR (400 MHz, MeOH-d$_4$) δ=8.38 (s, 1H), 8.24 (d, J=0.9 Hz, 1H), 8.16 (dd, J=1.5, 8.1 Hz, 1H), 7.71 (d, J=8.1 Hz, 1H), 6.77 (s, 1H), 6.70 (br d, J=9.4 Hz, 1H), 6.65-655 (in, 1H), 4.99-4.91 (m, 2H), 4.71 (d, J=14.7 Hz, 1H), 4.64-4.59 (m, 1H), 4.09-3.95 (m, 3H), 3.81 (s, 3H), 3.79-3.67 (m, 2H), 3.55 (dt, J=1.9, 11.6 Hz, 2H), 2.01 (br dd, J=2.0, 12.5 Hz, 2H), 1.70-1.57 (m, 5H). LCMS (ESI) m/z: 620.3 [M+1].

Embodiment 2

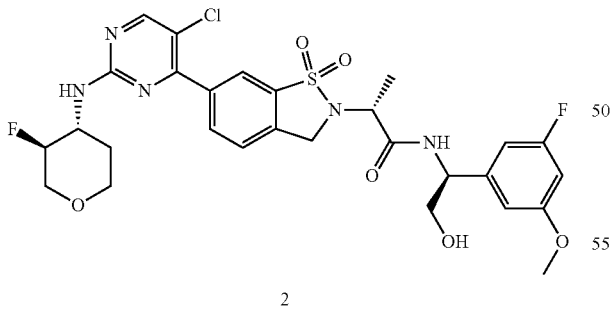

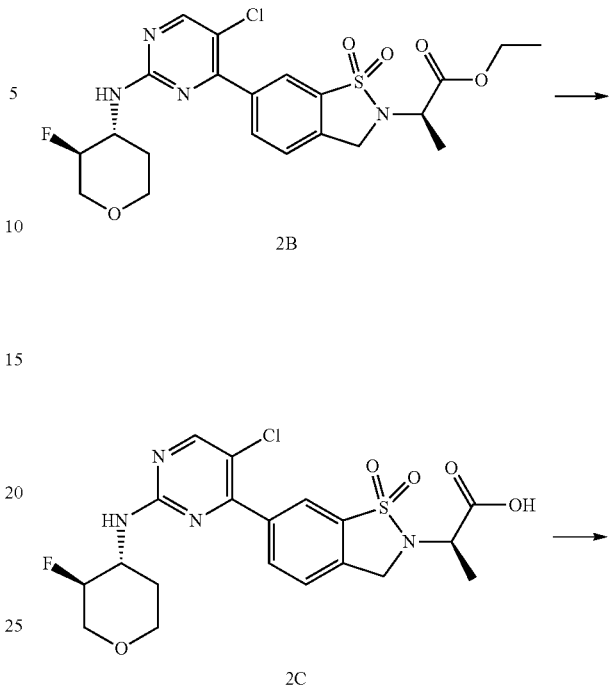

Compound 2B

Compound 2

Compound 2A (74.76 mg, 480.45 μmol, HCl) and DIEA (186.28 mug, 1.44 mmol, 251.06 μL) were added to a solution of compound 1F (200 mg, 480.45 μmol) in dioxane (3 mL), and the reaction solution was stirred at 90° C. for 24 hours. After the reaction was completed, the reaction solution was diluted with ethyl acetate (20 mL) and washed with 1 mol of hydrochloric acid (20 mL×1 time) aqueous solution. The aqueous phase was extracted with ethyl acetate (20 mL×2 times), and the combined organic phase was washed with brine (20 mnL×1 time), dried and concentrated under reduced pressure to obtain a crude product of compound 2B. $^1$H NMR (400 MHz, CDCl$_3$) δ=837 (s, 1H), 8.29 (s, 1H), 8.09 (dd, 1H, J=1.5, 8.2 Hz), 7.53 (d, 1H, J=8.1 Hz), 5.32 (br d, 1H, J=8.1 Hz), 4.96 (d, 1H, J=14.3 Hz), 4.6-4.7 (m, 2H), 4.46 (s, 2H), 4.1-4.2 (m, 2H), 3.8-3.9 (m, 1H), 3.5-3.6 (m, 2H), 2.2-2.4 (m, 1H), 1.67 (d, 3H, J=7.3 Hz), 1.3-1.3 (m, 3H). LCMS (ESI): m/z: 416.2 [M+1].

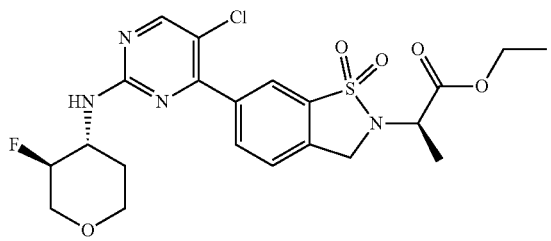

Compound 2C

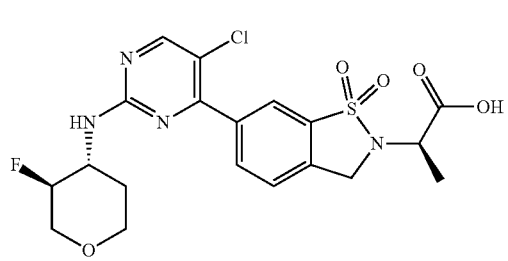

An aqueous (0.5 mL) solution of lithium hydroxide monohydrate (15.14 mg, 360.75 μmol) was added to a solution of compound 2B (60 mg, 120.25 μmol) in tetrahydrofuran (3 mL), and the reaction solution was stirred at 25° C. for 1 hour. After the reaction was completed, the reaction solution was concentrated under reduced pressure, and the pH was adjusted to 4 with 2 mol of hydrochloric acid (2 mL) solution, and then the solution was extracted with ethyl acetate (20 mL×3 times). The combined organic phase was filtered, and the filtrate was concentrated under reduced pressure to obtain a crude product of compound 2C. LCMS (ESI): m/z: 471.0 [M+1].

Compound 2C

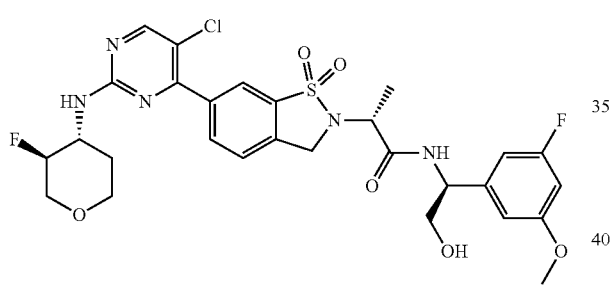

(2S)-2-Amino-2-(3-fluoro-5-methoxy-phenyl)ethanol (28.24 mg, 127.42 μmol) and DIEA (41.17 mg, 318.54 μmol, 55.48 μL) were added to a solution of compound 2C (50 mg, 106.18 μmol) in dichloromethane (3 mL), and the mixture was stirred at 0° C. for 15 minutes, and then HATU (48.45 mg, 127.42 μmol) was added to the mixture, and the reaction solution was stirred at 0° C. for 1 hour. The pH of the reaction solution was adjusted to below 7 with hydrochloric acid (2 M) aqueous solution, then the mixture was extracted with dichloromethane (10 mL×2 times), and then washed with water (10×1 time). The combined organic phase was filtered, and the filtrate was concentrated under reduced pressure to obtain a crude product. The crude product was separated by preparative high performance liquid chromatography (formic acid system) to obtain a freebase of compound 2. $^1$H NMR (CD$_3$OD, 400 MHz) δ=8.41 (s, 1H), 8.26 (d, 1H, J=1.1 Hz), 8.18 (dd, 1H, J=1.6, 8.1 Hz), 7.72 (d, 1H, J=8.1 Hz), 6.77 (s, 1H), 6.70 (td, 1H, J=1.7, 9.3 Hz), 6.6-6.6 (m, 1H), 5.0-5.0 (m, 1H), 4.72 (d, 1H, J=14.8 Hz), 4.5-4.7 (m, 4H), 4.2-4.4 (m, 1H), 4.07 (dt, 1H, J=3.9, 11.2 Hz), 3.9-4.0 (m, 1H), 3.81 (s, 3H), 3.7-3.8 (m, 2H), 3.5-3.6 (m, 2H), 2.1-2.3 (m, 1H), 1.7-1.8 (m, 1H), 1.62 (d, 3H, J=7.1 Hz). LCMS (ESI): m/z: 638.0 [M+1].

Embodiment 3

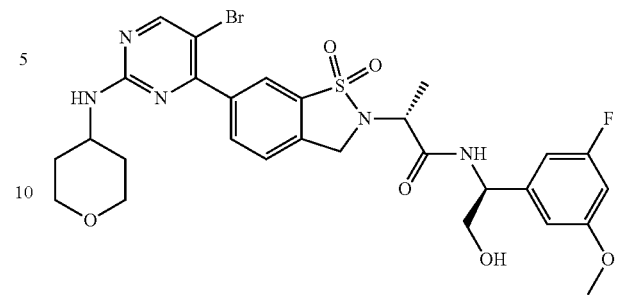

3

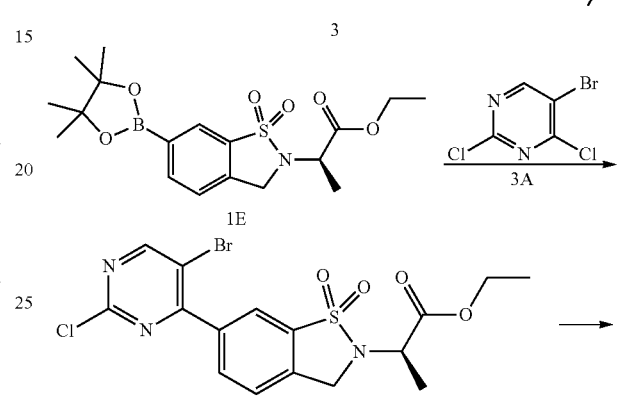

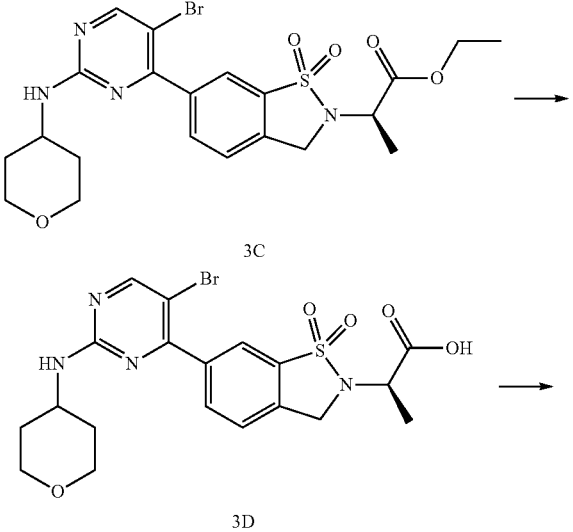

Compound 3B

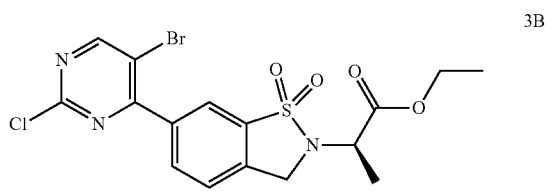

Under the protection of nitrogen, compound 1E (500 mg, 1.26 mmol), 3A (454 mg, 1.99 mmol, 255.06 μL), Pd(PPh$_3$)$_4$ (145 mg, 125.48 μmol) and sodium carbonate (409 mg, 3.86 mmol) were dissolved in dioxane (8 mL) and water (2 mL), and the mixture was stirred at 100° C. for 1 hour. The reaction solution was filtered, and then ethyl acetate (30 mL) was added to the filtrate, and the solution was washed with saturated sodium chloride solution (30 mL×1 time). The organic phases were combined and concentrated under reduced pressure to obtain a crude product, and the crude product was purified by silica gel column chromatography (eluting with petroleum ether:ethyl acetate=1:1) to obtain compound 3B. $^1$H NMR (400 MHz, CDCl$_3$) δ=8.84 (s, 1H), 8.35 (d, J=1.3 Hz, 1H), 8.12 (dd, J=1.6, 8.1 Hz, 1H), 7.58 (d, J=8.1 Hz, 1H), 4.98 (d, J=14.4 Hz, 1H), 4.67-4.57 (m, 2H), 4.25-4.18 (m, 2H), 1.67 (d, J=7.3 Hz, 3H), 1.31-1.27 (m, 3H). LCMS (ESI): m/z: 527.2 [M+1]. LCMS (ESI): m/z: 461.9 [M+1].

Compound 3C

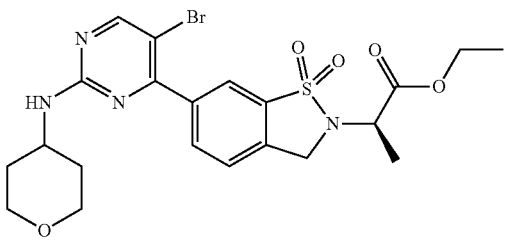

3C

DIEA (61 mg, 471.98 μmol, 82.21 μL) and 4-aminotetrahydropyran (66 mg, 652.52 μmol) were added to a solution of compound 3B (100 mg, 217.05 μmol) in dioxane (3 mL). The reaction solution was stirred at 90° C. for 16 hours. After the reaction was completed, the mixture was diluted with water (10 mL) and extracted with ethyl acetate (10 mL×2 times). The organic phases were combined and concentrated under reduced pressure to obtain a crude product, and the crude product was purified by silica gel column chromatography (eluting with petroleum ether:ethyl acetate=1:1) to obtain compound 3C. LCMS (ESI): m/z: 527.2 [M+1].

Compound 3D

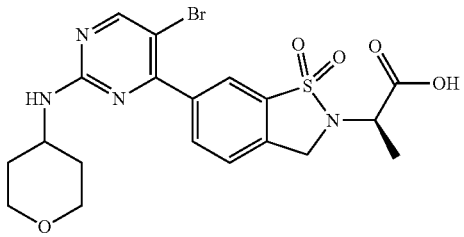

3D

An aqueous (1 mL) solution of lithium hydroxide monohydrate (12 mg, 285.96 μmol) was added to a solution of compound 3C (100 mg, 190.33 μmol) in tetrahydrofuran (1 mL) and ethanol (1 mL), and the reaction solution was stirred at 25° C. for 1 hour. After the reaction was completed, the reaction solution was concentrated under reduced pressure, and the pH was adjusted to 2 with hydrochloric acid (2 mol) aqueous solution, and then the solution was extracted with ethyl acetate (10 mL×3 times). The combined organic phase was filtered, and the filtrate was concentrated under reduced pressure to obtain a crude product of compound 3D. LCMS (ESI): m/z: 497.2 [M+1].

Compound 3

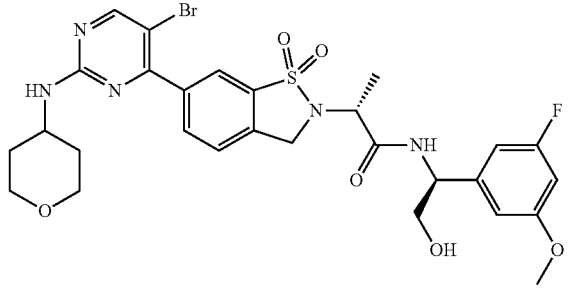

3

(2S)-2-Amino-2-(3-fluoro-5-methoxy-phenyl)ethanol (58 mg, 261.67 μmol) and DIEA (74.20 mg, 574.11 μmol, 100 μL) were added to a solution of compound 3D (70 mg, 140.74 μmol) in dichloromethane (3 mL, and the reaction solution was stirred at 0° C. for 5 minutes. Then HATU (70 mg, 184.10 μmol) was added to the reaction solution, and continued to react for 2 hours. The pH of the reaction solution was adjusted to below 7 with hydrochloric acid (2 M) aqueous solution, then the mixture was extracted with dichloromethane (10 mL×2 times), and then washed with water (10 mL×1 time). The combined organic phase was filtered, and the filtrate was concentrated under reduced pressure to obtain a crude product. The crude product was separated by preparative high performance liquid chromatography (formic acid system) to obtain a freebase of compound 3. $^1$H NMR (400 MHz, CD$_3$OD) δ=8.46 (s, 1H), 8.15 (d, J=1.1 Hz, 1H), 8.08 (dd, J=1.6, 8.1 Hz, 1H), 7.68 (d, J=8.1 Hz, 1H), 6.75 (s, 1H), 6.72-6.65 (m, 1H), 6.59 (td, J=2.3, 10.8 Hz, 1H), 4.95-4.90 (m, 2H), 4.69 (d, J=14.6 Hz, 1H), 4.60 (s, 1H), 4.07-3.93 (m, 3H), 3.79 (s, 3H), 3.75-3.66 (m, 2H), 3.52 (dt, J=1.9, 11.6 Hz, 2H), 2.03-1.94 (m, 2H), 1.68-1.53 (m, 5H). LCMS (ESI): m/z: 666.3 [M+1].

Embodiment 4

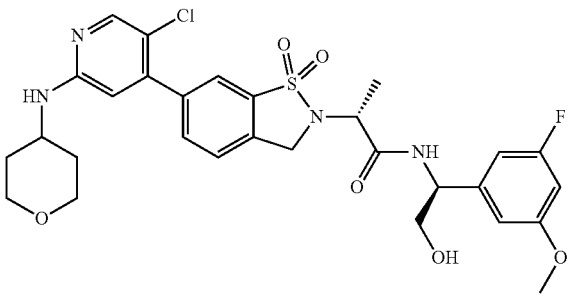

4

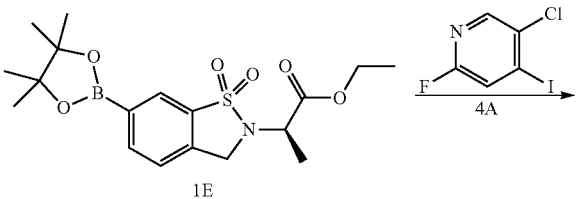

-continued

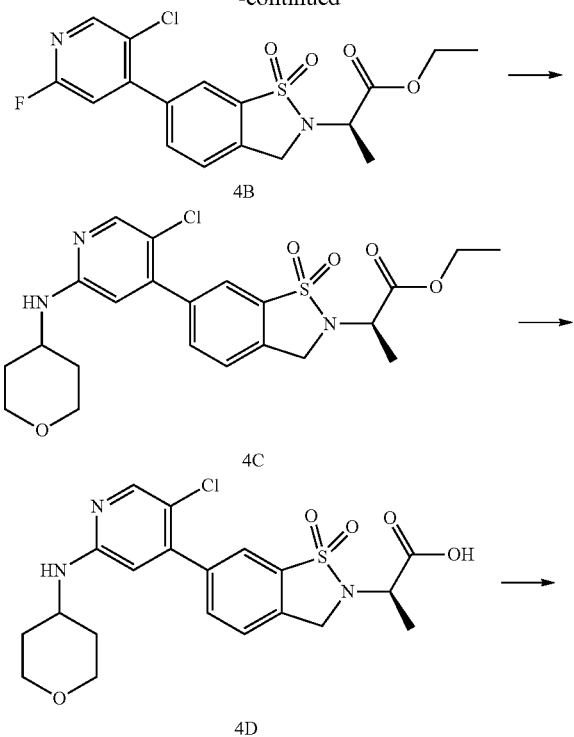

Compound 4B

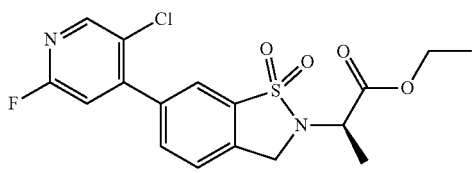

4B

Under the protection of nitrogen, compound 1E (100 mg, 252.99 μmol), compound 4A (97.69 mg, 379.48 μmol), Pd(dppf)Cl$_2$·CH$_2$Cl$_2$ (10.33 mg, 12.65 μmol) and sodium carbonate (53.63 mg, 505.97 μmol) were dissolved in dioxane (5 mL) and water (1 mL), and the reaction solution was stirred at 80° C. for 2 hours. After the reaction was completed, 0.5 mL of hydrochloric acid (2 mol) was added to reaction solution to quench the reaction, and the mixture was diluted with water (10 mL) and extracted with ethyl acetate (10 mL×2 times). The organic phases were combined and concentrated under reduced pressure to obtain a crude product, and the crude product was purified by silica gel column chromatography (eluting with petroleum ether:ethyl acetate=2:1) to obtain compound 4B. $^1$H NMR (400 MHz, CDCl$_3$) δ=8.27 (s, 1H), 7.83 (s, 1H), 7.65 (dd, 1H, J=1.4, 8.0 Hz), 7.49 (d, 1H, J=8.1 Hz), 6.90 (d, 1H, J=2.5 Hz), 4.90 (d, 1H, J=14.1 Hz), 4.5-4.6 (m, 2H), 4.1-4.2 (m, 2H), 1.6-1.6 (m, 3H), 1.2-1.3 (m, 3H). LCMS (ESI): m/z: 647.0 [M+1].

Compound 4C

4C

Under the protection of nitrogen, compound 4B (50 mg, 0.125 mmol), 4-aminotetrahydropyran (25.36 mg, 0.251 mmol) and DIEA (48.61 mg, 0.376 mmol, 65.51 μL) were dissolved in NMP (3 mL), and the mixture was stirred at 140° C. for 4 hours. The reaction solution was diluted with ethyl acetate (10 mL) and washed with 2 mol of hydrochloric acid (10 mL×1 time) aqueous solution. The organic phase was extracted with ethyl acetate (10 mL×2 times), and the combined organic phase was washed with brine (10 mL×1 time), and the organic phases were combined and concentrated under reduced pressure to obtain a crude product, and the crude product was purified by silica gel column chromatography (eluting with petroleum ether:ethyl acetate=10:1 to 4:1) to obtain compound 4C. $^1$H NMR (400 MHz, CDCl$_3$) δ=8.07 (s, 1H), 7.77 (s, 1H), 7.6-7.7 (m, 11H), 7.4-7.5 (m, 1H), 6.26 (s, 1H), 4.87 (d, 1H, J=13.9 Hz), 4.5-4.6 (m, 2H), 4.43 (br d, 1H, J=7.7 Hz), 4.1-4.2 (m, 2H), 3.9-4.0 (m, 2H), 3.7-3.9 (m, 1H), 3.48 (br t, 2H, J=10.8 Hz), 1.9-1.9 (m, 2H), 1.60 (d, 3H, J=7.3 Hz), 1.42 (br d, 2H, J=3.9 Hz), 1.2-1.2 (m, 3H). LCMS (ESI): m/z: 480.1 [M+1].

Compound 4D

4D

An aqueous (1 mL) solution of lithium hydroxide monohydrate (21.86 mg, 520.86 μmol) was added to a solution of compound 4C (50 mg, 104.17 μmol) in tetrahydrofuran (5 mL), and the reaction solution was stirred at 25° C. for 2 hours. After the reaction was completed, the reaction solution was concentrated under reduced pressure, and the pH was adjusted to 2 with 2 mol of hydrochloric acid aqueous solution, and then the solution was extracted with ethyl acetate (10 mL×3 times). The combined organic phase was filtered, and the filtrate was concentrated under reduced pressure to obtain a crude product of compound 4D. $^1$H NMR (400 MHz, CD$_3$OD) δ=8.06 (s, 1H), 7.86 (s, 1H), 7.79 (dd, 1H, J=1.4, 8.0 Hz), 7.6-7.7 (m, 1H), 6.59 (s, 1H), 4.94 (br s, 2H), 4.72 (d, 1H, J=14.5 Hz), 4.54 (q, 1H, J=73 Hz), 4.0-4.0 (m, 2H), 3.5-3.6 (m, 2H), 3.4-3.5 (m, 2H), 2.0-2.1 (m, 2H), 1.7-1.7 (m, 3H), 1.5-1.6 (m, 2H). LCMS (ESI): m/z: 452.0 [M+1].

Compound 4

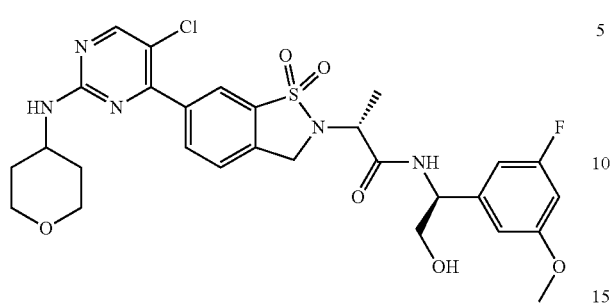

At 0° C., DIEA (34.32 mg, 265.53 μmol, 46.25 μL) was added to a solution of compound 4D (40 mg, 88.51 μmol) and (2S)-2-amino-2-(3-fluoro-5-methoxy-phenyl)ethanol (21.58 mg, 97.36 μmol) in dichloromethane (4 mL), and the mixture was stirred at 0° C. for 20 minutes, then HATU (40.39 mg, 106.21 μmol) was added and the mixture was continued to stir at 0° C. for 40 minutes. The pH of the reaction solution was adjusted to below 7 with hydrochloric acid (2 mol) aqueous solution, then the mixture was extracted with dichloromethane (10 mL×2 times), and then washed with water (10 mL×1 time). The combined organic phase was filtered, and the filtrate was concentrated under reduced pressure to obtain a crude product. The crude product was separated by preparative high performance liquid chromatography (formic acid system) to obtain a freebase of compound 4. ¹H NMR (400 MHz, CD₃OD) δ=8.06 (s, 1H), 7.88 (s, 1H), 7.80 (dd, 1H, J=1.3, 8.1 Hz), 7.69 (d, 1H, J=7.9 Hz), 6.77 (s, 1H), 6.70 (br d, 1H, J=9.9 Hz), 6.61 (td, 1H, J=2.2, 10.8 Hz), 6.57 (s, 1H), 4.9-5.0 (m, 2H), 4.6-4.7 (m, 2H), 3.9-4.1 (m, 3H), 3.81 (s, 3H), 3.7-3.8 (m, 2H), 3.5-3.6 (m, 2H), 2.0-2.1 (m, 2H), 1.61 (d, 3H, J=7.1 Hz), 1.56 (br dd, 2H, J=3.5, 11.8 Hz). LCMS (ESI): m/z: 619.0 [M+1].

Embodiment 5

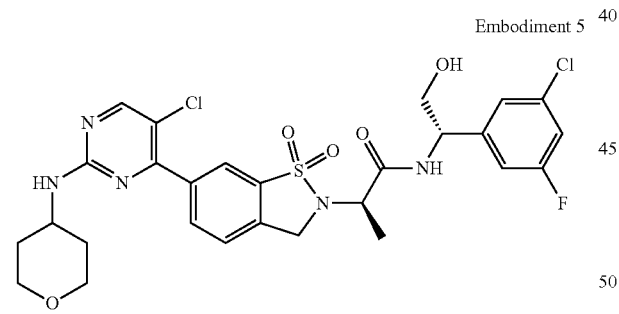

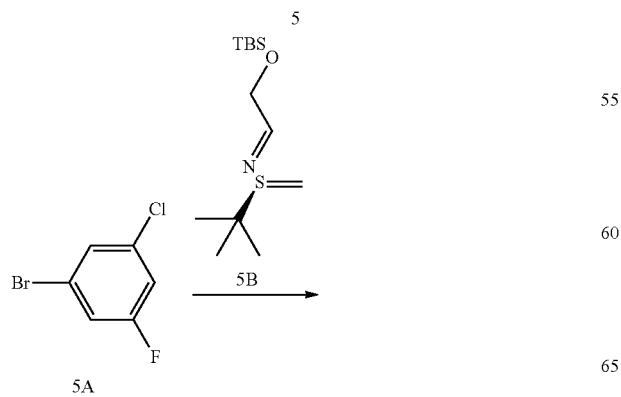

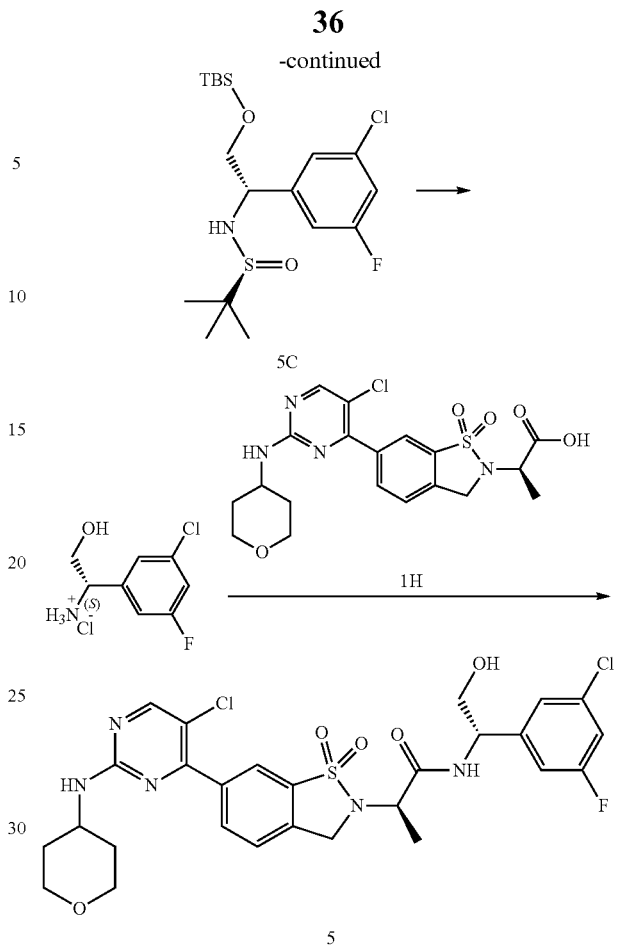

Compound 5C

Under the protection of nitrogen, a solution of compound 5A (1 g, 4.77 mmol) in tetrahydrofuran (4 mL) was slowly added to a solution of isopropyl magnesium bromide (1.3 mol, 3.75 mL) in tetrahydrofuran (12 mL) at −15° C. The mixture was stirred at −15° C. for 2 hours, then a solution of compound 5B (1.33 g, 4.78 mmol) in tetrahydrofuran (4 mL) was added thereto, and the reaction solution was continued to stir at −15° C. for 2 hours. After the reaction was completed, saturated ammonium chloride (20 mL) solution was added to quench the reaction solution, then the mixture was diluted with water (10 mL) and extracted with ethyl acetate (10 mL×2 times), and the organic phase was washed with brine (10 mL×1 time). The combined organic phase was concentrated under reduced pressure to obtain a crude product, and the crude product was separated by preparative high performance liquid chromatography (formic acid system) to obtain compound 5C. ¹H NMR (400 MHz, DMSO-d₆) δ=7.32 (br t, J=4.5 Hz, 2H), 7.23 (br d, J=9.5 Hz, 1H), 5.24 (d, J=5.9 Hz, 1H), 4.36 (q, J=6.2 Hz, 1H), 3.83 (dd, J=6.1, 9.9 Hz, 1H), 3.71 (dd, J=7.2, 10.0 Hz, 1H), 1.14-1.10 (m, 9H), 0.79 (s, 9H), −0.07 (d, J=12.1 Hz, 6H). LCMS (ESI): m/z: 408.4 [M+1].

Compound 5D

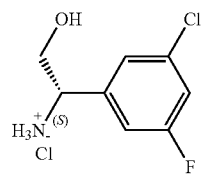

5D

Hydrochloric acid/dioxane (4 mol, 1.5 mL) was added to a solution of compound 5C (280 mg, 686.20 μmol) in dioxane (3 mL). The reaction solution was stirred at 25° C. for 0.5 hours. After the reaction was completed, the mixture was concentrated under reduced pressure to obtain a crude product of 5D, and the crude product was directly used in the next step.

Compound 5

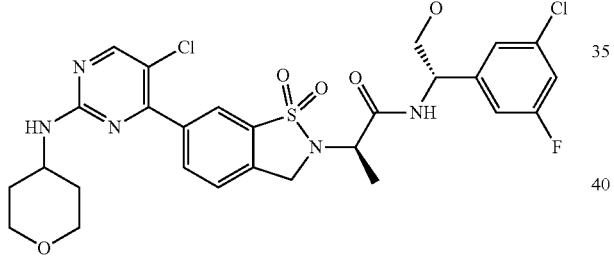

5

At 0° C., compound 5D (55 mg, 243.28 μmol) and DIEA (81.62 mg, 631.54 μmol, 110 μL) were added to a solution of compound 1H (70 mg, 154.56 μmol) in dichloromethane (3 mL), and the reaction solution was stirred at 0° C. for 5 minutes, and then HATU (79 mg, 207.77 μmol) was added thereto and the mixture was continued to react for 2 hours. After the reaction was completed, the reaction solution was diluted with water (10 mL) and extracted with dichloromethane (10 mL×3 times), washed with water (20 mL×1 time). The combined organic phase was filtered, and the filtrate was concentrated under reduced pressure to obtain a crude product. The crude product was separated by preparative high performance liquid chromatography (formic acid system) to obtain a freebase of compound 5. ¹H NMR (400 MHz, CD₃OD) δ=8.36 (s, 1H), 8.22 (s, 1H), 8.15 (dd, J=1.5, 8.0 Hz, 1H), 7.69 (d, J=8.2 Hz, 1H), 7.23 (s, 1H), 7.14-7.05 (m, 2H), 4.94 (br t, J=5.8 Hz, 2H), 4.69 (d, J=14.8 Hz, 1H), 4.63-4.57 (m, 1H), 4.09-3.93 (m, 3H), 3.79-3.69 (m, 2H), 3.58-3.48 (m, 2H), 1.99 (br dd, J=1.8, 12.8 Hz, 2H), 1.68-1.55 (m, 5H). LCMS (ESI): m/z: 624.4 [M+1].

Embodiment 6

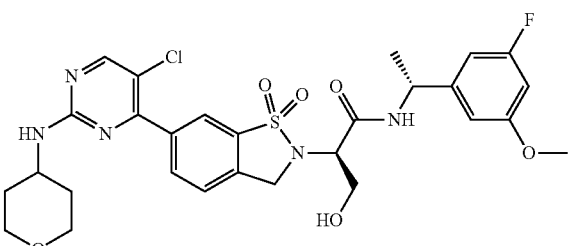

6

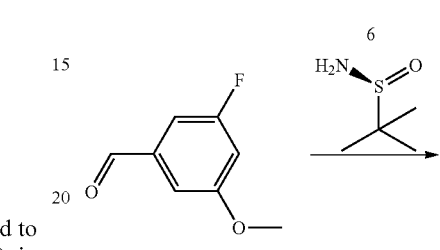

6A

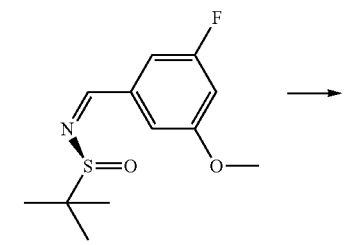

6B

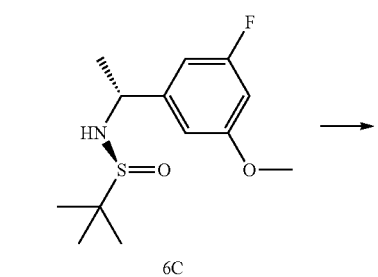

6C

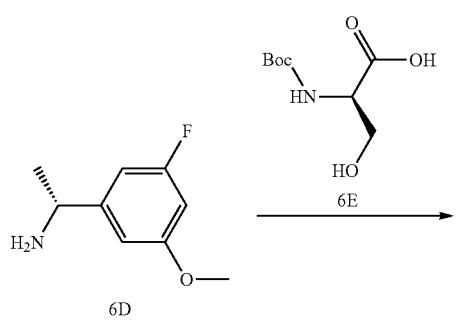

6D

6E

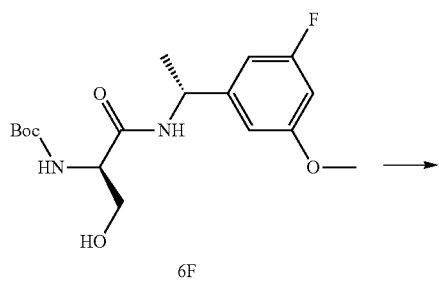

6F

-continued

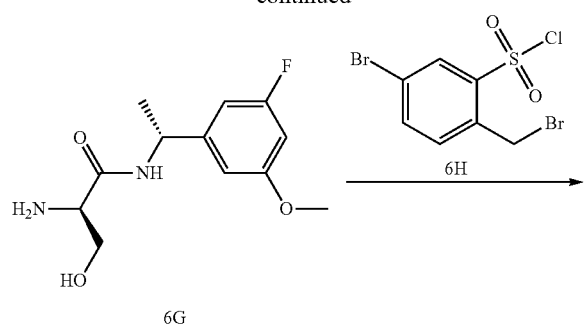

6G

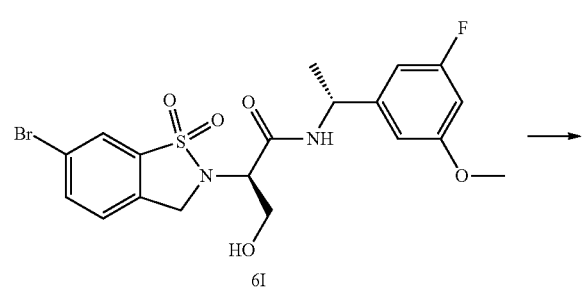

6I

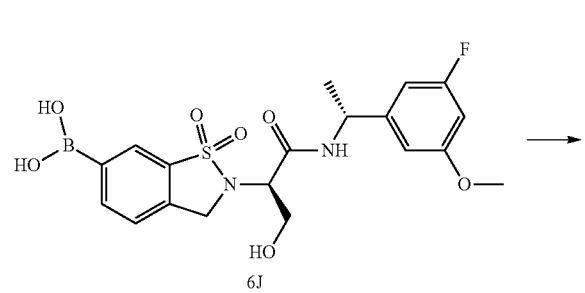

6J

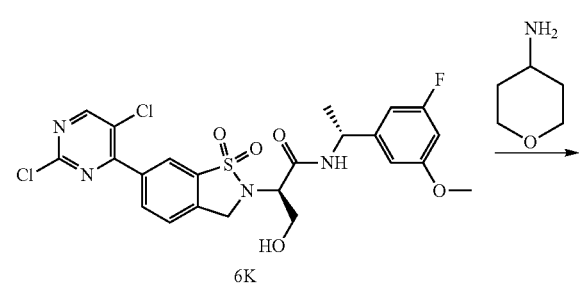

6K

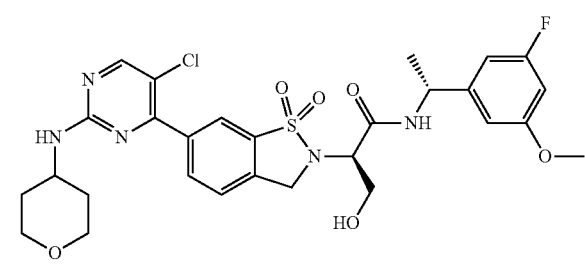

6

Compound 6B

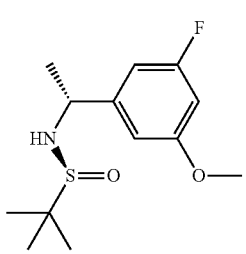

6B

Copper sulfate (12.94 g, 81.10 mmol, 12.45 mL) and (S)-2-methylpropyl-2-sulfenamide (4.72 g, 38.93 mmol) were added to a solution of compound 6A (5 g, 32.44 mmol) in dichloromethane (80 mL). The reaction solution was stirred at 50° C. for 16 hours. After the reaction was completed, the reaction solution was filtered and concentrated under reduced pressure to obtain a crude product. The crude product was purified by silica gel column chromatography (eluting with petroleum ether:ethyl acetate=40:1 to 10:1) to obtain compound 6B. $^1$H NMR (400 MHz, CDCl$_3$) δ=8.50 (d, J=1.0 Hz, 1H), 7.20-7.15 (m, 2H), 6.77 (td, J=2.3, 10.3 Hz, 1H), 3.86 (s, 3H), 1.27 (s, 9H).

Compound 6C

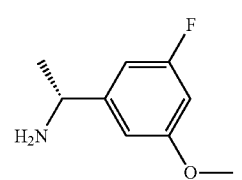

6C

At −78° C., under the protection of nitrogen, methyl magnesium bromide (3 mol, 17.1 mL) was added to a solution of compound 6B (5.3 g, 20.60 mmol) in tetrahydrofuran (100 mL), and the reaction solution was stirred at 15° C. for 16 hours. After the reaction was completed, saturated ammonium chloride (30 mL) solution was added to the reaction solution, and the organic phase was extracted with ethyl acetate (10 mL×2 times), and the combined organic phase was washed with brine (10 mL×1 time). The organic phases were combined and concentrated under reduced pressure to obtain a crude product, and the crude product was purified by silica gel column chromatography (eluting with petroleum ether:ethyl acetate=5:1 to 1:1) to obtain compound 6C. LCMS (ESI): m/z: 547.2 [M+1].

Compound 6D

6D

Hydrochloric acid/dioxane (4 mol, 36 mL) was added to a solution of compound 6C (3.67 g, 13.43 mmol) in dioxane (72 mL). The reaction solution was stirred at 20° C. for 1 hour. After the reaction was completed, the reaction solution was concentrated under reduced pressure to obtain a crude product of the hydrochloride of 6D, which was directly used in the next step.

Compound 6F

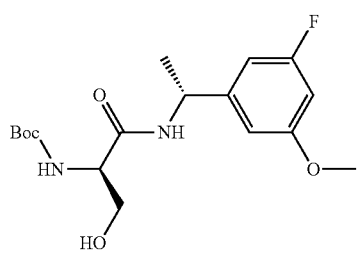

6F

Compound 6D hydrochloride (1.05 g, 5.11 mmol) and DIEA (2.37 g, 18.37 mmol, 3.2 mL) were added to a solution of compound 6E (900 mg, 4.39 mmol) in dichloromethane (20 mL) at 0° C. Then HATU (2.2 g, 5.79 mmol) was added thereto, and the reaction solution was stirred at 0° C. for 2 hours. After the reaction was completed, the reaction solution was diluted with water (50 mL), and the organic phase was extracted with dichloromethane (50 mL×3 times), and the combined organic phase was washed with brine (10 mL×1 time). The organic phases were combined and concentrated under reduced pressure to obtain a crude product, and the crude product was purified by silica gel column chromatography (eluting with dichloromethane:methanol=50:0 to 50:1) to obtain compound 6F. LCMS (ESI): m/z: 442.3 [M+1].

Compound 6G

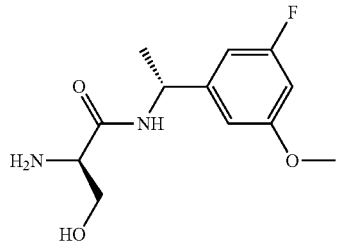

6G

At 0° C., trifluoroacetic acid (1.92 g, 16.88 mmol, 1.25 mL) was added to a solution of compound 6F (300 mg, 841.78 μmol) in dichloromethane (5 mL). The reaction solution was stirred at 20° C. for 3 hours. After the reaction was completed, the mixture was concentrated under reduced pressure to obtain a crude product of 6G, and the crude product was directly used in the next step. LCMS (EST): m/z: 257.1 [M+1].

Compound 6I

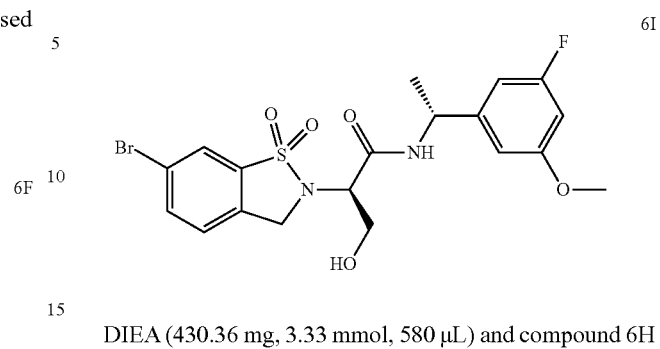

6I

DIEA (430.36 mg, 3.33 mmol, 580 μL) and compound 6H (435 mg, 1.25 mmol) were added to a solution of compound 6G (310 mg, 837.17 μmol) in acetonitrile (5 mL). The reaction solution was stirred at 80° C. for 16 hours. After the reaction was completed, the reaction solution was diluted with water (20 mL), and then the organic phase was extracted with dichloromethane (20 mL×3 times), and the combined organic phase was washed with brine (10 mL×1 time). The organic phases were combined and concentrated under reduced pressure to obtain a crude product, and the crude product was purified by silica gel column chromatography (eluting with dichloromethane:methanol=10:1) to obtain compound 6I. $^1$H NMR (400 MHz, DMSO-$d_6$) δ=8.70 (br d, J=7.9 Hz, 1H), 8.20 (d, J=1.6 Hz, 1H), 7.91 (dd. J=1.8, 8.3 Hz, 1H), 7.60 (d, J=8.3 Hz, 1H), 6.79-6.60 (m, 3H), 5.24 (t, J=5.4 Hz, 1H), 4.94 (d, J=15.0 Hz, 1H), 4.89-4.83 (m, 1H), 4.61 (d, J=15.0 Hz, 1H), 4.34 (t, J=6.7 Hz, 1H), 3.84-3.70 (m, 5H), 1.32 (d, J=7.0 Hz, 3H). LCMS (ESI): m/z: 489.0 [M+1].

Compound 6J

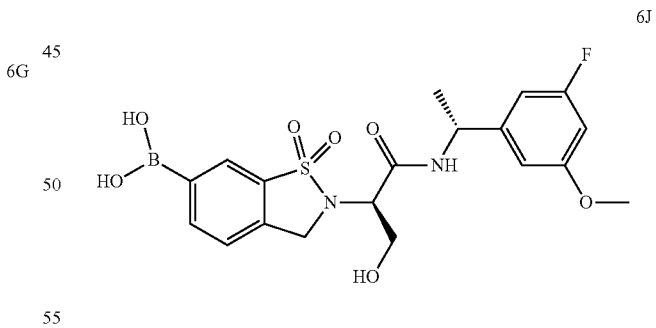

6J

Under the protection of nitrogen, compound 6I (130 mg, 266.75 μmol), bis(pinacolato)diboron, Pd(dppf)Cl$_2$·CH$_2$Cl$_2$ (12 mg, 14.69 μmol), potassium tert-butoxide (80 mg, 815.16 μmol) were dissolved in dioxane (3 mL), and the reaction solution was stirred at 90° C. for 1 hour. After the reaction was completed, the reaction solution was concentrated under reduced pressure to obtain a crude product of compound 6J, and the crude product was directly used in the next step. LCMS (ESI): m/z: 453.1 [M+1].

Compound 6K

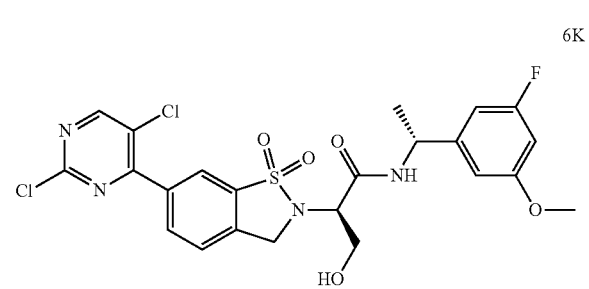

Under the protection of nitrogen, compound 6J (140 mg, 261.97 μmol), 2,4,5-trichloropyrimidine (114 mg, 621.51 μmol, 56.29 μL), Pd(PPh$_3$)$_4$ (30 mg, 25.96 μmol) and sodium carbonate (70 mg, 660.44 μmol) were dissolved in dioxane (4 mL) and water (1 mL), and the reaction solution was stirred at 100° C. for 1 hour. After the reaction was completed, the reaction solution was concentrated under reduced pressure, and the filtrate was diluted with water (20 mL) and extracted with ethyl acetate (20 mL×3 times). The organic phases were combined and concentrated under reduced pressure to obtain a crude product, and the crude product was purified by silica gel column chromatography (eluting with petroleum ether:ethyl acetate=1:1) to obtain compound 6K. LCMS (ESI): m/z: 555.1 [M+1].

Compound 6

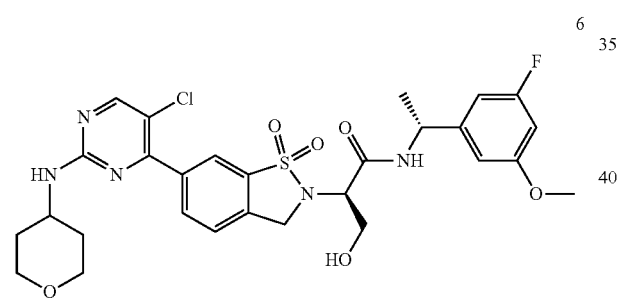

DIEA (44.52 mg, 344.48 μmol, 60 μL) and 4-aminotetrahydropyran (40 mg, 395.47 μmol) were added to a solution of compound 6K (70 mg, 126.03 μmol) in dioxane (3 mL). The reaction solution was stirred at 90° C. for 16 hours. The reaction solution was diluted with water (20 mL) and extracted with ethyl acetate (15 mL×3 times). The organic phase was washed with brine (30 mL×1 time), and the organic phases were combined, filtered, and concentrated under reduced pressure to obtain a crude product. The crude product was separated by preparative high performance liquid chromatography (formic acid system) to obtain a freebase of compound 6. $^1$H NMR (400 MHz, CD$_3$OD) δ=8.37 (s, 1H), 8.22 (d, J=1.0 Hz, 1H), 8.15 (dd, J=1.6, 8.1 Hz, 1H), 7.69 (d, J=8.1 Hz, 1H), 6.75 (s, 1H), 6.71-6.65 (m, 1H), 6.54 (td, J=2.2, 10.7 Hz, 1H), 5.04 (d, J=14.8 Hz, 1H), 5.00-4.92 (m, 1H), 4.76 (d, J=14.9 Hz, 1H), 4.47 (t, J=6.6 Hz, 1H), 4.08-3.93 (m, 5H), 3.79 (s, 3H), 3.53 (dt, J=1.9, 11.6 Hz, 2H), 1.99 (br dd, J=2.2, 12.4 Hz, 2H), 1.68-1.56 (m, 2H), 1.44 (d, J=7.0 Hz, 3H). LCMS (ESI): m/z: 620.5 [M+1].

Embodiment 7

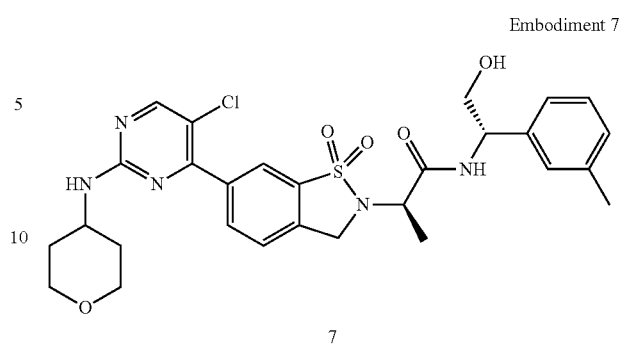

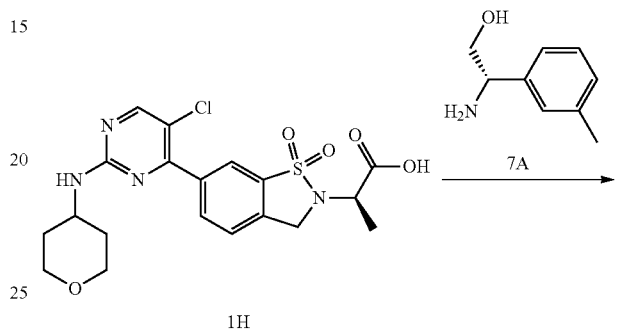

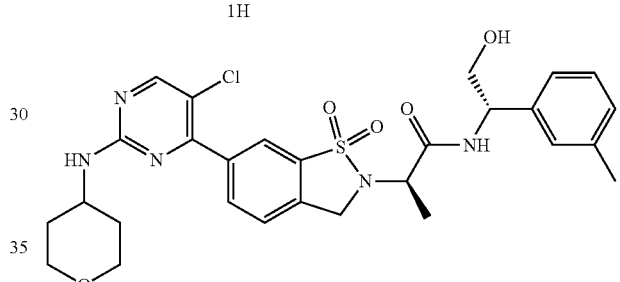

Compound 7

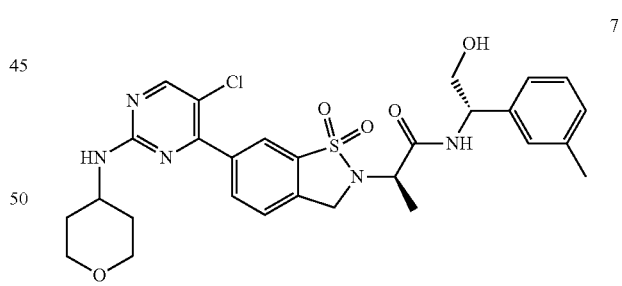

At 0° C., compound 7A (65.78 mg, 350.52 μmol) and DIEA (118.72 mg, 918.60 μmol, 160 μL) were added to a solution of compound 1H (100 mug, 220.79 μmol) in dichloromethane (3 mL), and the reaction solution was stirred at 0° C. for 10 minutes, and then HATU (112 mg, 294.56 μmol) was added thereto and the mixture was continued to stir for 2 hours. The reaction solution was diluted with water (10 mL) and extracted with dichloromethane (10 mL×3 times). The organic phase was washed with brine (20 mL×1 time), and the combined organic phase was filtered, and the filtrate was concentrated under reduced pressure to obtain a crude product. The crude product was separated by preparative high performance liquid chromatography (formic acid system) to obtain a freebase of compound 7. $^1$H NMR (400 MHz, CD$_3$OD) δ=8.36 (s, 1H), 8.22 (d, J=1.1 Hz, 1H), 8.15 (dd, J=1.6, 8.1 Hz, 1H), 7.69 (d, J=8.4 Hz, 1H), 7.25-7.19 (m, 1H), 7.16 (s, 1H), 7.10 (dd, J=7.6, 15.3 Hz, 2H), 4.96-4.93 (m, 1H), 4.93-4.89 (m, 11H), 4.69 (d, J=14.8 Hz, 1H), 4.59 (q, J=7.0 Hz, 1H), 4.10-3.93 (m, 3H), 3.78-3.66 (m, 2H), 3.53 (dt, J=1.9, 11.7 Hz, 2H) 2.33 (s, 3H), 1.99 (br dd, J=1.9, 12.6 Hz, 2H), 1.68-1.55 (m, 5H). LCMS (ESI): m/z: 586.1 [M+1].

Embodiment 8

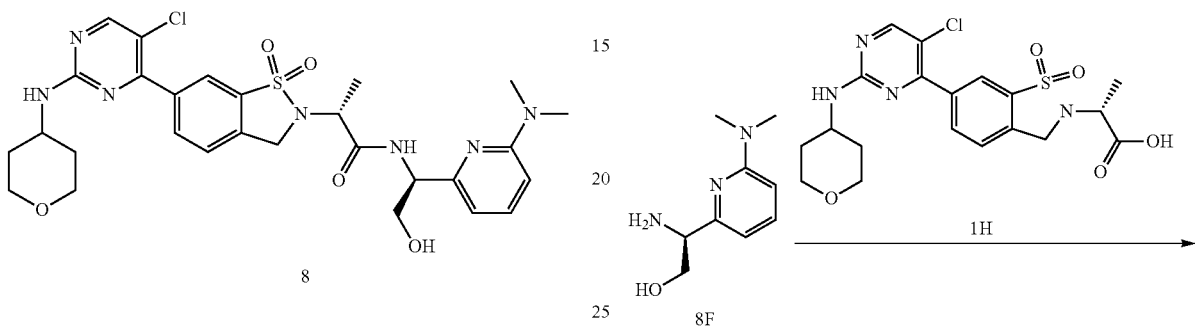

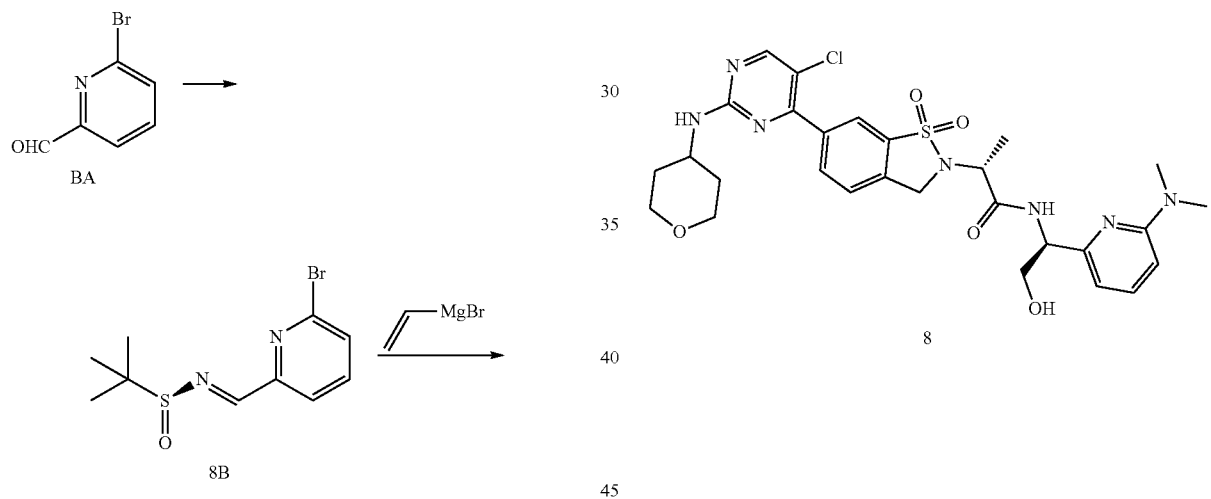

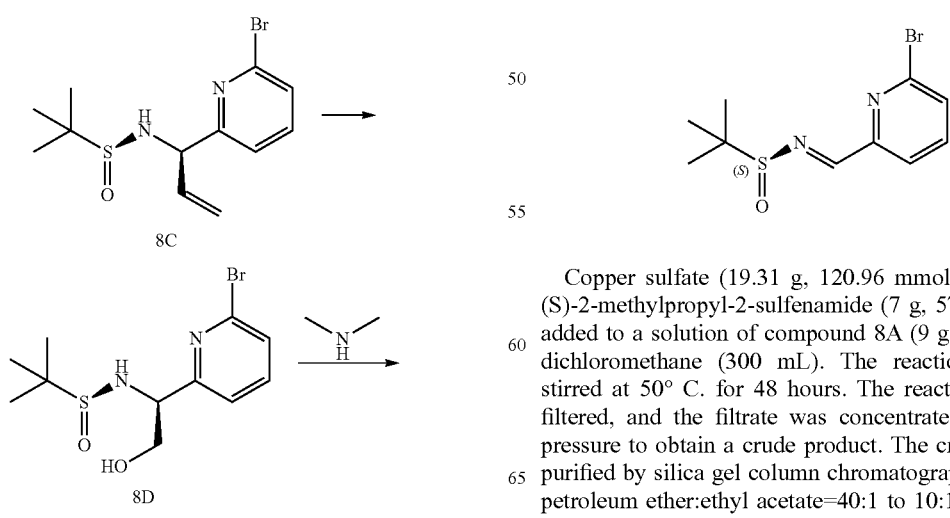

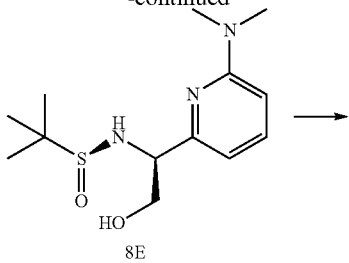

Compound 8B

Copper sulfate (19.31 g, 120.96 mmol, 18.57 mL) and (S)-2-methylpropyl-2-sulfenamide (7 g, 57.76 mmol) were added to a solution of compound 8A (9 g, 48.39 mmol) in dichloromethane (300 mL). The reaction solution was stirred at 50° C. for 48 hours. The reaction solution was filtered, and the filtrate was concentrated under reduced pressure to obtain a crude product. The crude product was purified by silica gel column chromatography (eluting with petroleum ether:ethyl acetate=40:1 to 10:1) to obtain compound 8B.

Compound 8C

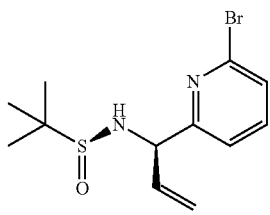

Compound 8E

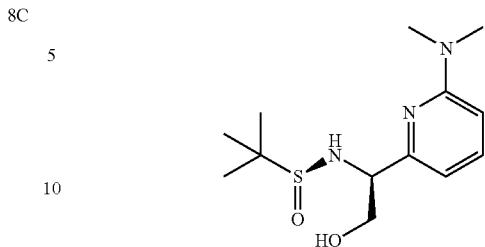

At −78° C., under the protection of nitrogen, a solution of compound 8B (3 g, 10.37 mmol) in tetrahydrofuran (20 ml-) was added to a solution of allyl magnesium bromide (1 mol, 21.78 mL) in tetrahydrofuran (40 mL), and the reaction solution was stirred at −78° C. for 1 hour. After the reaction was completed, saturated ammonium chloride (30 mL) solution was added thereto to quench the mixture, then the mixture was diluted with water (50 mL) and extracted with ethyl acetate (50 mL×3 times), and the organic phase was washed with brine (50 mL×1 time). The combined organic phase was concentrated under reduced pressure to obtain a crude product, and the crude product was separated by preparative high performance liquid chromatography (formic acid system) to obtain compound 8C. LCMS (ESI): m/z: 319.0 [M+1].

Compound 8D (100.00 mg, 311.30 μmol) was dissolved in dimethylamine (2 mol, 3 mL) and reacted at 120° C. for 4 hours under microwave. After the reaction was completed, the reaction solution was concentrated under reduced pressure to obtain a crude product, and the crude product was purified by silica gel column chromatography (eluting with dichloromethane:methanol=10:1) to obtain compound 8E. LCMS (ESI): m/z: 286.1 [M+1].

Compound 8F

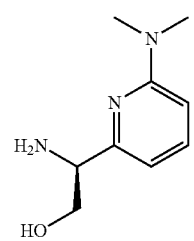

Hydrochloric acid/dioxane (4 mol, 1 mL) was added to a solution of compound 8E (90 mg, 315.34 μmol) in dioxane (2 mL). The reaction solution was stirred at 25° C. for 1 hour. After the reaction was completed, the reaction solution was concentrated under reduced pressure to obtain a crude product of the hydrochloride of compound 8F, which was directly used in the next step. $^1$H NMR (400 MHz, DMSO-$d_6$) δ=8.33 (br s, 3H), 7.57 (br t, J=7.9 Hz, 1H), 6.73-6.58 (m, 2H), 4.26 (br d, J=1.6 Hz, 1H), 3.84-3.66 (m, 2H), 3.07 (s, 6H).

Compound 8D

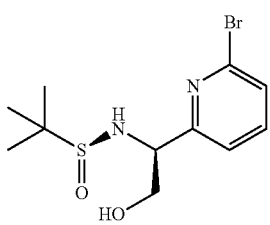

At −78° C., compound 8C (1 g, 3.15 mmol) was dissolved in dichloromethane (10 mL) and methanol (10 mL) under the condition of ozone (3.15 mmol, 15 psi), and sodium borohydride (240.00 mg, 6.34 mmol) was added to the reaction solution, and then the mixture was stirred at −78° C. for 3 hours. After the reaction was completed, saturated ammonium chloride (30 mL) solution was added to quench the reaction solution, and the mixture was diluted with water (30 mL), extracted with ethyl acetate (50 mL×2 times), and the organic phase was washed with brine (80 mL×1 time). The organic phases were combined and concentrated under reduced pressure to obtain a crude product, and the crude product was purified by silica gel column chromatography (eluting with petroleum ether:ethyl acetate=3:1) to obtain compound 8D. LCMS (ESI): m/z: 337.0 [M+1].

Compound 8

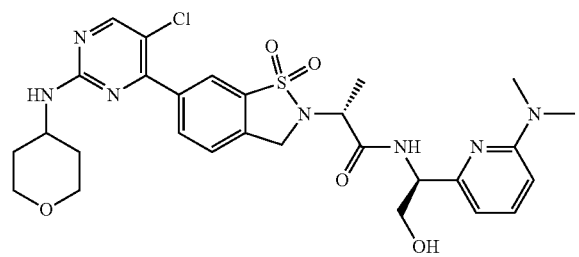

Compound 8F (54.00 mg, 248.06 μmol, HCl) and DIEA (118.72 mg, 918.60 μmol, 160 μL) were added to a solution of compound 1H (100 mg, 220.79 μmol) in dichloromethane (3 mL) at 0° C. After the reaction solution was stirred for 10 minutes, HATU (110 mg, 289.30 μmol) was added thereto, and the reaction solution was continued to stir for 2 hours. The reaction solution was diluted with water (10 mL) and extracted with dichloromethane (10 mL×3 times). The organic phase was washed with brine (20 mL×1), and then the organic phases were combined and filtered, and the filtrate was concentrated under reduced pressure to obtain a crude product, and the crude product was separated by preparative high performance liquid chromatography (formic acid system), and then a freebase of compound 8 was obtained by chiral separation method (0.1% ammonia water-methanol system, retention time of 3.6 minutes, ee value: 100%). $^1$H NMR (400 MHz, MeOH-d$_4$) δ=8.37 (s, 1H), 8.22 (d, J=1.1 Hz, 1H), 8.16 (dd, J=1.6, 8.1 Hz, 1H), 7.70 (d, J=8.1 Hz, 1H), 7.45 (dd, J=7.3, 8.5 Hz, 1H), 6.56 (d, J=7.2 Hz, 1H), 6.49 (d, J=8.4 Hz, 1H), 4.92-4.89 (m, 1H), 4.81-4.65 (m, 2H), 4.60 (q, J=7.1 Hz, 1H), 4.12-3.93 (m, 3H), 3.80 (dq, J=5.6, 10.9 Hz, 2H), 3.53 (dt, J=1.9, 11.6 Hz, 2H), 2.91 (s, 6H), 2.04-1.95 (m, 2H), 1.66-1.56 (m, 5H). LCMS (ESI): m/z: 616.3 [M+1].

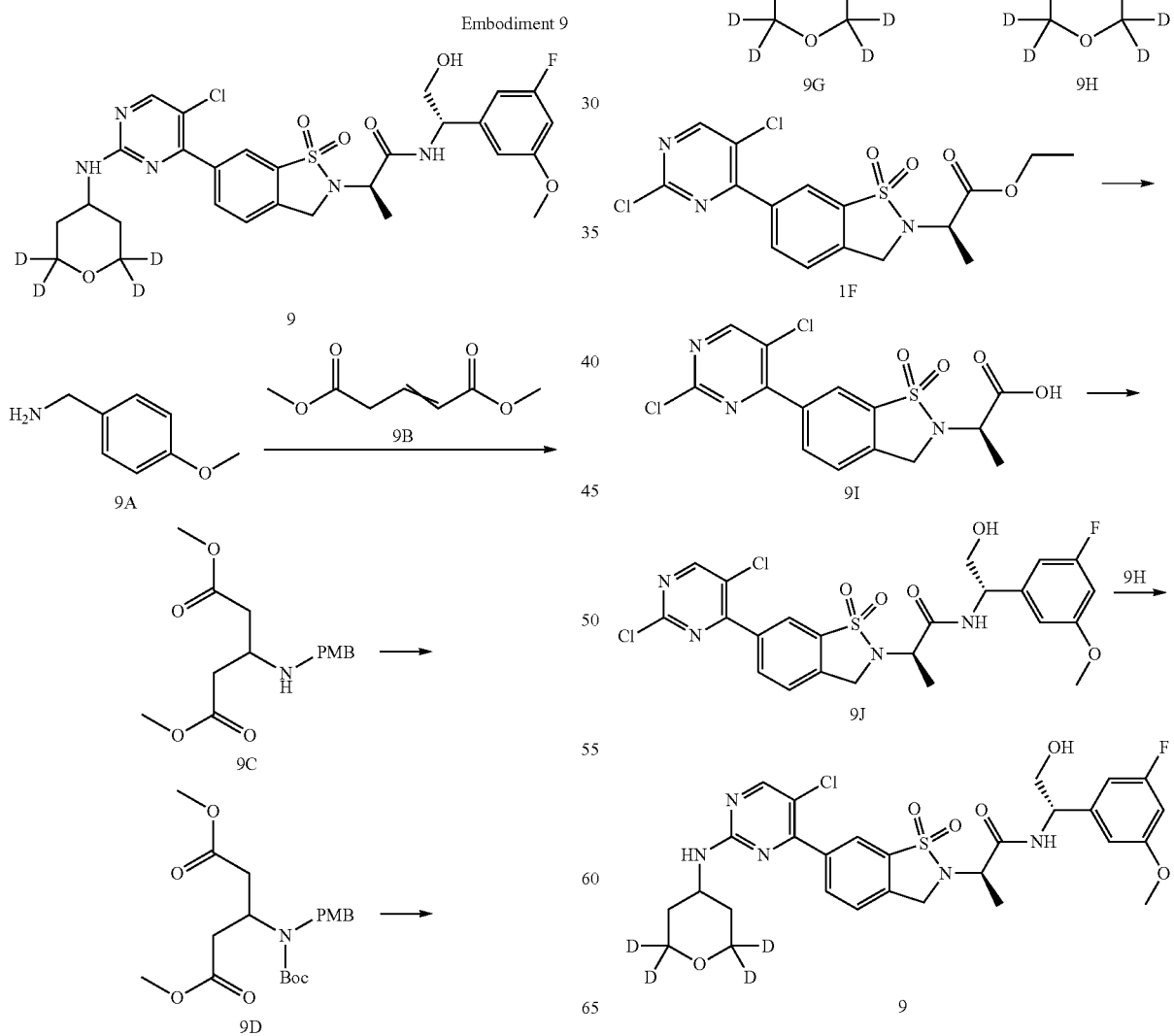

Embodiment 9

Compound 9C

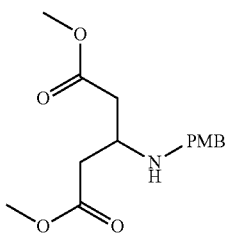

9C

Compound 9A (2 g, 14.58 mmol, 1.89 mL) was dissolved in methanol (2 mL), and compound 9B (2.08 g, 13.13 mmol, 1.85 mL) was added, and the mixture was stirred at 10° C. for 16 hours. After the reaction was completed, the mixture was concentrated under reduced pressure to obtain a crude product, and the crude product was purified by silica gel column chromatography (eluting with petroleum ether:ethyl acetate=4:1 to 2:1) to obtain compound 9C. $^1$H NMR (400 MHz, CDCl$_3$) δ=7.24 (d, J=8.5 Hz, 2H), 6.92-6.79 (m, 2H), 3.80 (s, 3H), 3.75 (s, 2H), 3.69 (s, 6H), 3.44 (quin, J=6.2 Hz, 1H), 2.59 (d, J=6.3 Hz, 4H).

Compound 9D

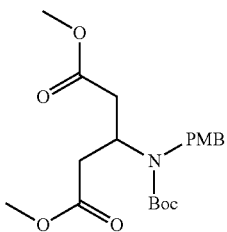

9D (Boc)$_2$O (2.53 g, 11.57 mmol, 2.66 mL) and DIEA (1.77 g, 13.68 mmol, 2.38 mL) were added to a solution of compound 9C (2.85 g, 9.65 mmol) in tetrahydrofuran (30 mL). The mixture was stirred at 10° C. for 16 hours. After the reaction was completed, the mixture was concentrated under reduced pressure to obtain a crude product, and the crude product was purified by silica gel column chromatography (eluting with petroleum ether:ethyl acetate=10:1 to 5:1) to obtain compound 9D, 1H NMR (400 MHz, CDCl$_3$) δ=7.22 (br s, 28), 6.85 (d, J=8.6 Hz, 2H), 4.42 (br s, 28), 4.35-4.20 (m, 18), 3.85-3.73 (m, 3H), 3.61 (s, 68), 2.86-2.50 (m, 4H), 1.50 (br d, J=16.0 Hz, 9H). LCMS (ESI): m/z: 296.1 [M+1].

Compound 9E

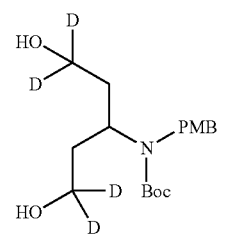

9E

Under the protection of nitrogen, LiAlD$_4$ (910 mg, 23.98 mmol, 1.24 mL) was added to a solution of compound 9D (3.16 g, 7.99 mmol) in tetrahydrofuran (35 mL). The reaction solution was stirred at 0° C. for 20 minutes. After the reaction was completed, 15% sodium hydroxide (0.91 mL) aqueous solution was added to the mixture to quench, and then the mixture was filtered, and the filtrate was concentrated under reduced pressure to obtain a crude product of 9E, and the crude product was directly used in the next step. $^1$H NMR (400 MHz, CDCl$_3$) δ=7.21 (br d, J=7.4 Hz, 2H), 6.88-6.82 (m, 2H), 4.52-4.32 (m, 1H), 4.26 (br s, 2H), 3.80 (s, 3H), 1.67 (br d, J=6.9 Hz, 4H), 1.50-1.46 (m, 9H).

Compound 9F

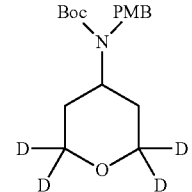 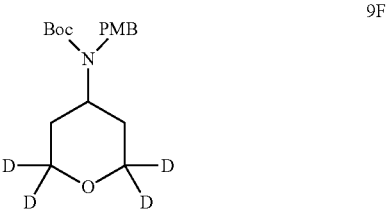

9F

Potassium tert-butoxide (975.00 mg, 8.69 mmol) was added to a solution of compound 9E (1.5 g, 4.37 mmol) in tetrahydrofuran (20 mL), and the mixture was stirred for 15 minutes, then MsCl (555.00 mg, 4.85 mmol, 375.00 μL) and potassium tert-butoxide (495.00 mg, 4.41 mmol) were added thereto. The mixture was stirred at 25° C. for 2 hours, and after the reaction was completed, saturated ammonium chloride (10 mL) solution was added to the reaction solution, then the mixture was extracted with ethyl acetate (50 mL×3 times). The organic phases were combined and concentrated under reduced pressure to obtain a crude product, and the crude product was purified by silica gel column chromatography (eluting with petroleum ether:ethyl acetate=10:1 to 5:1) to obtain compound 9F. $^1$H NMR (400 MHz, DMSO-d$_6$) δ=7.15 (d, J=8.7 Hz, 2H), 6.87 (d, J=8.7 Hz, 2H), 4.29 (br s, 2H), 4.08-3.75 (m, 1H), 3.71 (s, 3H), 1.63 (br t, J=12.3 Hz, 2H), 1.46-1.30 (m, 11H)

Compound 9G

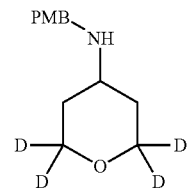

9G

Hydrochloric acid/dioxane (4 mol, 2 mL) was added to a solution of compound 9F (560 mg, 1.72 mmol) in methanol (2 mL). The reaction solution was stirred at 25° C. for 2 hours. After the reaction was completed, the reaction solution was poured into methyl tert-butyl ether (10 mL), filtered to obtain a filter cake. The filter cake was dissolved in water (10 mL), and the pH was adjusted to 11 with sodium hydroxide (2 mol) aqueous solution, and then the mixture was extracted with ethyl acetate (10 mL×2 times). The combined organic phase was concentrated under reduced pressure to obtain a crude product of 9G, and the crude product was directly used in the next step. $^1$H NMR (400

MHz, CDCl₃) δ=7.25 (d, J=8.6 Hz, 2H), 6.90-6.83 (m, 2H), 3.81 (s, 3H), 3.78 (s, 2H), 2.73 (tt, J=4.1, 10.5 Hz, 1H), 1.84 (dd. J=4.1, 13.3 Hz, 2H), 1.45 (br d, J=11.7 Hz, 2H).

Compound 9H

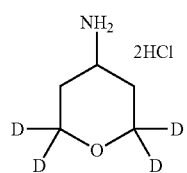

9H

Palladium/carbon (50 mg, 10% purity) was added to a solution of compound 9G (150 mg, 665.72 μmol) in methanol (10 mL). Under the condition of hydrogen (0.8 Mpa), the reaction solution was stirred at 50° C. for 16 hours. After the reaction was completed, the mixture was filtered, and the filtrate was concentrated under reduced pressure and then dissolved in methanol (1 mL). The pH of the mixture was adjusted to 1 with hydrochloric acid/dioxane (4 mol), and then methyl tert-butyl ether (5 mL) was added to the mixture and filtered to obtain a crude product of 9H, and the crude product was directly used in the next step. ¹H NMR (400 MHz, DMSO-d₆) δ=8.11 (br s, 2H), 3.29-3.15 (m, 1H), 1.82 (dd, J=4.2, 13.0 Hz, 2H), 1.52 (br t, J=12.0 Hz, 2H).

Compound 9I

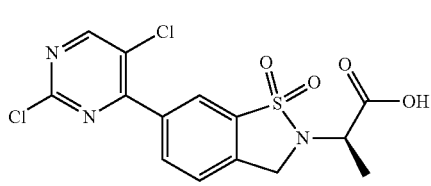

9I

Lithium hydroxide monohydrate (472.00 mg, 11.25 mmol) was added to a solution of compound 1F (1.18 g, 2.83 mmol) in tetrahydrofuran (5 mL) and water (5 mL). The reaction solution was stirred at 0° C. for 1 hour. After the reaction was completed, water (10 mL) was added to the reaction solution, then the mixture was extracted with ethyl acetate (10 mL×1 time). The pH of the aqueous phase was adjusted to 2 with hydrochloric acid (2 mol), and the mixture was extracted with dichloromethane (10 mL×2 times). The organic phases were combined, filtered, and concentrated under reduced pressure to obtain a crude product of 9I, and the crude product was directly used in the next step. ¹H NMR (400 MHz, CDCl₃) δ=8.73 (s, 1H), 8.42 (d, J=1.3 Hz, 1H), 8.20 (dd, J=1.5, 8.1 Hz, 1H), 7.59 (d, J=8.1 Hz, 11H), 4.94-4.86 (m, 1H), 4.70-4.60 (m, 2H), 1.72 (d, J=7.3 Hz, 3H). LCMS (ESI): m/z: 387.9 [M+1].

Compound 9J

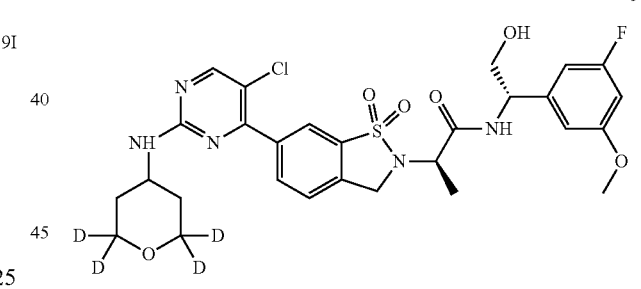

9J

At 0° C., HATU (585.85 mg, 1.54 mmol), (2S)-2-amino-2-(3-fluoro-5-methoxy-phenyl)ethanol (280 mg, 1.26 mmol) and DIEA (406.27 mg, 3.14 mmol, 547.54 μL) were added to a solution of compound 9I (450 mg, 1.04 mmol, 89.44% purity) in dichloromethane (10 mL). The reaction solution was stirred at 15° C. for 30 minutes. The reaction solution was diluted with water (2 ml) and extracted with ethyl acetate (2 mL×3 times). The organic phases were combined and filtered, and the filtrate was concentrated under reduced pressure to obtain a crude product. The crude product was purified by silica gel column chromatography (eluting with petroleum ether:ethyl acetate=2:1) to obtain compound 9F. ¹H NMR (4004 Hz, CDCl₃) δ=8.68-8.64 (m, 2H), 8.39-8.32 (m, 2H), 8.19-8.12 (m, 2H), 7.56-7.44 (m, 21H), 6.60-6.24 (m, 7H), 4.99-4.90 (m, 2H), 4.74-4.67 (m, 1H), 4.56-4.50 (m, 3H), 3.70 (s, 3H), 1.97-1.92 (m, 3H), 1.57-1.50 (m, 7H). LCMS (ESI): m/z: 555.0 [M+1].

Compound 9

9

DIEA (83.85 mg, 648.75 μmol, 113 μL) was added to a solution of compound 9J (90 mg, 162.04 μmol) and 9H (70 mg, 393.05 μmol) in dioxane (3 mL). The reaction solution was stirred at 100° C. under sealed tank conditions for 16 hours. The reaction solution was diluted with water (5 mL) and extracted with ethyl acetate (2 mL×3 times), and the organic phases were combined, dried, and then filtered and concentrated under reduced pressure to obtain a crude product, and the crude product was separated by preparative high performance liquid chromatography (formic acid system) to obtain a freebase of compound 9. ¹H NMR (400 MHz, MeOH-d₄) δ=8.36 (s, 1H), 8.22 (s, 1H), 8.15 (dd, J=1.5, 8.1 Hz, 1H), 7.69 (d, J=8.3 Hz, 1H), 6.75 (s, 1H), 6.68 (br d, J=9.3 Hz, 1H), 6.59 (td, J=2.2, 10.7 Hz, 1H), 4.92 (d, J=7.1 Hz, 1H), 4.83-4.79 (m, 1H), 4.70 (d, J=15.0 Hz, 1H), 4.59 (q, J=7.1 Hz, 1H), 4.10-3.97 (m, 1H), 3.79 (s, 3H), 3.76-3.69 (m, 2H), 1.98 (dd, J=4.1, 13.4 Hz, 2H), 1.63-1.55 (m, 5H). LCMS (ESI): m/z: 624.0 [M+1].

Embodiment 10

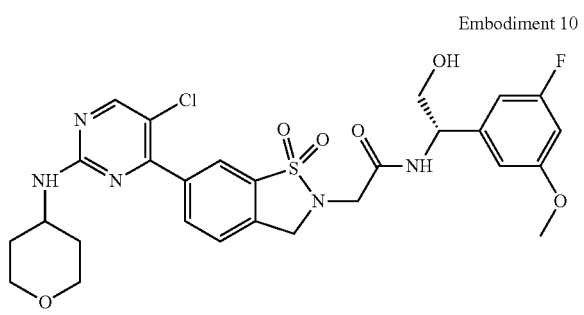

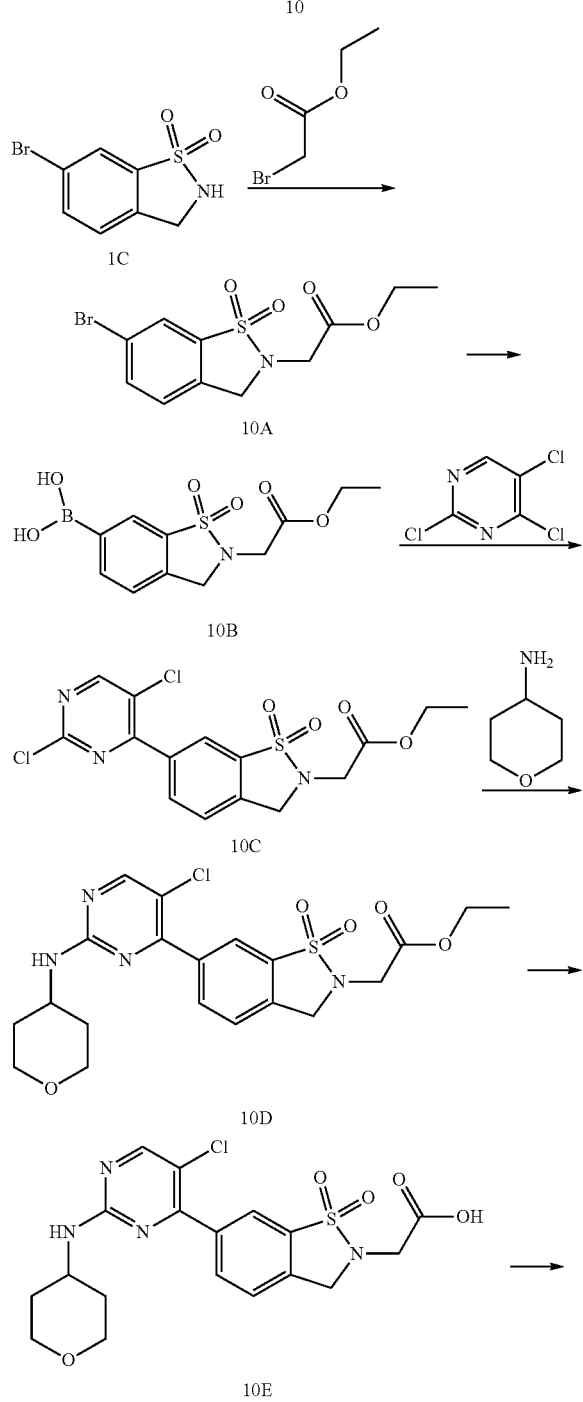

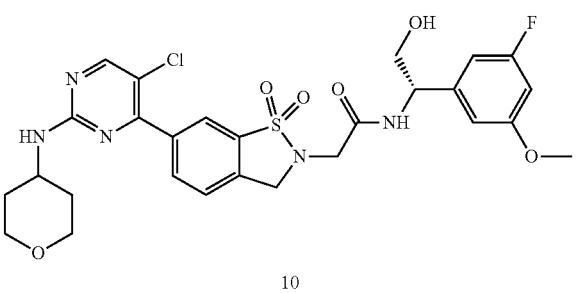 [SMILES: COc1cc(F)cc([C@@H](CO)NC(=O)CN2Cc3ccc(-c4nc(NC5CCOCC5)ncc4Cl)cc3S2(=O)=O)c1]

Compound 10A

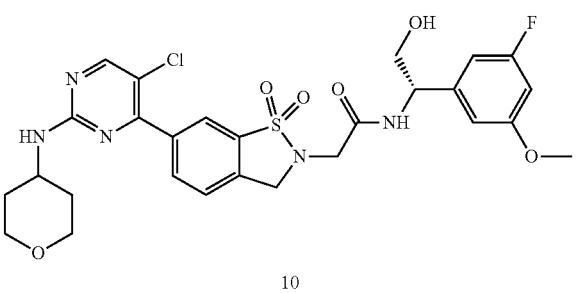 [SMILES: COc1cc(F)cc([C@@H](CO)NC(=O)CN2Cc3ccc(-c4nc(NC5CCOCC5)ncc4Cl)cc3S2(=O)=O)c1]

Under the protection of nitrogen, compound 1C (400 mg, 1.61 mmol), ethyl ethyl-2-bromoacetate (404 ng, 2.42 mmol, 267.55 µL) and potassium carbonate (450 mg, 3.26 mmol) were dissolved in DMF (6 mL), and the reaction solution was stirred at 25° C. for 16 hours. After the reaction was completed, the mixture was diluted with water (30 mL) and extracted with ethyl acetate (20 mL×3 times). The organic phase was washed with brine (50 mL×1 time), and the organic phases were combined and concentrated under reduced pressure to obtain a crude product, and the crude product was purified by silica gel column chromatography (eluting with petroleum ether:ethyl acetate=10:1 to 5:1) to obtain compound 10A. $^1$H NMR (400 MHz, CDCl$_3$) δ=7.96 (d, J=1.6 Hz, 1H), 7.74 (dd, J=1.8, 8.3 Hz, 1H), 7.30 (d, J=8.2 Hz, 1H), 4.59 (s, 2H), 4.24 (q, J=7.1 Hz, 2H), 4.08 (s, 2H), 1.30 (t, J=7.2 Hz, 3H). LCMS (ESI): m/z: 320.0 [M+1].

Compound 10B

Under the protection of nitrogen, compound 10A (360 mg, 1.08 mmol), bis(pinacolato)diboron (410 mg, 161 mmol), Pd(dppf)Cl$_2$·CH$_2$Cl$_2$ (45 mg, 55.10 µmol) and potassium acetate (320 mg, 3.26 mmol) were dissolved in dioxane (4 mL), and the reaction solution was stirred at 90° C. for 1 hour. The reaction solution was concentrated under reduced pressure to obtain a crude product of compound 10B, and the crude product was directly used in the next step. LCMS (ESI): m/z: 300.1 [M+1].

Compound 10C

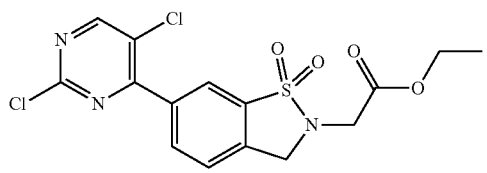

Under the protection of nitrogen, compound 10B (322 mg, 1.08 mmol), 2,4,5-trichloropyrimidine (355 mg, 1.94 mmol), Pd(PPh$_3$)$_4$ (62 mg, 53.65 μmol) and sodium carbonate (235 mg, 2.22 mmol) were dissolved in dioxane (6 mL) and water (1.5 mL), and the reaction solution was stirred at 90° C. for 2 hours. After the reaction was completed, the reaction solution was filtered, and the filtrate was diluted with water (20 mL) and extracted with ethyl acetate (20 mL×3 times). The organic phase was washed with brine (30 mL×1 time), dried, filtered and concentrated under reduced pressure to obtain a crude product, and the crude product was purified by silica gel column chromatography (eluting with petroleum ether:ethyl acetate=1:1) to obtain compound 10C. LCMS (ESI): m/z: 374.0 [M+1].

Compound 10D

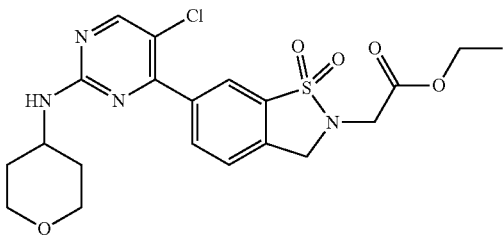

10D

4-Aminotetrahydropyran (140 mg, 1.38 mmol, 694.34 μL) and DIEA (148.40 mg, 1.15 mmol, 200 μL) were added to a solution of compound 10C (185 mg, 459.91 μmol) in dioxane (4 mL), and the reaction solution was stirred at 90° C. for 16 hours. Water (10 mL) and ammonium chloride (20 mL) were added to the reaction solution, and the reaction solution was extracted with ethyl acetate (20 mL×3 times). The organic phase was washed with brine (20 mL×1 time), dried, filtered and concentrated under reduced pressure to obtain a crude product of 10D, and the crude product was directly used in the next step. LCMS (ESI): m/z: 467.1 [M+1].

Compound 10E

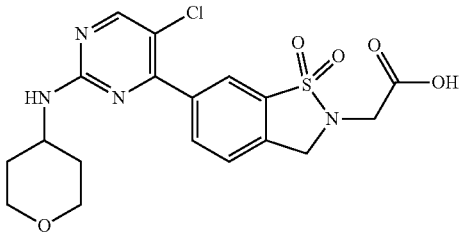

10E

An aqueous (1 mL) solution of lithium hydroxide monohydrate (20 mg, 476.64 μmol) was added to a solution of compound 10D (140 mg, 299.83 μmol) in tetrahydrofuran (2 mL) and ethanol (1 mL), and the reaction solution was stirred at 20° C. for 0.5 hours. The reaction solution was diluted with water (10 mL) and extracted with ethyl acetate (10 mL×1 time), and the pH of the aqueous phase was adjusted to 2 with hydrochloric acid (2 mol) aqueous solution, and the mixture was extracted with ethyl acetate (10 mL×3 times). The combined organic phases were combined, dried, filtered and concentrated under reduced pressure to obtain a crude product of IME, and the crude product was directly used in the next step. LCMS (ESI): m/z: 438.9 [M+1].

Compound 10

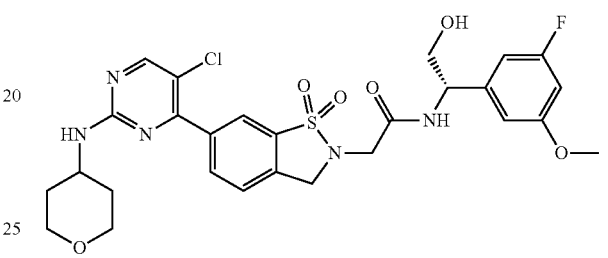

10

At 0° C., (2S)-2-amino-2-(3-fluoro-5-methoxy-phenyl) ethanol (90 mg, 406.03 μmol) and DIEA (148.40 mg, 1.15 mmol, 200 μL) were added to a solution of compound 10E (120 mg, 273.42 μmol) in dichloromethane (4 mL), and the reaction solution was stirred at 0° C. for 10 minutes. Then HATU (142 mg, 373.46 μmol) was added to the reaction solution, and the mixture was continued to react for 2 hours. The reaction solution was diluted with water (10 mL) and extracted with ethyl acetate (10 mL×3 times). The organic phase was washed with brine (20 mL×1 time), dried, filtered and concentrated under reduced pressure to obtain a crude product. The crude product was separated by preparative high performance liquid chromatography (formic acid system) to obtain a freebase of compound 10. $^1$H NMR (400 MHz, CD$_3$OD) δ=8.36 (s, 1H), 8.24 (d, J=1.1 Hz, 1H), 8.15 (dd, J=1.5, 8.2 Hz, 1H), 7.68 (d, J=8.2 Hz, 1H), 6.77 (s, 1H), 6.71 (br d, J=9.4 Hz, 1H), 6.58 (td, J=2.3, 10.8 Hz, 1H), 4.99 (dd, J=5.3, 6.9 Hz, 1H), 4.79-4.62 (m, 2H), 4.19-3.93 (m, 5H), 3.83-3.68 (m, 5H), 3.53 (dt, J=2.0, 11.7 Hz, 2H), 1.99 (br dd, J=2.1, 12.4 Hz, 2H), 1.68-1.55 (m, 2H). LCMS (ESI): m/z: 606.1 [M+1].

Embodiment 11

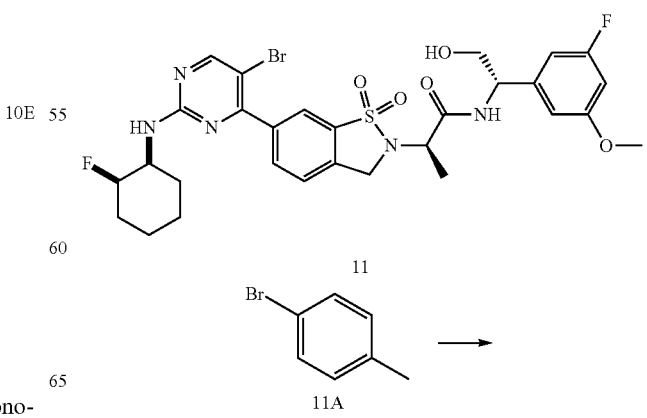

11

11A

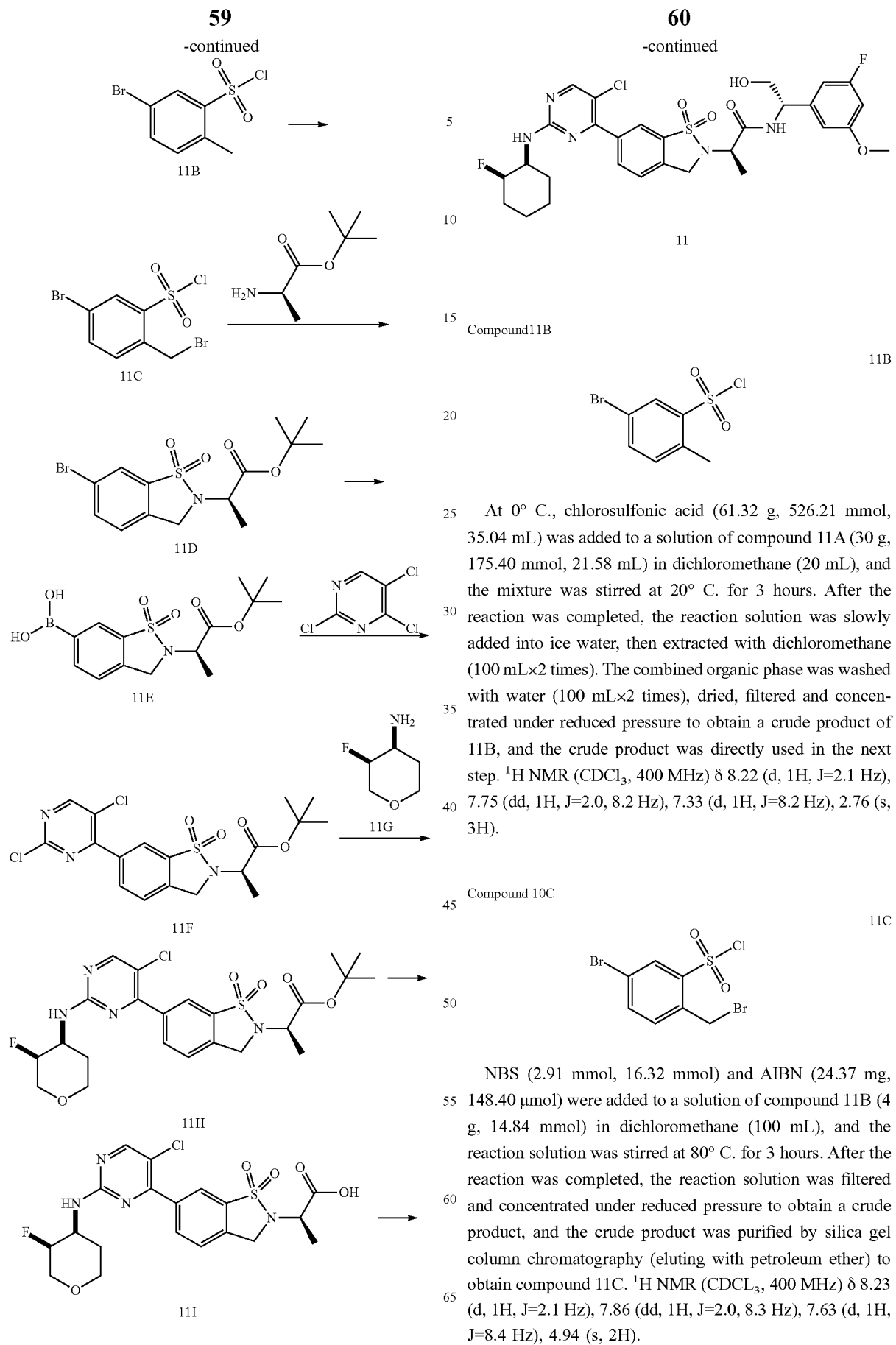

Compound 11B

11B

At 0° C., chlorosulfonic acid (61.32 g, 526.21 mmol, 35.04 mL) was added to a solution of compound 11A (30 g, 175.40 mmol, 21.58 mL) in dichloromethane (20 mL), and the mixture was stirred at 20° C. for 3 hours. After the reaction was completed, the reaction solution was slowly added into ice water, then extracted with dichloromethane (100 mL×2 times). The combined organic phase was washed with water (100 mL×2 times), dried, filtered and concentrated under reduced pressure to obtain a crude product of 11B, and the crude product was directly used in the next step. $^1$H NMR (CDCl$_3$, 400 MHz) δ 8.22 (d, 1H, J=2.1 Hz), 7.75 (dd, 1H, J=2.0, 8.2 Hz), 7.33 (d, 1H, J=8.2 Hz), 2.76 (s, 3H).

Compound 10C

11C

NBS (2.91 mmol, 16.32 mmol) and AIBN (24.37 mg, 148.40 μmol) were added to a solution of compound 11B (4 g, 14.84 mmol) in dichloromethane (100 mL), and the reaction solution was stirred at 80° C. for 3 hours. After the reaction was completed, the reaction solution was filtered and concentrated under reduced pressure to obtain a crude product, and the crude product was purified by silica gel column chromatography (eluting with petroleum ether) to obtain compound 11C. $^1$H NMR (CDCL$_3$, 400 MHz) δ 8.23 (d, 1H, J=2.1 Hz), 7.86 (dd, 1H, J=2.0, 8.3 Hz), 7.63 (d, 1H, J=8.4 Hz), 4.94 (s, 2H).

Compound 11D

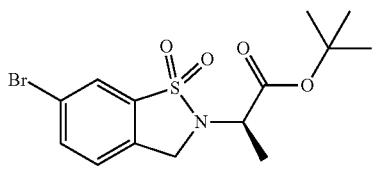

An aqueous (2 mL) solution of sodium carbonate (912.55 mg, 8.61 mmol) was added to a solution of compound 11C (1 g, 2.87 mmol) and compound (R)-tert-butyl-2-aminopropionate (521.35 mg, 2.87 mmol) in acetonitrile (10 mL), and the mixture was stirred at 20° C. for 1 hour, and then stirred at 80° C. for 13 hours. After the reaction was completed, the reaction solution was diluted with water (20 mL) and extracted with ethyl acetate (20 mL×3 times). The organic phase was washed with brine (20 mL×1 time), dried, filtered and concentrated under reduced pressure to obtain a crude product of compound 11D, and the crude product was directly used in the next step. $^1$H NMR (CDCl$_3$, 400 MHz) δ 7.94 (s, 1H), 7.72 (d, 1H, J=8.2 Hz), 7.29 (d, 1H, J=8.2 Hz), 4.86 (d, 1H, J=13.9 Hz), 4.4-4.5 (m, 2H), 1.61 (d, 3H, J=7.3 Hz), 1.45 (s, 9H). LCMS (ESI): m/z: 377.9 [M+1].

Compound 11E

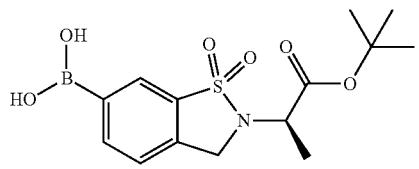

Under the protection of nitrogen, compound 11D (15 g, 39.87 mmol), bis(pinacolato)diboron (15.19 g, 59.80 mmol), Pd(dppf)Cl$_2$·CH$_2$Cl$_2$ (1.63 g, 1.99 mmol) and potassium acetate (7.82 g, 79.73 mmol) were dissolved in dioxane (70 mL), and the reaction solution was stirred at 90° C. for 1 hour. The reaction solution was concentrated under reduced pressure to obtain a crude product of compound 11E, and the crude product was directly used in the next step. LCMS (ESI): m/z: 341.7 [M+1].

Compound 11F

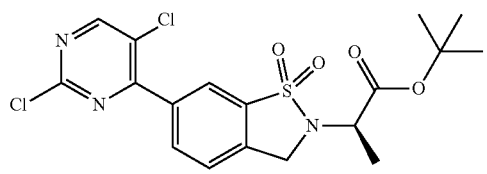

Under the protection of nitrogen, compound 11E (4.2 g, 12.31 mmol), 2,4,5-trichloropyrimidine (4.52 g, 24.62 mmol), Pd(PPh$_3$)$_4$ (711.25 mag, 615.50 μmol) and sodium carbonate (2.61 g, 24.62 mmol) were dissolved in dioxane (20 mL) and water (4 mL), and the reaction solution was stirred at 90° C. for 16 hours. After the reaction was completed, the reaction solution was filtered, and the filtrate was diluted with water (30 mL) and extracted with ethyl acetate (30 mL×3 times). The organic phase was washed with brine (30 mL×1 time), dried, filtered and concentrated under reduced pressure to obtain a crude product, and the crude product was purified by silica gel column chromatography (eluting with petroleum ether:ethyl acetate=10:1 to 3:1) to obtain compound 11F. $^1$H NMR (CDCl$_3$, 400 MHz) δ 8.71 (s, 1H), 8.41 (d, 1H, J=1.1 Hz), 8.18 (dd, 1H, J=1.5, 8.1 Hz), 7.58 (d, 1H, J=8.1 Hz), 5.01 (d, 1H, J=14.5 Hz), 4.62 (d, 1H, J=14.5 Hz), 4.48 (d, 1H, J=7.3 Hz), 1.64 (d, 3H, J=7.3 Hz), 1.46 (s, 9H).

Compound 11H

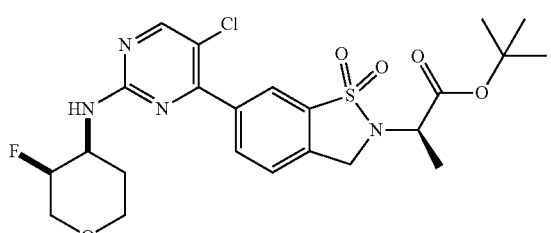

Compound 11g (682.86 mg, 4.39 mmol) and DIEA (1.89 g, 14.63 mmol, 2.55 mL) were added to a solution of compound 11F (1.3 g, 2.93 mmol) in dioxane (4 mL), and the reaction solution was stirred at 100° C. for 16 hours, and then the reaction solution was diluted with ethyl acetate (30 mL) and washed with 1 mol of hydrochloric acid (30 mL×1 time) aqueous solution. The aqueous phase was extracted with ethyl acetate (30 mL×3 times), and the combined organic phase was washed with brine (30 mL×1 time), dried and concentrated under reduced pressure to obtain a crude product. The crude product was purified by silica gel column chromatography (eluting with petroleum ether:ethyl acetate=5:1 to 2:1) to obtain compound 11H. $^1$H NMR (CDCl$_3$, 400 MHz) δ 8.2-8.3 (m, 1f), 8.18 (br s, 1H), 7.99 (dd, 1H, J=1.4, 8.1 Hz), 7.44 (d, 1H, J=8.3 Hz), 5.47 (br d, 1H, J=9.0 Hz), 4.91 (d, 1H, J=14.4 Hz), 4.6-4.7 (m, 1H), 4.52 (d, 1H, J=14.3 Hz), 4.40 (q, 1H, J=7.3 Hz), 4.1-4.3 (m, 2H), 3.99 (br dd, 1H, J=4.4, 11.6 Hz), 3.4-3.6 (m, 21H), 1.9-2.0 (m, 1H), 1.8-1.9 (m, 1H), 1.56 (d, 3H, J=7.4 Hz), 1.38 (s, 91H), LCMS (ESI): m/z: 526.9 [M+1].

Compound 11I

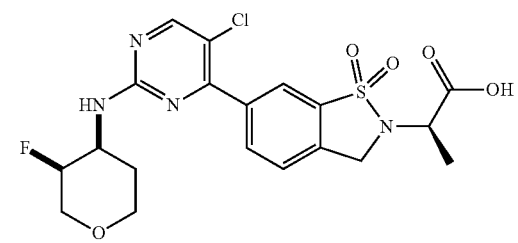

Trifluoroacetic acid (1.84 g, 16.13 mmol, 1.19 mL) was added to a solution of compound 11H (850 mg, 1.61 mmol) in dichloromethane (10 mL), and the reaction solution was stirred at 50° C. for 16 hours. After the reaction was completed, the reaction solution was diluted with water (30 mL) and extracted with ethyl acetate (30 mL×2 times). The organic phase was washed with brine (30 mL×1 time), dried, filtered and concentrated under reduced pressure to obtain a crude product of compound 11I, and the crude product was directly used in the next step. LCMS (ESI): m/z: 470.8 [M+1].

Compound 11

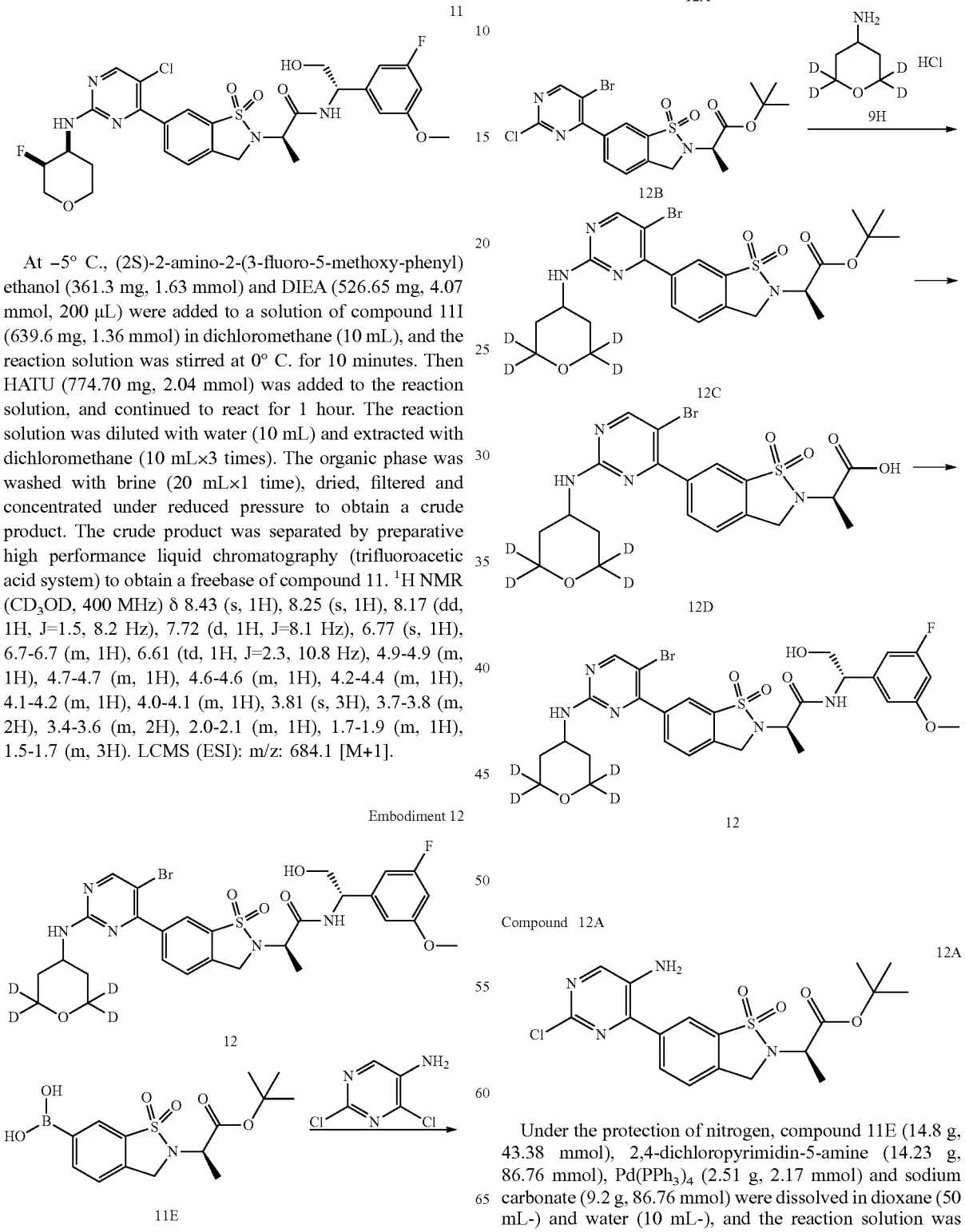

At −5° C., (2S)-2-amino-2-(3-fluoro-5-methoxy-phenyl) ethanol (361.3 mg, 1.63 mmol) and DIEA (526.65 mg, 4.07 mmol, 200 μL) were added to a solution of compound 11I (639.6 mg, 1.36 mmol) in dichloromethane (10 mL), and the reaction solution was stirred at 0° C. for 10 minutes. Then HATU (774.70 mg, 2.04 mmol) was added to the reaction solution, and continued to react for 1 hour. The reaction solution was diluted with water (10 mL) and extracted with dichloromethane (10 mL×3 times). The organic phase was washed with brine (20 mL×1 time), dried, filtered and concentrated under reduced pressure to obtain a crude product. The crude product was separated by preparative high performance liquid chromatography (trifluoroacetic acid system) to obtain a freebase of compound 11. $^1$H NMR (CD$_3$OD, 400 MHz) δ 8.43 (s, 1H), 8.25 (s, 1H), 8.17 (dd, 1H, J=1.5, 8.2 Hz), 7.72 (d, 1H, J=8.1 Hz), 6.77 (s, 1H), 6.7-6.7 (m, 1H), 6.61 (td, 1H, J=2.3, 10.8 Hz), 4.9-4.9 (m, 1H), 4.7-4.7 (m, 1H), 4.6-4.6 (m, 1H), 4.2-4.4 (m, 1H), 4.1-4.2 (m, 1H), 4.0-4.1 (m, 1H), 3.81 (s, 3H), 3.7-3.8 (m, 2H), 3.4-3.6 (m, 2H), 2.0-2.1 (m, 1H), 1.7-1.9 (m, 1H), 1.5-1.7 (m, 3H). LCMS (ESI): m/z: 684.1 [M+1].

Embodiment 12

Compound 12A

Under the protection of nitrogen, compound 11E (14.8 g, 43.38 mmol), 2,4-dichloropyrimidin-5-amine (14.23 g, 86.76 mmol), Pd(PPh$_3$)$_4$ (2.51 g, 2.17 mmol) and sodium carbonate (9.2 g, 86.76 mmol) were dissolved in dioxane (50 mL-) and water (10 mL-), and the reaction solution was stirred at 90° C. for 16 hours. After the reaction was completed, the reaction solution was filtered, and the filtrate was diluted with water (100 mL) and extracted with ethyl acetate (100 mL×2 times). The organic phase was washed with brine (100 mL×1 time), dried, filtered and concentrated under reduced pressure to obtain a crude product, and the crude product was purified by silica gel column chromatography (eluting with petroleum ether:ethyl acetate=10:1 to 3:1) to obtain compound 12A. LCMS (ESI): m/z: 424.8 [M+1].

Compound 12B

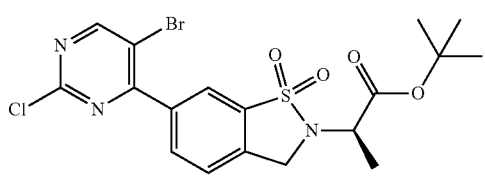

A solution of compound 12A (100 mg, 235.35 μmol) in acetonitrile (3 mL) was added to a solution of cuprous bromide (50.64 mg, 353.02 μmol, 10.75 μL) and wert-butyl nitrite (60.67 mg, 588.37 μmol, 69.98 μL) in acetonitrile (3 mL), and the reactant was stirred at 20° C. for 18 hours. The reaction solution was diluted with water (10 mL) and extracted with ethyl acetate (10 mL×2 times). The organic phase was washed with brine (10 mL×1 time), dried, filtered and concentrated under reduced pressure to obtain a crude product. The crude product was purified by silica gel column chromatography (eluting with petroleum ether:ethyl acetate=1:1) to obtain compound 12B. $^1$H NMR (CDCl$_3$, 400 MHz) δ 8.84 (s, 1H), 8.35 (d, 1H, J=1.1 Hz), 8.11 (dd, 1H, J=1.6, 8.1 Hz), 7.57 (d, 1H, J=8.4 Hz), 5.01 (d, 1H, J=14.5 Hz), 4.62 (d, 1H, J=14.5 Hz), 4.49 (d, 1H, J=7.4 Hz), 1.64 (d, 3H, J=7.4 Hz), 1.46 (s, 9H). LCMS (ESI): m/z: 489.8 [M+1].

Compound 12C

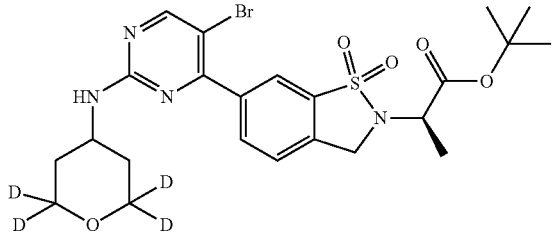

Compound 9H (869.3 mg, 6.14 mmol) and DIEA (1.19 g, 9.21 mmol, 2.55 mL) were added to a solution of compound 12B (1.5 g, 3.07 mmol) in dioxane (15 mL), and the reaction solution was stirred at 90° C. for 16 hours, and then the reaction solution was diluted with ethyl acetate (30 mL) and washed with 1 mol of hydrochloric acid (30 mL×1 time) aqueous solution. The aqueous phase was extracted with ethyl acetate (30 mL×3 times), and the combined organic phase was washed with brine (30 mL×1 time), dried and concentrated under reduced pressure to obtain a crude product. The crude product was purified by silica gel column chromatography (eluting with petroleum ether:ethyl acetate=5:1 to 2:1) to obtain compound 12C. $^1$H NMR (CDCl$_3$, 400 MHz) δ 8.66 (d, 11H, J=5.1 Hz), 8.4-8.5 (m, 1H), 8.36 (dd, 1H, J=1.6, 8.1 Hz), 7.63 (d, 1H, J=5.1 Hz), 7.5-7.5 (m, 1H), 4.9-5.0 (m, 1H), 4.54 (d, 1H, J=14.6 Hz), 4.40 (q, 1H, J=7.3 Hz), 1.56 (d, 3H, J=7.3 Hz), 1.38 (s, 9H). LCMS (ESI): m/z: 559.1[M+1].

Compound 12D

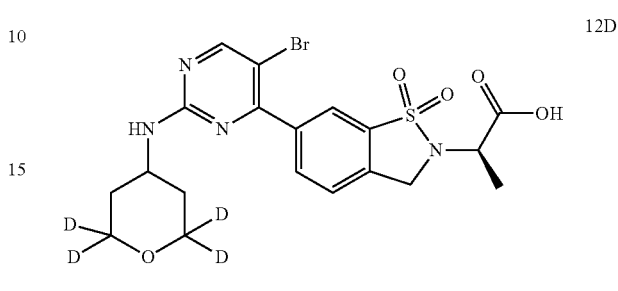

Trifluoroacetic acid (1.23 g, 10.76 mmol, 796.86 mL) was added to a solution of compound 12C (600 mg, 1.08 mmol) in dichloromethane (10 mL), and the reaction solution was stirred at 50° C. for 6 hours. After the reaction was completed, the reaction solution was diluted with water (30 mL) and extracted with ethyl acetate (30 mL×2 times). The organic phase was washed with brine (30 mL×1 time), dried, filtered and concentrated under reduced pressure to obtain a crude product of compound 12D, and the crude product was directly used in the next step. LCMS (ESI): m/z: 502.19 [M+1].

Compound 12

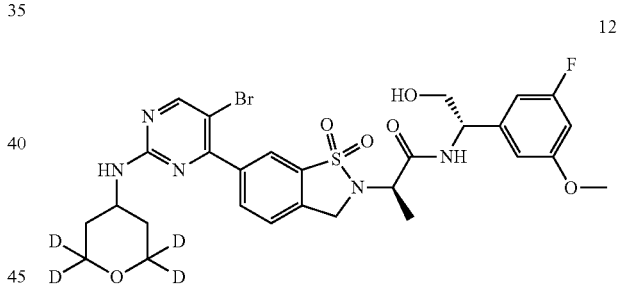

At −5° C., (2S)-2-amino-2-(3-fluoro-5-methoxy-phenyl) ethanol (212.2 mg, 957.34 μmol) and DIEA (309.32 mg, 2.39 mmol, 416.87 μL) were added to a solution of compound 12D (400 mg, 797.79 μmol) in dichloromethane (10 mL), and the reaction solution was stirred at 0° C. for 10 minutes. Then HATU (455.01 mg, 1.2 mmol) was added to the reaction solution, and continued to react for 1 hour. The reaction solution was diluted with water (10 mL) and extracted with dichloromethane (10 mL×3 times). The organic phase was washed with brine (20 mL×1 time), dried, filtered and concentrated under reduced pressure to obtain a crude product. The crude product was separated by preparative high performance liquid chromatography (trifluoroacetic acid system) to obtain a freebase of compound 12. H NMR (CD$_3$OD, 400 MHz) δ 8.48 (s, 1H), 8.17 (s, 1H), 8.0-8.1 (m, 1H), 7.70 (d, 1H, J=8.1 Hz), 6.77 (s, 1H), 6.70 (br d, 1H, J=9.5 Hz), 6.6-6.7 (m, 1H), 5.0-5.0 (m, 1H), 4.69 (s, 1H), 4.6-4.6 (m, 1H), 4.0-4.1 (m, 1H), 3.81 (s, 3H), 3.7-3.8 (m, 2H), 1.99 (dd, 2H, J=4.2, 13.3 Hz), 1.5-1.7 (m, 6H). LCMS (ESI): m/z: 670.0 [M+1].

Embodiment 13

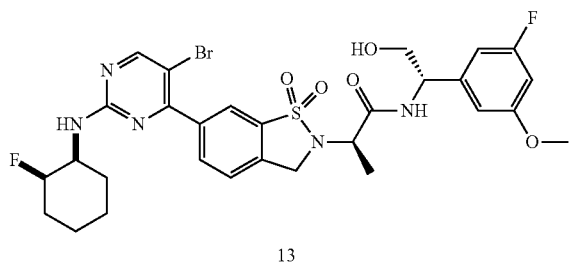

13

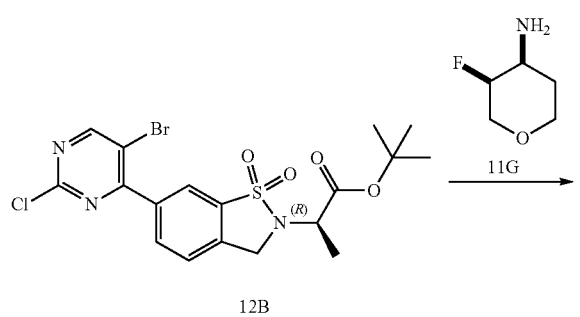

12B

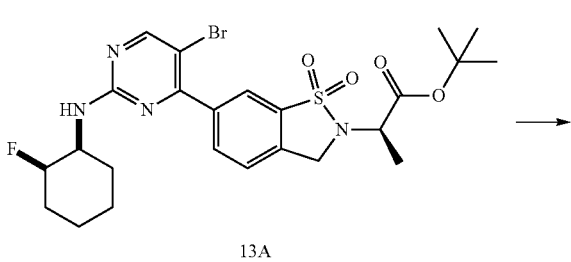

13A

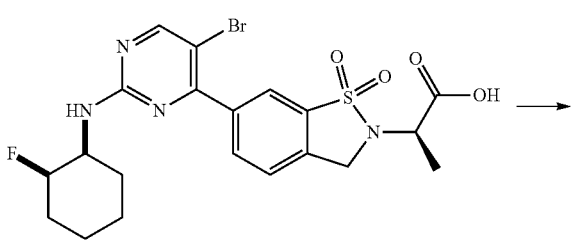

13B

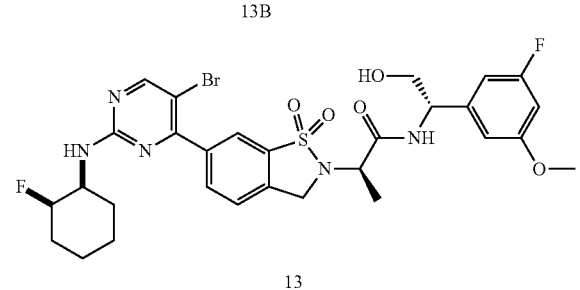

13

Compound 13A

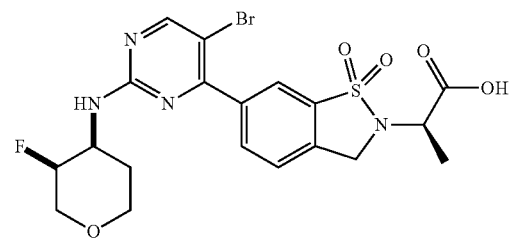

13A

Compound 11G (955.37 mg, 6.14 mmol) and DIEA (1.98 g, 15.35 mmol, 2.67 mL) were added to a solution of compound 12B (1.5 g, 3.07 mmol) in dioxane (10 mL), and the reaction solution was stirred at 90° C. for 16 hours, and then the reaction solution was diluted with ethyl acetate (30 mL) and washed with 1 mol of hydrochloric acid (30 mL×1 time) aqueous solution. The aqueous phase was extracted with ethyl acetate (30 mL×3 times), and the combined organic phase was washed with brine (30 mL×1 time), dried and concentrated under reduced pressure to obtain a crude product. The crude product was purified by silica gel column chromatography (eluting with petroleum ether:ethyl acetate=5:1 to 2:1) to obtain compound 13A. LCMS (ESI): m/z: 572.9 [M+1].

Compound 13B

Trifluoroacetic acid (1.2 g, 10.5 mmol, 777.39 ml) was added to a solution of compound 13A (1.2 g, 2.1 mmol) in dichloromethane (15 mL), and the reaction solution was stirred at 50° C. for 16 hours. After the reaction was completed, the reaction solution was diluted with water (30 mL) and extracted with ethyl acetate (30 mL×2 times). The organic phase was washed with brine (30 mL×1 time), dried, filtered and concentrated under reduced pressure to obtain a crude product of compound 13B. and the crude product was directly used in the next step. LCMS (ESI): m/z: 516.9 [M+1].

Compound 13

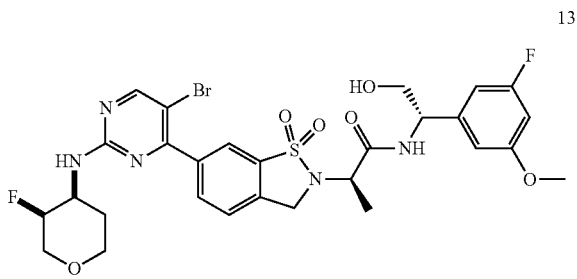

13

At −5° C., (2S)-2-amino-2-(3-fluoro-5-methoxy-phenyl) ethanol (464.51 mg, 2.1 mmol) and DIEA (677.12 mug, 5.24 mmol, 912.56 μL) were added to a solution of compound 13B (900 mg, 1.75 mmol) in dichloromethane (20 mL), and the reaction solution was stirred at −5° C. for 10 minutes. Then HATU (455.01 mg, 1.2 mmol) was added to the reaction solution, and continued to react for 1 hour. The reaction solution was diluted with water (10 mL) and extracted with dichloromethane (20 mL×3 times). The organic phase was washed with brine (20 mL×1 time), dried, filtered and concentrated under reduced pressure to obtain a crude product. The crude product was separated by preparative high performance liquid chromatography (trifluoroacetic acid system) to obtain a freebase of compound 13. $^1$H NMR (CD$_3$OD, 400 MHz) δ 8.52 (s, 1H), 8.18 (s, 1H), 8.10 (dd, 1H, J=1.5, 8.1 Hz), 7.71 (d, 1H, J=8.1 Hz), 6.77 (s, 1H), 6.70 (br d, 1H, J=9.3 Hz), 6.61 (td, 1H, J=2.1, 10.7 Hz), 5.0-5.0 (m, 2H), 4.7-4.8 (m, 2H), 4.61 (q, 1H, J=7.1 Hz), 4.2-4.4 (m, 1H), 4.12 (br t, 1H, J=12.3 Hz), 4.0-4.1 (m, 1H), 3.81 (s, 3H), 3.7-3.8 (m, 2H), 3.5-3.7 (m, 2H), 2.05 (dq, 1H, J=4.3, 12.6 Hz), 1.83 (br dd, 1H, J=3.5, 13.3 Hz), 1.61 (d, 3H, J=7.1 Hz). LCMS (ESI): m/z: 684.1 [M+1].

Embodiment 14

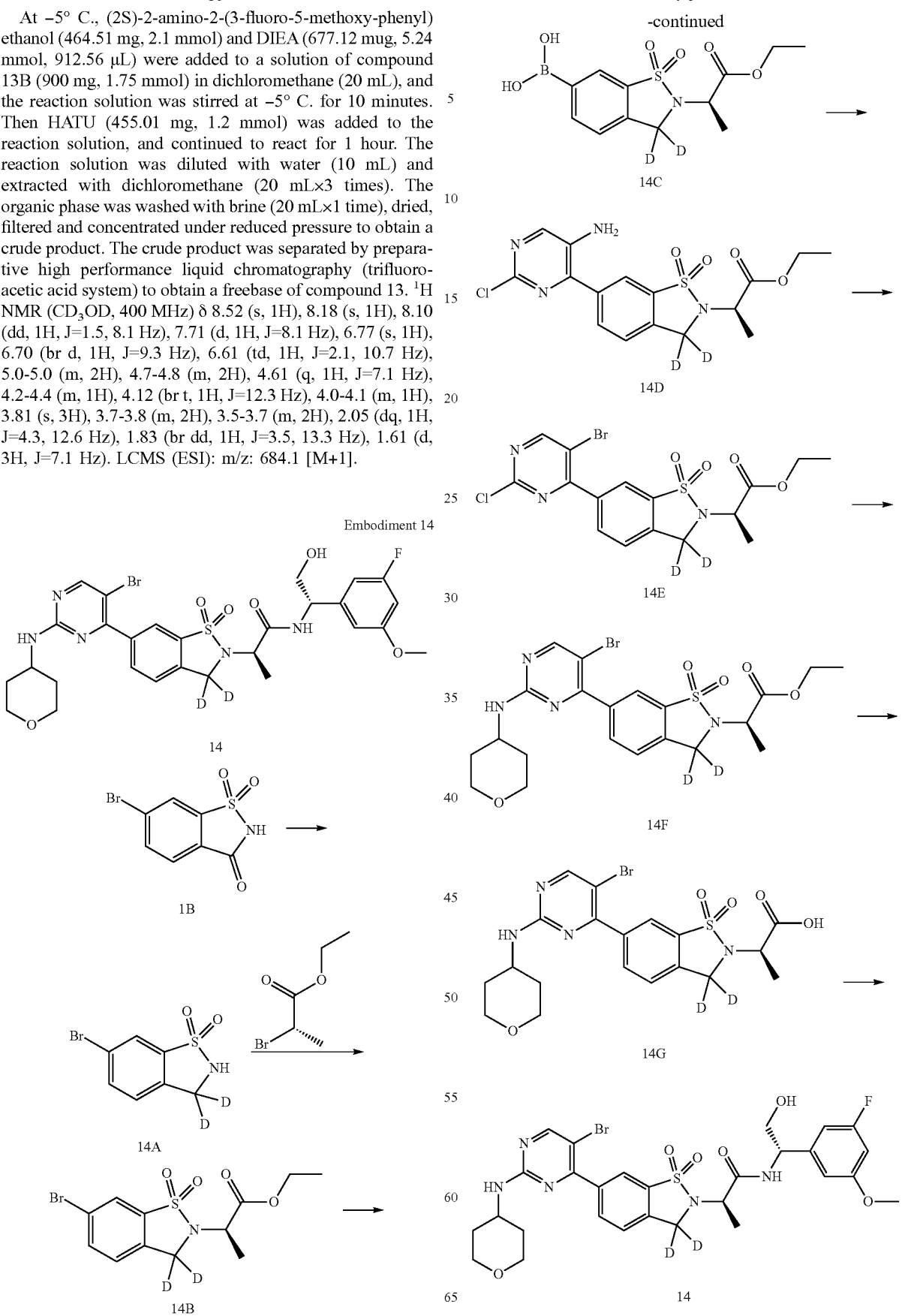

Compound 14A

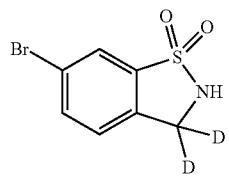

14A

Sodium borodeuteride (646.80 mg, 17.10 mmol) was added to a solution of compound 1B (1.4 g, 5.34 mmol) in tetrahydrofuran (10 mL), then the temperature of the reaction solution was reduced to −5° C., and boron trifluoride etherate (2.43 g, 17.09 mmol, 2.11 ml) was slowly added to the reaction solution, and the mixture was stirred at 80° C. for 2 hours. After the reaction was completed, the reaction solution was quenched with ammonium chloride aqueous solution (20 mL) at 0° C., and ethyl acetate (60 mL) was added, then the reaction solution was filtered, and the filtrate was extracted with ethyl acetate (20 mL×2 times), and the combined organic phase was washed with brine (30 mL×1 time), dried and concentrated under reduced pressure to obtain a crude product. The crude product was stirred with petroleum ether:ethyl acetate=3:1 at 25° C. for 0.5 hours, and the filter cake obtained by filtration was compound 14A. $^1$H NMR (400 MHz, DMSO-$d_6$) δ=8.12 (d, J=1.3 Hz, 1H), 7.95 (s, 1H), 7.87 (dd, J=1.3, 8.2 Hz, 1H), 7.54 (d, J=8.3 Hz, 1H). LCMS (EST): m/z: 250.11.

Compound 14B

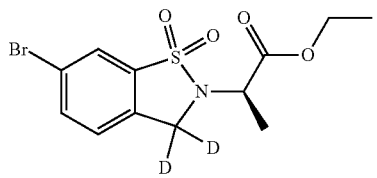

14B

Under the protection of nitrogen, compound 14A (990 mg, 3.60 mmol), ethyl (2S)-2-bromopropanoate (990 mg, 5.14 mmol) and potassium carbonate (990 mg, 5.47 mmol) were dissolved in DMF (10 mL), and the mixture was stirred for 16 hours at 20° C. The reaction mixture was diluted with 30 mL, of water and then extracted with ethyl acetate (30 mL×2 times). The combined organic phase was washed with water (40 mL×2 times) and concentrated under reduced pressure to obtain a crude product, and the crude product was purified by silica gel column chromatography (eluting with petroleum ether:ethyl acetate=20:1 to 15:1) to obtain compound 14B. $^1$H NMR (400 MHz, CDCl$_3$, 400 MHz) δ=7.86 (d, J=1.7 Hz, 1H), 7.65 (dd, J=1.7, 8.3 Hz, 1H), 7.20 (d, J=8.7 Hz, 1H), 4.47 (q, J=7.3 Hz, 1H), 4.17-4.07 (m, 2H), 1.56 (d, J=7.3 Hz, 3H), 1.19 (t, J=7.1 Hz, 3H). LCMS (ESI): m/z: 350.22 [M+1].

Compound 14C

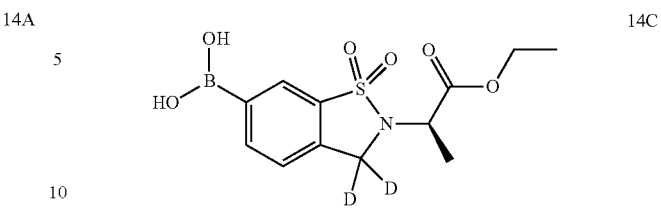

14C

Under the protection of nitrogen, compound 14B (550 mg, 1.57 mmol), bis(pinacolato)diboron (630 mg, 2.48 mmol), Pd(dppf)Cl$_2$·CH$_2$Cl$_2$ (80 mg, 97.96 μmol) and potassium acetate (314 mg, 3.2 mmol) were dissolved in dioxane (8 mL), and the reaction solution was stirred at 100° C. for 2 hours. The reaction solution was filtered and concentrated under reduced pressure to obtain a crude product of compound 14C, and the crude product was directly used in the next step. LCMS (ESI): m/z: 315.15 [M+1].

Compound 14D

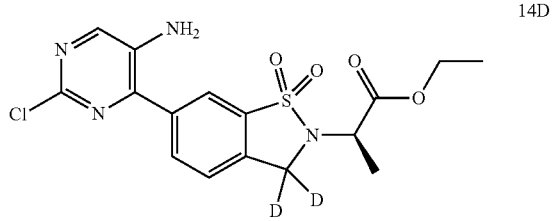

14D

Under the protection of nitrogen, compound 14C (494 mg, 1.57 mmol), 2,4-dichloropyrimidin-5-amine (462 mg, 2.82 mmol), Pd(PPh$_3$)$_4$ (96 mg, 83.08 μmol) and sodium carbonate (334 mg, 3.15 mmol) were dissolved in dioxane (5 mL) and water (1 mL), and the reaction solution was stirred at 100° C. for 2 hours. After the reaction was completed, the reaction solution was filtered, dried, filtered and concentrated under reduced pressure to obtain a crude product, and the crude product was purified by silica gel column chromatography (eluting with petroleum ether:ethyl acetate=3:1 to 1:1) to obtain compound 14D. $^1$H NMR (CDCl$_3$, 400 MHz) δ=8.20 (d, J=1.1 Hz, 1H), 8.13 (s, 1H), 8.00 (dd, J=1.4, 8.0 Hz, 1H), 7.51 (d, J=8.0 Hz, 1H), 4.51 (q, J=7.3 Hz, 1H), 4.19-4.09 (m, 2H), 1.59 (d, J=7.4 Hz, 3H), 1.24-1.17 (m, 3H). LCMS (ESI): m/z: 398.86 [M+1].

Compound 14E

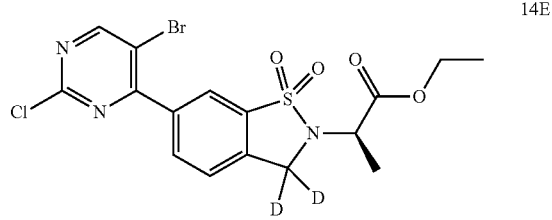

14E

At 0° C., a solution of compound 14D (500 mg, 1.25 mmol) in acetonitrile (3 mL) was added to a solution of cuprous bromide (360 mg, 2.51 mmol, 76.43 μL) and tert-butyl nitrite (387 mg, 3.75 mmol, 446.37 μL) in acetonitrile (3 mL), and the reactant was stirred at 25° C. for 12 hours. The reaction solution was diluted with water (10 mL)

and extracted with ethyl acetate (10 mL×3 times). The organic phase was washed with brine (10 mL×1 time), dried, filtered and concentrated under reduced pressure to obtain a crude product. The crude product was purified by silica gel column chromatography (eluting with petroleum ether:ethyl acetate=4:1 to 3:1) to obtain compound 14E. $^1$H NMR (CDCl$_3$, 400 MHz) δ=8.76 (s, 1H), 8.27 (d, J=1.1 Hz, 1H), 8.04 (dd, J=1.7, 8.1 Hz, 1H), 7.50 (d, J=8.1 Hz, 1H), 4.52 (q, J=7.3 Hz, 1H), 4.18-4.10 (m, 2H), 1.59 (d, J=7.3 Hz, 3H), 1.23-1.18 (m, 3H). LCMS (ESI): m/z: 462.74 [M+1].

Compound 14F

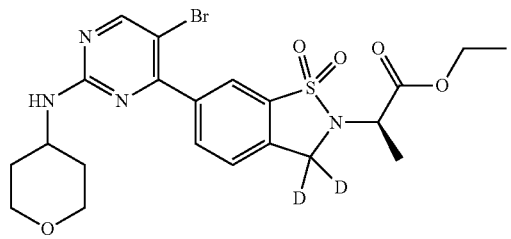

14F

Compound aminotetrahydropyran (202 mg, 2.00 mmol) and DIEA (207 mg, 1.60 mmol, 278.98 µL) were added to a solution of compound 14E (370 mg, 799.58 µmol) in dioxane (5 mL), and the reaction solution was stirred at 90° C. for 4 hours, and then the reaction solution was diluted with water (10 mL) and extracted with ethyl acetate (10 mL×3 times). The combined organic phase was dried and concentrated under reduced pressure to obtain a crude product of 14F, and the crude product was directly used in the next step. $^1$H NMR (CDCl$_3$, 400 MHz) δ=8.37 (s, 1H), 8.13 (d, J=1.0 Hz, 1H), 7.94 (dd, J=1.6, 8.0 Hz, 1H), 7.53-7.38 (m, 1H), 4.52 (q, J=7.3 Hz, 1H), 4.20-4.10 (m, 2H), 3.96-3.89 (m, 2H), 3.52-3.42 (m, 2H), 2.01-1.91 (m, 2H), 1.59 (d, J=7.4 Hz, 3H), 1.51-1.47 (m, 3H), 1.22-1.20 (m, 3H). LCMS (ESI): m/z: 527.43 [M+1].

Compound 14G

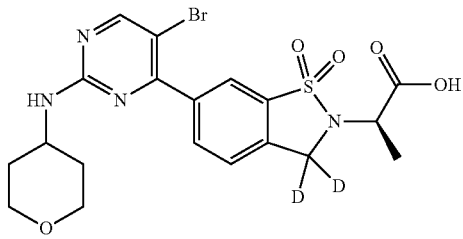

14G

An aqueous (2 mL) solution of lithium hydroxide monohydrate (59 mg, 1.4 mmol) was added to a solution of compound 14F (370 mg, 701.52 µmol) in tetrahydrofuran (2 mL), and the reaction solution was stirred at 20° C. for 0.5 hours. After the reaction was completed, the reaction solution was concentrated under reduced pressure, and the pH of the reaction solution was adjusted to 2 with 2 mol of hydrochloric acid aqueous solution, and then the solution was extracted with ethyl acetate (10 mL×3 times). The combined organic phase was filtered, and the filtrate was concentrated under reduced pressure to obtain a crude product of compound 14G. $^1$H NMR (400 MHz, DMSO-d$_6$) δ=8.54 (s, 1H), 8.08 (s, 1H), 8.04-7.95 (m, 1H), 7.76 (d, J=8.0 Hz, 1H), 4.41 (q, J=7.3 Hz, 1H), 3.97-3.90 (m, 1H), 3.86 (br d, J=10.8 Hz, 2H), 3.42-3.38 (m, 2H), 1.84 (br d, J=10.1 Hz, 2H), 1.56-1.47 (m, 5H).

Compound 14

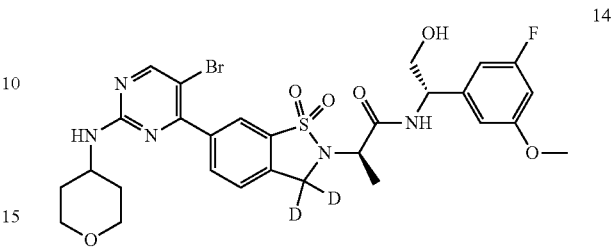

14

HATU (376 mg, 988.88 µmol) and DIEA (170 mg, 1.32 mmol, 229.11 µL) were added to a solution of compound 14G (330 mg, 660.83 µmol) and (2S)-2-amino-2-(3-fluoro-5-methoxy-phenyl)ethanol (176 mg, 794.02 µmol) in dichloromethane (5 mL), and the reaction solution was stirred at 20° C. for 1 hour. The reaction solution was diluted with water (10 mL) and extracted with dichloromethane (20 mL×3). The organic phase was washed with brine (20 mL×1 time), dried, filtered and concentrated under reduced pressure to obtain a crude product. The crude product was separated by preparative high performance liquid chromatography (trifluoroacetic acid system) to obtain a freebase of compound 14. $^1$H NMR (400 MHz. CD$_3$O) δ=8.48 (s, 1H), 8.17 (d, J=1.0 Hz, 1H), 8.10 (dd, J=1.6, 8.1 Hz, 1H), 7.70 (d, J=8.4 Hz, 1H), 6.77 (s, 1H), 6.73-6.67 (m, 1H), 6.61 (td, J=2.3, 10.8 Hz, 1H), 4.98-4.91 (m, 1H), 4.61 (q, J=7.0 Hz, 1H), 4.10-4.02 (m, 1H), 4.01-3.94 (m, 2H), 3.83-3.79 (m, 3H), 3.78-3.68 (m, 2H), 3.59-3.49 (m, 2H), 2.04-1.96 (m, 2H), 1.68-1.56 (m, 5H). LCMS (ESI): m/z: 666.10 [M+1].

Activity Test

Experimental Embodiment 1: Calu-6 (Kras$^{Q61K}$) Antiproliferative Activity Experiment Experimental Materials:

| Name | Brand number |
|---|---|
| Calu-6 cell | ATCC-HTB-56 |
| RPMI1640 culture medium | Gibco-22400-089 |
| Fetal bovine serum | Cellmax-BL100-02 |
| L-glutamine | Gibco-35050-061 |
| DPBS | Corning-21-031-CVR |
| Trypsin | Gibco-25200-072 |
| Dual antibodies (penicillin, streptomycin) | Merck-TMS-AB2-C |
| CellTiterGlo | Promega-g7573 |
| Cell plate | Greiner-781091 |
| Echo shallow well plate | Labcyte-LP-0200 |

Experimental Steps:

Cell Inoculation:

(1) cell culture medium: 88% RPMI-1640, 10% fetal bovine serum, 1% L-glutamine and 1% penicillin-streptomycin;

(2) culture medium, trypsin and DPBS were preheated in a 37° C. water bath;

(3) the original culture medium was removed in the cell culture flask and washed once with 6 mL of PBS;

(4) 3.5 mL of trypsin was added to the cell culture flask, and the cell culture flask was shaken gently, and the trypsin was removed after full contact with the cell, and then the culture flask was placed into a 37° C. incubator containing 5% $CO_2$ for about 1 minute;

(5) the cells were resuspended with 10 mL of cell culture medium, and about 0.6 mL of cell suspension (ViCell XR) was taken out for counting;

(6) the cell suspension was diluted with culture medium to a cell density required for plating of $2.5 \times 10^4$ cells per mL;

(7) 100 μL of PBS was added to each well around the cell plate, and 40 μL of cell suspension was added to the other wells, and placed in a 37° C. incubator containing 5% $CO_2$ for overnight culture.

(8) The required cell amount and culture medium were taken based on the new $T_{75}$ culture flask for continued culture.

Administration:

(1) the compound to be tested was prepared into 10 mmol solution with DMSO;

(2) 9 μL of the compound was taken and added to Echo shallow well plate (Labcyte, #LP-0200), and the shallow well plate was centrifuged at 1000 rpm for 10 seconds;

(3) DPBS at the periphery of the cell plate was sucked out;

(4) the compound was gradient diluted and administrated with Echo, and 10 concentration gradients of each compound were diluted, and 100 nL of the diluent was added to the 384 cell plate separately, and then the cell plate was put back to the incubator and cultured for three days;

(5) then 100 μL of DPBS was added to the periphery of the cell plate.

Reading and Analyzing Data:

(1) CTG was added and the plate was read: 20 μL of CellTiterGlo was added to each well of the cell plate, and the cell plate was shaken in the dark for 10 min. and the plate was read on Envision.

Experimental Results:

| Compound | Antiproliferative activity of Calu-6 cells $IC_{50}$ (nM) |
| --- | --- |
| Compound 1 | 88.45 |
| Compound 2 | 222 |
| Compound 3 | 300 |
| Compound 4 | 239 |
| Compound 5 | 222 |
| Compound 6 | 508 |
| Compound 7 | 210 |
| Compound 8 | 313 |
| Compound 9 | 222 |
| Compound 10 | 253 |

Experimental conclusion: The compound of the present disclosure has a certain antiproliferative activity of Calu-6 cells.

Experimental Embodiment 2: HCT116 ($Kras^{G13D}$) Antiproliferative Activity Experiment Experimental Materials:
1) Experimental Reagents and Consumables:

| Name | Brand number |
| --- | --- |
| Mc'Coy 5A culture medium | BI-01-075-1ACS |
| Fetal bovine serum | Biosera-FB-1058/500 |
| 0.25% Trypsin | BasalMadia-S310KJ |
| Dual antibodies (penicillin, streptomycin) | Procell-PB180120 |
| CellTiter Glo | Promega-G7573 |
| Cell plate | Corning-3610 |

2) Experimental Instruments:

| Name | Brand number |
| --- | --- |
| Cell counting plate | Qiujing |
| Victor Nivo | PerkinElmer |

Experimental Steps:

Cell Inoculation:

(1) cell culture medium: 89% Mc'Coy 5A, 10% fetal bovine serum and 1% penicillin-streptomycin;

(2) culture medium and trypsin were preheated in a 37° C. water bath;

(3) the culture medium was removed in the cell culture flask and washed once with 1 mL of trypsin;

(4) 1 mL of trypsin was added to the cell culture flask, and the cell culture flask was shaken gently, and the trypsin was removed after full contact with the cell, and then the culture flask was placed into a 37° C. incubator containing 5% $CO_2$ for about 1 minute;

(5) the cells were resuspended with 2 mL of cell culture medium, and about 0.01 mL of cell suspension was taken out for counting;

(6) the cell suspension was diluted with culture medium to a cell density required for plating of $2.5 \times 10^4$ cells per mL;

(7) 100 μL of culture medium was added to each well around the cell plate, and 80 μL of cell suspension was added to the other wells, and placed in a 37° C. incubator containing 5% $CO_2$ for overnight culture.

(8) The required cell amount and culture medium were taken based on the new T75 culture flask for continued culture.

Administration:

(1) the compound to be tested was prepared into 10 mmol solution with DMSO;

(2) 9 concentration gradients and 3-fold dilutions were performed on the compounds, that is, a double-duplicate experiment was set from 6 mmol to 2.7 μmol, and 78 μL of culture medium was added to the middle plate, and then 2 μL of gradient diluted compound per well was transferred to the middle plate according to the corresponding position, and after mixing, 20 μL per well was transferred to the cell plate, and the final concentration of the compound transferred to the cell plate was 30 μmol to 13.7 nmol. The cell plate was placed in a carbon dioxide incubator and cultured for another 3 days.

1) Reading and analyzing data:

(1) CTG was added and the plate was read: 20 μL of CellTiter Glo was added to each well of the cell plate, and the cell plate was shaken in the dark for 10 min;

(2) plates were read on Victor Nivo.

Data Analysis:

The equation (Sample-Min)/(Max-Min)*100% was used to convert the original data into inhibition rate, and the $IC_{50}$ value could be obtained by curve fitting with four parameters (obtained by "log (inhibitor) vs. response—variable slope" mode in GraphPad Prism).

Experimental Results:

| Compound | Antiproliferative activity of HCT116 cells IC$_{50}$ (nM) |
| --- | --- |
| Compound 1 | 102.6 |
| Compound 3 | 138 |
| Compound 9 | 105 |
| Compound 11 | 123 |
| Compound 12 | 112 |
| Compound 13 | 138 |

Experimental conclusion: The compound of the present disclosure has good antiproliferative activity of HCT116 cells.

Experimental Embodiment 3: A375 (BRAF$^{V600E}$) Antiproliferative Activity Experiment Experimental Materials:
Cell line A375 (purchased from Procell). DMEM culture medium, penicillin/streptomycin antibiotics were purchased from Vicente, and fetal bovine serum was purchased from Biosera. CellTiter-glo (cell viability chemiluminescence detection reagent) reagent was purchased from Promega.

Experimental Steps:
A375 cells were seeded in a white 96 well plate with 80 μmol of cell suspension per well containing 2000 of A375 cells. The cell plate was placed in a carbon dioxide incubator and cultured overnight. The compound to be tested was diluted 3-fold to the 9th concentration with a pipette, that is, diluted from 6 mmol to 0.91 μmol, and a double-duplicate experiment was set-up, 78 μmol of culture medium was added to the middle plate, then 2 μmol of gradient dilution compound per well was transferred to the middle plate according to the corresponding position, and 20 μmol per well was mixed and transferred to the cell plate. The concentration of the compound transferred to the cell plate ranged from 30 μmol to 4.57 nmol. The cell plate was placed in a carbon dioxide incubator and cultured for 5 days. Another cell plate was prepared, and the signal value was read as the maximum value (max value in the following equation) on the day of administration to participate in data analysis, 25 μmol of cell viability chemiluminescence detection reagent was added to each well of the cell plate and incubated at room temperature for 10 minutes to stabilize the luminescence signal. A multi-marker analyzer reading was used. After the incubation of the cell plate added with the compound was finished, 25 μmol of cell viability chemiluminescence detection reagent was added to each well of the cell plate and incubated at room temperature for 10 minutes to stabilize the luminescence signal. A multi-marker analyzer reading was used.

Data Analysis:
The equation (Sample−Min)/(Max−Min)*100% was used to convert the original data into inhibition rate, and the IC$_{50}$ value could be obtained by curve fitting with four parameters (obtained by "log (inhibitor) vs. response—variable slope" mode in GraphPad Prism).

Experimental Results:

| Compound | Antiproliferative activity of A375 cells IC$_{50}$ (nM) |
| --- | --- |
| Compound 1 | 15 |
| Compound 3 | 13 |
| Compound 9 | 14 |
| Compound 11 | 16 |
| Compound 12 | 16 |
| Compound 13 | 17 |

Experimental conclusion: The compound of the present disclosure has good antiproliferative activity of A375 cells.

Experimental Embodiment 4: Colo205 (BRAF$^{V600E}$) Antiproliferative Activity Experiment Experimental Materials:
Cell line COLO205 (purchased from Procell), RPMI1640 culture medium, penicillin/streptomycin antibiotics were purchased from Vicente, and fetal bovine serum was purchased from Biosera. CellTiter-glo (cell viability chemiluminescence detection reagent) reagent was purchased from Promega.

Experimental Method:
Antiproliferative Experiment of COLO205 Cells:
COLO205 cells were seeded in a white 96-well plate with 80 μmol of cell suspension per well containing 3000 of COLO205 cells. The cell plate was placed in a carbon dioxide incubator and cultured overnight. The compound to be tested was diluted 3-fold to the 9th concentration with a pipette, that is, diluted from 200 μmol to 0.03 μmol, and a double-duplicate experiment was set-up. 78 μmol of culture medium was added to the middle plate, then 2 μmol of gradient dilution compound per well was transferred to the middle plate according to the corresponding position, and 20 μmol of per well was mixed and transferred to the cell plate. The concentration of the compound transferred to the cell plate ranged from 1 μmol to 0.15 nmol. The cell plate was placed in a carbon dioxide incubator and cultured for 3 days. Another cell plate was prepared, and the signal value was read as the maximum value (max value in the following equation) on the day of administration to participate in data analysis. 25 μmol of cell viability chemiluminescence detection reagent was added to each well of the cell plate and incubated at room temperature for 10 minutes to stabilize the luminescence signal. A multi-marker analyzer reading was used. After the incubation of the cell plate added with the compound was finished, 25 μmol of cell viability chemiluminescence detection reagent was added to each well of the cell plate and incubated at room temperature for 10 minutes to stabilize the luminescence signal. A multi-marker analyzer reading was used.

Data Analysis:
The equation (Sample−Min)/(Max−Min)*100% was used to convert the original data into inhibition rate, and the IC$_{50}$ value could be obtained by curve fitting with four parameters (obtained by "log (inhibitor) vs. response—variable slope" mode in GraphPad Prism).

Experimental Results:

| Compound | Antiproliferative activity of Colo205 cells IC$_{50}$ (nM) |
| --- | --- |
| Compound 3 | 16 |
| Compound 9 | 14 |
| Compound 11 | 16 |

| Compound | Antiproliferative activity of Colo205 cells IC$_{50}$ (nM) |
|---|---|
| Compound 12 | 21 |
| Compound 13 | 21 |

Experimental conclusion: The compound of the present disclosure has good antiproliferative activity of Colo205 cells.

Experimental Embodiment 5: Calu-6 (Kras$^{Q61K}$) ERK Phosphorylation Inhibition Experiment Experimental Materials:
Reagents and Consumables:

| Reagent | Brand number | Batch number |
|---|---|---|
| Human ERK phosphorylated protein highly sensitive detection kit | Cisbio-64AERPEH | 11B |
| RPMI1640 culture medium | Gibco-22400089 | 2025384 |
| Fetal bovine serum | Hyclone-SV30087.03 | RB35950 |
| 96 HTRF microplates | Cisbio-66PL96025 | No 03 |
| 96 Microplates | COSTAR-3599 | NA |
| DMSO | Sigma-D2650-100 mL | RNBG4295 |
| 0.05% Trypsin-EDTA | Gibco-25300-062 | 1897369 |

Main Instruments:

| Instrument | Manufacturer | Model |
|---|---|---|
| Biosafety cabinet | AIRTECH | BSC-1304IIA2 |
| Carbon dioxide incubator | Thermo | 311 |
| Cell counter | BECKMAN | Vi-cellXR |
| Microplate reader | PerkinElmer | Envision |
| Centrifuge | Eppendorf | Centrifuge 5810R |

Compound information (other compounds were derived from the mother liquid of the compound configured with L1000)
Cell Information:

| Cell name | Culture conditions | Source | Article number |
|---|---|---|---|
| Calu6 | 1640 + 10% FBS | ATCC | ATCC-HTB-56 |

Experimental Steps and Methods:
1) the cells were resuscitated and cultured to logarithmic growth phase, digested with trypsin, seeded in 96-well plates with 30000 cells per well, and incubated overnight in an incubator.
2) 1 μL of gradient compound dissolved with DMSO was added to a 96-well plate and placed back into an incubator to incubate for 1 hour.
3) The cell plates were removed out, and the culture medium was poured off, and 50 μL of cell lysate (with 1% blocking peptide) was added to each well.
4) The lysate plate was mixed at 500 rpm and incubated and lysed at room temperature for 30 minutes.
5) The antibody mixture in the kit was prepared at a ratio of 1:1:38.
6) 16 μL of cell lysate was transferred to the HTRF plate per well, then the 4 μL of the configured antibody mixture was added thereto.
7) After incubation overnight, the plate was read with Envision, and the fitted curve was obtained according to the ratio (the ratio of fluorescence intensity of Ex665/Ex615) and the EC$_{50}$ was calculated according to the four-parameter fitting formula Y=Bottom+(Top−Bottom)/(1+10^((Log EC$_{50}$−X)*HillSlope)) of Graphpad.

Experimental Results:

| Compound | Calu-6 ERK phosphorylation inhibition activity IC$_{50}$ (nM) |
|---|---|
| Compound 1 | 5.879 |
| Compound 2 | 13.08 |
| Compound 3 | 3.98 |
| Compound 4 | 6.36 |
| Compound 5 | 6.92 |
| Compound 7 | 4.39 |
| Compound 9 | 3.99 |
| Compound 10 | 3.03 |
| Compound 11 | 6.51 |
| Compound 12 | 6.91 |
| Compound 13 | 7.84 |

Experimental conclusion: The compound of the present disclosure has good Calu-6 ERK phosphorylation inhibition activity.

Experimental Embodiment 6: Pharmacokinetics Study of Single Intravenous and Oral Administration in Mice and Dogs Experimental Purpose:

This experiment was aimed to study the pharmacokinetics of the test compound in mice and dogs in vivo after a single oral administration of the compound.

Sample Collection and Preparation:

After intravenous or oral administration, blood samples were collected and the actual blood collection time was recorded. After the blood sample was collected, the sample was immediately transferred to a labeled centrifuge tube containing K2-EDTA, and then the plasma was taken after centrifugation. The plasma was transferred to a precooled centrifuge tube, quickly frozen in dry ice, and stored in an ultra-low temperature refrigerator at −70±10° C. until LC-MS/MS analysis.

Pharmacokinetic Data Analysis:

Pharmacokinetic software was used to process the plasma drug concentration data of the compound with non-atrioventricular model. The peak concentration (C$_{max}$) and peak time (T$_{max}$), as well as the end time of quantification, were obtained directly from the plasma drug concentration-time graph. The following pharmacokinetic parameters were calculated by logarithmic linear trapezoidal method: half-life (T$_{1/2}$), apparent distribution volume (V$_{dss}$) and clearance rate (Cl), and the area under the time-plasma concentration curve from 0 to the end time point (AUC$_{0-last}$).

1. Pharmacokinetic Data of Single Intravenous and Oral Administration in Mice

Pharmacokinetic Parameters of the Compound of the Present Disclosure after Single Intravenous Administration in Mice

| Compound number | Dosage (mg/kg/day) | Clearance rate Cl (ml/kg/min) | Apparent distribution volume $V_{dss}$ (L/kg) | Exposure $AUC_{0\text{-}last}$ (nmol · hour) | Half-life ($T_{1/2}$) (hour) |
|---|---|---|---|---|---|
| 1 | 0.5 | 10.3 | 0.4 | 1320 | 1.16 |
| 3 | 0.5 | 19.0 | 0.656 | 695 | 2.18 |
| 9 | 0.5 | 7.03 | 0.297 | 1957 | 1.26 |
| 11 | 0.5 | 13.8 | 0.422 | 944 | 1.17 |

Pharmacokinetic Parameters of the Compound of the Present Disclosure after Single Oral Administration in Mice

| Compound number | Dosage (mg/kg/day) | Maximum plasma drug concentration $C_{max}$ (nmol/L) | Peak time $T_{max}$ (h) | Exposure ($AUC_{0\text{-}last}$) (nmol · hour) |
|---|---|---|---|---|
| 1 | 50 | 73437 | 1 | 197287 |
| 3 | 50 | 156000 | 1 | 310913 |
| 4 | 50 | 181500 | 1 | 433603 |
| 5 | 50 | 90500 | 0.75 | 223560 |
| 9 | 50 | 124000 | 1.5 | 514818 |
| 10 | 50 | 34550 | 1.0 | 57799 |
| 11 | 50 | 157000 | 0.75 | 405618 |

Experimental conclusion: The compound of the present disclosure has good oral absorption and high exposure in mice.

2. Pharmacokinetic Data of Single Intravenous and Oral Administration in Dogs

Pharmacokinetic Parameters of the Compound of the Present Disclosure after Single Intravenous and Oral Administration in Dogs

| | PK parameters in dog | Compound 3 |
|---|---|---|
| Intravenous injection | Dosage (mg/kg/day) | 2 |
| | Clearance rate (mL/kg/min) | 1.34 |
| | Apparent distribution volume (L/kg) | 0.112 |
| | Exposure AUC (nmol · hour) | 37698 |
| | Half-life ($T_{1/2}$) (hour) | 4.3 |
| Oral | Dosage (mg/kg/day) | 10 |
| | Maximum plasma drug concentration (nmol/L) | 26700 |
| | Peak time (hour) | 3.00 |
| | Exposure $AUC_{0\text{-}last}$ (nmol · hour): | 112684 |
| | Oral bioavailability (%) | 59.8 |

Experimental conclusion: The compound of the present disclosure has good oral absorption, low clearance rate, high exposure and has good bioavailability in dogs.

Experimental Embodiment 7: In Vivo Pharmacodynamic Experiment of the BALB/c Nude Mouse Model of Subcutaneous Xenograft Tumors of Human Lung Cancer Calu-6 Cells Experimental Materials:

1.1 Experimental animals and feeding environment 1.1.1 Experimental animals

Species: mice

Strain: BALB/c nude mice

Age of arrival: 6 to 8 weeks old

Gender: female 1.1.2 Feeding Environment

Animals were kept in IVC (independent air supply system, constant temperature and humidity) cages in SPF grade animal rooms (3 to 5 per cage).

Temperature: 20 to 26° C.

Humidity: 40 to 70%

1.2 Tumor Tissue or Cell Information

Cells: Calu-6 cells of human lung cancer were cultured in vitro, and 0.2 Units/mL bovine insulin, 10% fetal bovine serum were added to EMEM culture medium in a 37° C. and 5% $CO_2$ incubator for culture. Conventional digestion with trypsin-EDTA was performed twice a week for passage. When the cell saturation was 80%-90% and the number of the cells reached the requirement, and the cells were collected, counted, and seeded.

1.3 Other Reagent Information

| Name | Manufacturer | Article number | Save condition |
|---|---|---|---|
| Fetal bovine serum | Hyclone | SV30087.03 | −20° C. |
| Trypsin | Gibco | 25200-072 | −20° C. |
| EMEM culture medium | ATCC | ATCC30-2003 | 2-8° C. |

1.4 Instrument Information

| Name | Manufacturer | Model |
|---|---|---|
| Carbon dioxide incubator | Thermo Fisher | Heracell240i |
| Low-temperature, high-speed centrifuge | Eppendorf | 5810R |
| Analytical balance | Sartorius | SECURA225D-1CN |
| Ordinary balance | Changzhou Tianzhiping Instruments Co., LTD | EL-2KJ |
| Digital vernier caliper | Mitutoyo | 0-150 mm |

Experimental Methods and Steps:

2.1 Tumor Cell Inoculation

Cell inoculation: 0.2 mL of Calu-6 cell (mixed in a ratio of 1:1 with matrix gel) was subcutaneously inoculated on the right back of each mouse, and group administration was started when the average tumor volume reached 173 mm,

2.2 Grouping

TABLE 1

Experimental animal grouping and administration regimen

| Group | N[1] | Compound treatment | Dosage (mg/kg) | volume parameters (μL/g)[2] | Route of administration | Administration frequency |
|---|---|---|---|---|---|---|
| 1 | 6 | Solvent control group [3] | — | 10 | Oral (PO) | Once a day (QD) |
| 2 | 6 | Compound 1 | 50 | 10 | Oral (PO) | Once a day (QD) |
| 3 | 6 | Compound 3 | 50 | 10 | Oral (PO) | Once a day (QD) |
| 4 | 6 | Compound 4 | 50 | 10 | Oral (PO) | Once a day (QD) |
| 5 | 6 | Compound 9 | 50 | 10 | Oral (PO) | Once a day (QD) |
| 6 | 6 | Compound 11 | 50 | 10 | Oral (PO) | Once a day (QD) |

Note:
[1] number of mice in each group;
[2] administration volume parameters: 10 μL/g according to mouse body weight. If body weight loss exceeded more than 15%, the administration was stopped until body weight was back to within 10%;
[3] 0.5% MC (methylcellulose).

Note: 1: number of mice in each group; 2: administration volume parameters: 10 μL/g according to mouse body weight. If body weight loss exceeded more than 15%, the administration was stopped until body weight was back to within 10%: 3:0.5% MC (methylcellulose).

2.3 Tumor Measurement and Experimental Indicators

Tumor diameters were measured with vernier calipers twice a week. The calculation formula of tumor volume was: $V = 0.5 a \times b^2$, and a and b represent the long and short diameters of the tumor, respectively.

The tumor inhibition efficacy of the compounds was evaluated by TGI (%) or relative tumor proliferation rate T/C (%). Relative tumor proliferation rate T/C (%)=$T_{RTV}/C_{RTV} \times 100\%$ ($T_{RTV}$: RTV in the treatment group; $C_{RTV}$: RTV in the negative control group). The relative tumor volume (RTV) was calculated according to the results of tumor measurement, and the formula was RTV=$V_t/V_0$, wherein $V_0$ was the tumor volume measured at the time of group administration (i.e., $D_0$), and $V_t$ was the tumor volume measured at a certain measurement, and $T_{RTV}$ and $C_{RTV}$ were taken on the same day.

TGI (%), reflecting the tumor growth inhibition rate. TGI (%)=[1−(average tumor volume at the end of administration in a treatment group−average tumor volume at the beginning of administration in this treatment group)/(average tumor volume at the end of treatment in a solvent control group−average tumor volume at the beginning of treatment in this solvent control group)]×100%.

2.5 Statistical Analysis

Statistical analysis was based on the data of RTV at the end of the experiment, and SPSS software was used for analysis. One-way ANOVA was used for comparison between two groups, and the variance was uneven (there was significant difference in F value), and Games-Howell method was used to test, p<0.05 was considered a significant difference.

3. Experimental Results

3.1 Inhibition Efficacy of Subjects on Subcutaneous Tumor Growth in Nude Mice with Human Lung Cancer This experiment evaluated the efficacy of the subject in human lung cancer xenograft tumor model, using solvent control group as a reference. The TGI of the administration group compound 1 was 107%, the TGI of the compound 3 was 110%, the TGI of the compound 9 was 108% and the TGI of the compound 11 was 109%, which showed a significant tumor suppressor effect (P<0.01).

3.2 Weight Change

Figure 2:
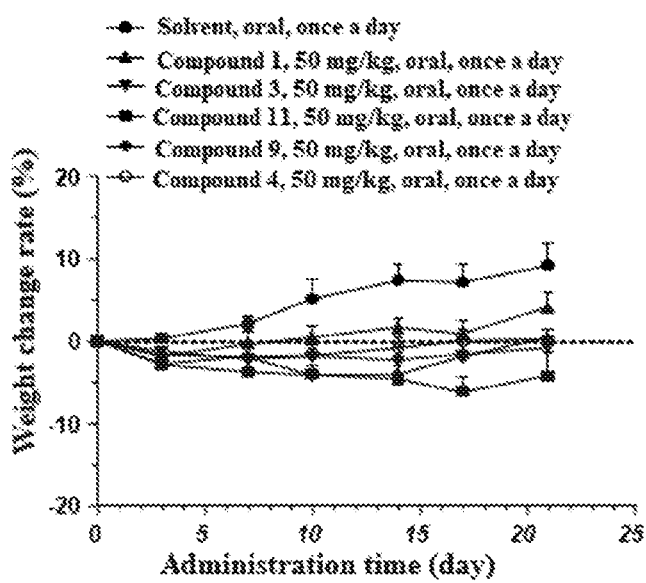
FIG. 2: the effect of subjects on the weight of the mice.

There was no obvious abnormality in the weight and state of the mice. The effect of the subject on the body weight of the mice is as shown in FIG. 2.

Experimental Conclusion:

The compound of the present disclosure has a significant inhibition effect on the growth of human lung cancer Calu-6 cell subcutaneous xenograft tumor model tumor-bearing mice.

The invention claimed is:

1. A compound represented by formula (II) or a pharmaceutically acceptable salt thereof,

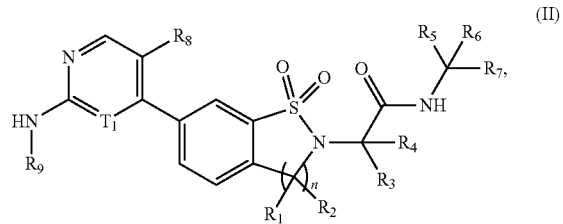

wherein, $T_1$ is CH or N;

n is 1 or 2;

$R_1$ and $R_2$ are each independently H, D, F, Cl or $C_{1-3}$ alkyl, wherein the $C_{1-3}$ alkyl is optionally substituted by 1, 2 or 3 substituents independently selected from F, Cl, Br and I;

or $R_1$ and $R_2$ combining with the carbon atoms to which they are attached form

$R_3$ and $R_4$ are each independently H or $C_{1-3}$ alkyl, wherein the $C_{1-3}$ alkyl is optionally substituted by 1, 2 or 3 substituents independently selected from F, Cl, Br, I and —OH;

$R_5$ and $P_6$ are each independently H or $C_{1-3}$ alkyl, wherein the $C_{1-3}$ alkyl is optionally substituted by 1, 2 or 3 substituents independently selected from F, Cl, Br, I, —OH and —OCH$_3$;

R₇ is phenyl or pyridyl, wherein the phenyl and pyridyl are optionally substituted by 1, 2, 3 or 4 R_a;

R₈ is H, F, Cl or Br;

R₉ is tetrahydro-2H-pyranyl, wherein the tetrahydro-2H-pyranyl is optionally substituted by 1, 2, 3 or 4 R_b;

R_a is each independently F, Cl, Br, I, C₁₋₃ alkyl, C₁₋₃ alkoxy, NH—C₁₋₃ alkyl or N—(C₁₋₃ alkyl)₂, wherein the C₁₋₃ alkyl, C₁₋₃ alkoxy, —NH—C₁₋₃ alkyl and —N—(C₁₋₃ alkyl)₂ are each independently and optionally substituted by 1, 2 or 3 substituents independently selected from F, Cl, Br, I and —OH;

R_b is each independently F, Cl, Br, I, D or C₁₋₃ alkyl, wherein the C₁₋₃ alkyl is optionally substituted by 1, 2 or 3 substituents independently selected from F, Cl, Br, I and —OH.

2. The compound or the pharmaceutically acceptable salt thereof as claimed in claim 1, wherein the compound has the structure represented by formula (I-1), (I-2) or (II-1):

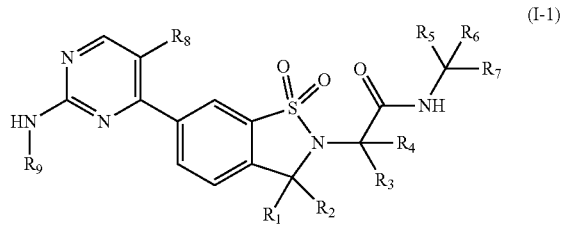
(I-1)

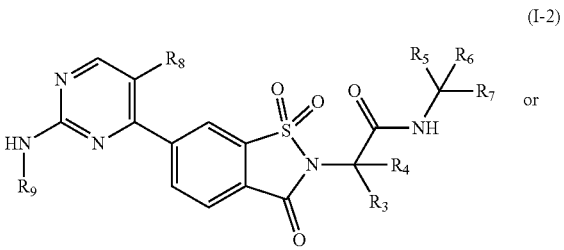
(I-2)

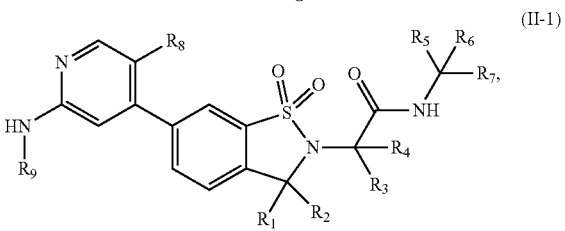
(II-1)

wherein, R₁, R₂, R₃, R₄, R₅, R₆, R₇, R₈ and R₉ are as defined above.

3. The compound or the pharmaceutically acceptable salt thereof as claimed in claim 1, wherein the R_b is each independently F, Cl, Br, I, D or —CH₃.

4. The compound or the pharmaceutically acceptable salt thereof as claimed in claim 1, wherein the R₉ is

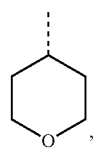, wherein the

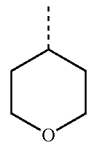

is optionally substituted by 1, 2, 3 or 4 R_b.

5. The compound or the pharmaceutically acceptable salt thereof as claimed in claim 4, wherein the R₉ is

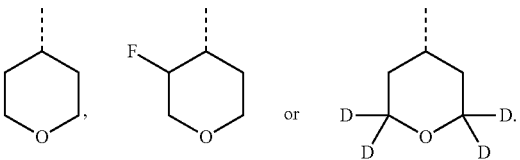

6. The compound or the pharmaceutically acceptable salt thereof as claimed in claim 1, wherein the compound has the structure represented by formula III-1) or (III-2):

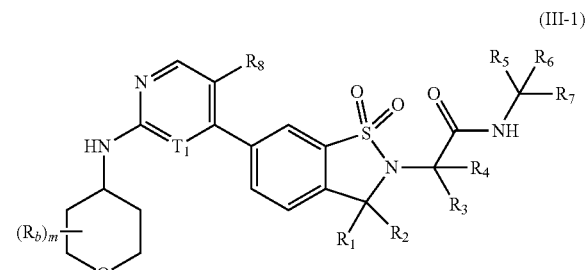
(III-1)

or

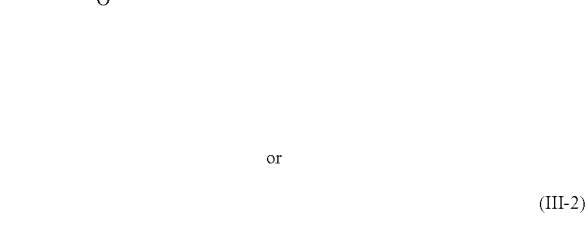
(III-2)

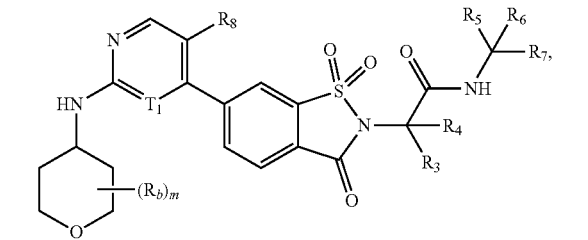

wherein, m is 0, 1, 2, 3 or 4;

T₁, R_b, R₁, R₂, R₃, R₄, R₅, R₆, R₇ and R₈ are as defined above.

7. The compound or the pharmaceutically acceptable salt thereof as claimed in claim 6, wherein the compound has the structure represented by formula (I-3) or (I-4):

(I-3)

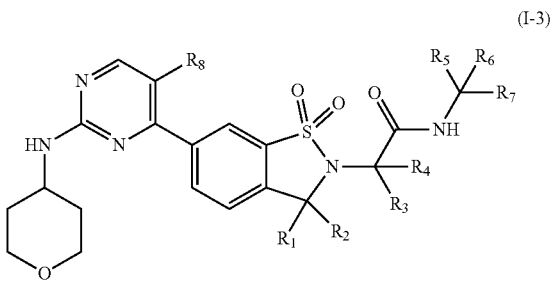

or (I-4)

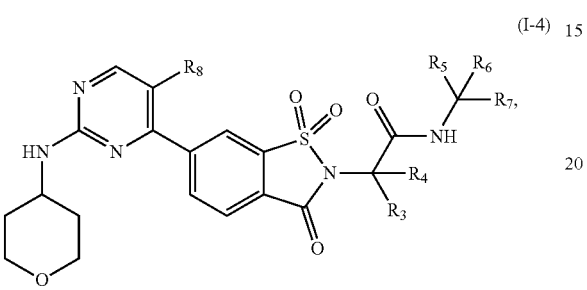

wherein, $R_1$, $R_2$, $R_3$, $R_4$, $R_5$, $R_6$, $R_7$ and $R_8$ are as defined above.

8. The compound or the pharmaceutically acceptable salt thereof as claimed in claim 1, wherein the $R_1$ and $R_2$ are each independently H, D, F, Cl or —$CH_3$.

9. The compound or the pharmaceutically acceptable salt thereof as claimed in claim 1, wherein, the $R_1$ and $R_2$ combining with the carbon atoms to which they are attached form

10. The compound or the pharmaceutically acceptable salt thereof as claimed in claim 1, wherein, the $R_3$ and $R_4$ are each independently H or —$CH_3$, wherein the —$CH_3$ is optionally substituted by 1, 2 or 3 substituents independently selected from F, Cl, Br, I and —OH.

11. The compound or the pharmaceutically acceptable salt thereof as claimed in claim 10, wherein the $R_3$ and $R_4$ are each independently H, —$CH_3$ or

12. The compound or the pharmaceutically acceptable salt thereof as claimed in claim 1, wherein, the $R_5$ and $R_6$ are each independently H or —$CH_3$, wherein the —$CH_3$ is optionally substituted by 1, 2 or 3 substituents independently selected from F, Cl, Br, I, —OH and —$OCH_3$.

13. The compound or the pharmaceutically acceptable salt thereof as claimed in claim 12, wherein the $R_5$ and $R_6$ are each independently H, —$CH_3$ or

14. The compound or the pharmaceutically acceptable salt thereof as claimed in claim 1, wherein the compound has the structure represented by formula III-3) or (III-4):

(III-3)

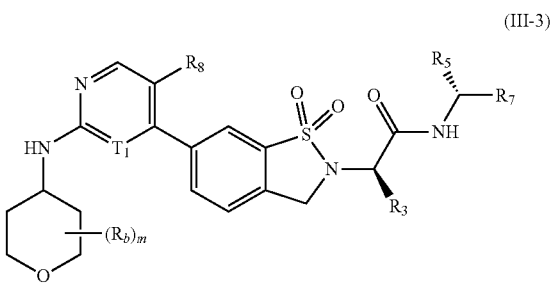

or (III-4)

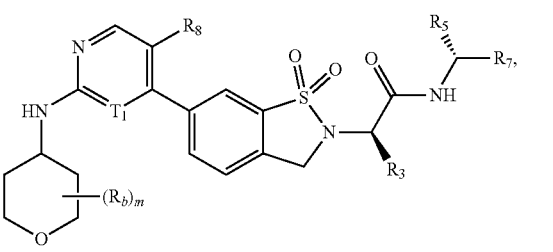

wherein, m is 0, 1, 2, 3 or 4;

$T_1$, $R_b$, $R_7$ and $R_8$ are as defined above;

$R_3$ is —$CH_3$, wherein the —$CH_3$ is optionally substituted by 1, 2 or 3 substituents independently selected from F, Cl, Br, I and —OH;

$R_5$ is —$CH_3$, wherein the —$CH_3$ is optionally substituted by 1, 2 or 3 substituents independently selected from F, Cl, Br, I, —OH and —$OCH_3$.

15. The compound or the pharmaceutically acceptable salt thereof as claimed in claim 1, wherein the compound has the structure represented by formula (I-5) or (I-6):

(I-5)

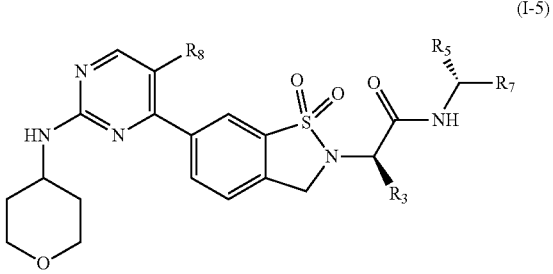

or (I-6)

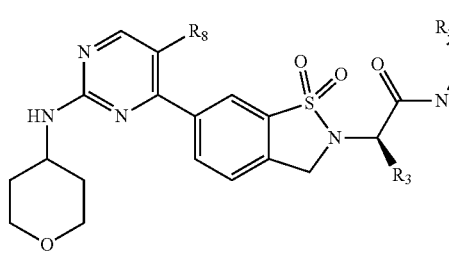

wherein, R_7 and R_3 are as defined in above;

R_3 is —CH_3, wherein the —CH_3 is optionally substituted by 1, 2 or 3 substituents independently selected from F, Cl, Br, I and —OH;

R_5 is —CH_3, wherein the —CH_3 is optionally substituted by 1, 2 or 3 substituents independently selected from F, Cl, Br, I, —OH and —OCH_3.

16. The compound or the pharmaceutically acceptable salt thereof as claimed in claim 1, wherein the R_a is each independently F, C, Br, I, —CH_3, —OCH_3, —NH—CH_3 or

17. The compound or the pharmaceutically acceptable salt thereof as claimed in claim 1, wherein the R_7 is

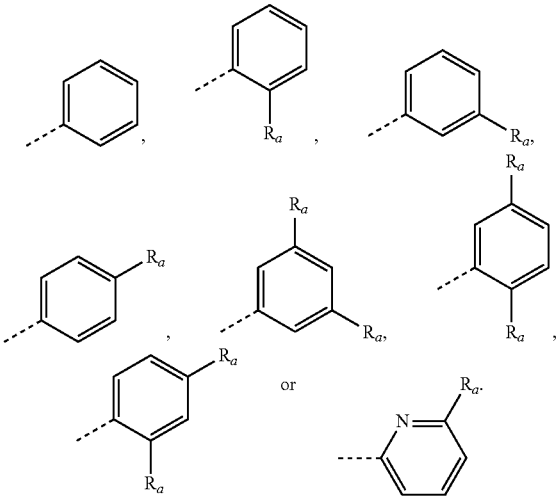

18. The compound or the pharmaceutically acceptable salt thereof as claimed in claim 17, wherein the R_7 is

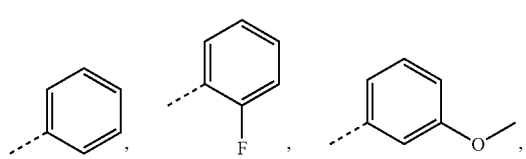

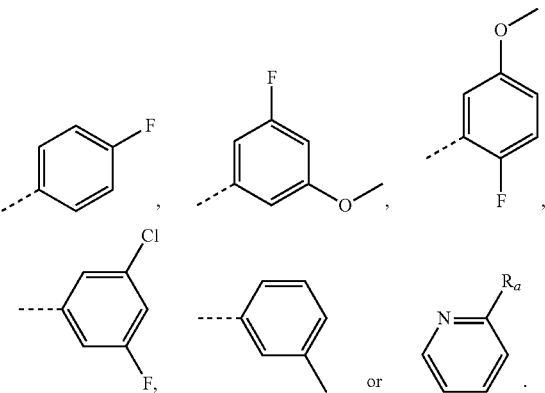

19. A compound represented by the following formula or a pharmaceutically acceptable salt thereof, and the compound is:

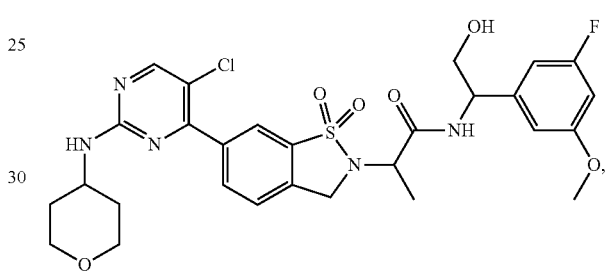

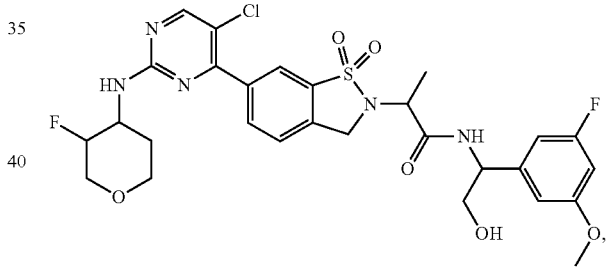

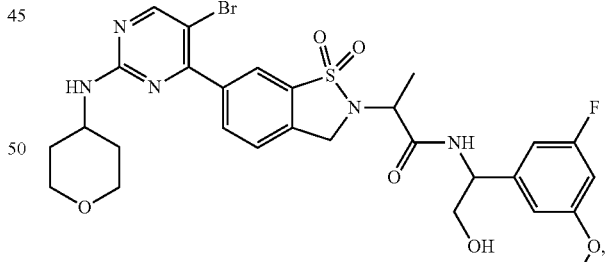

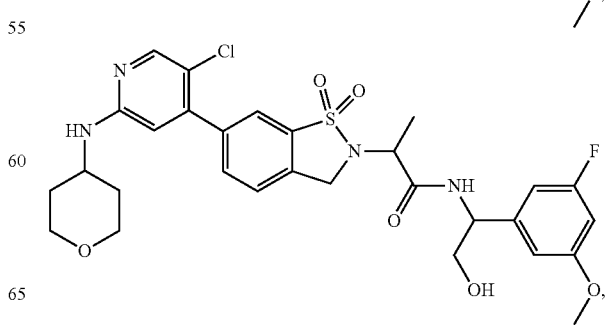

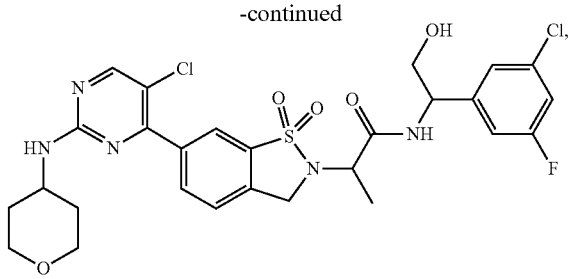
,
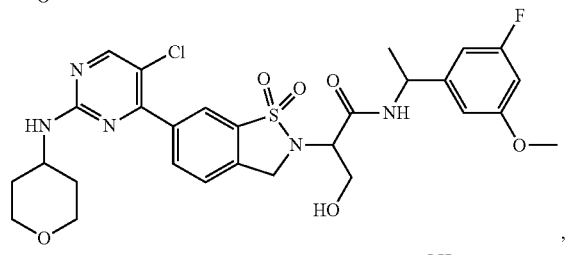
,
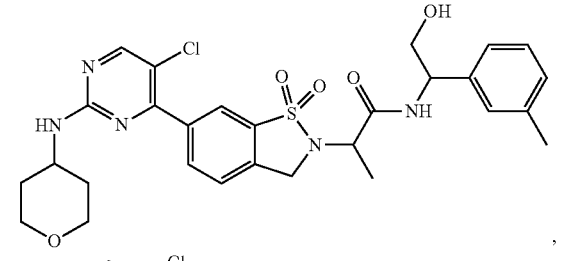
,
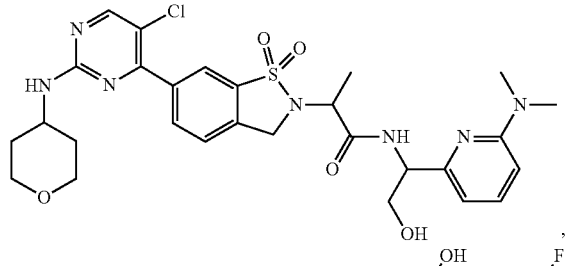
,
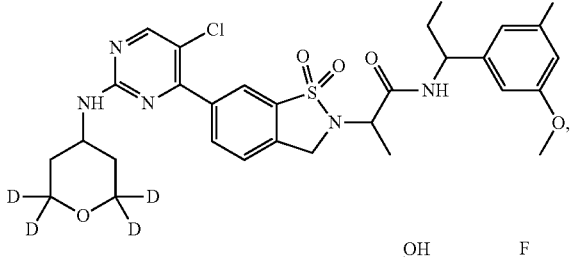
,
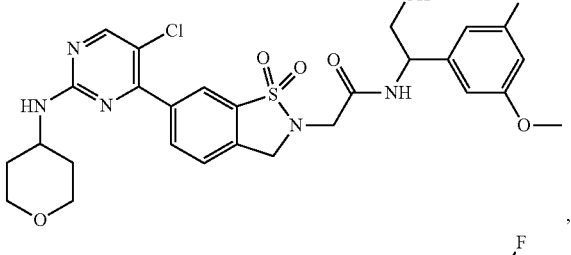
,
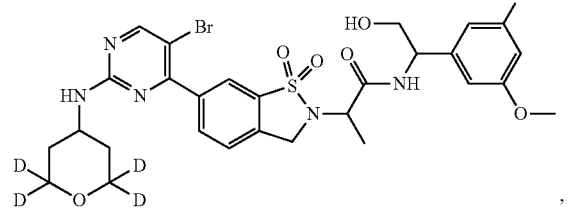
,
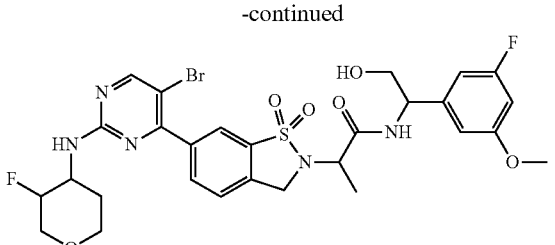
or
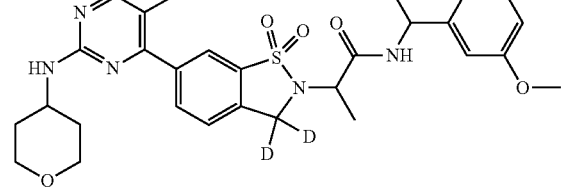
.
20. A compound represented by the following formula or a pharmaceutically acceptable salt thereof, and the compound is:
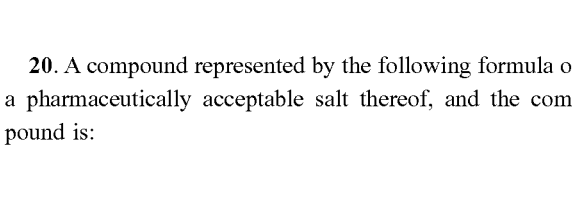
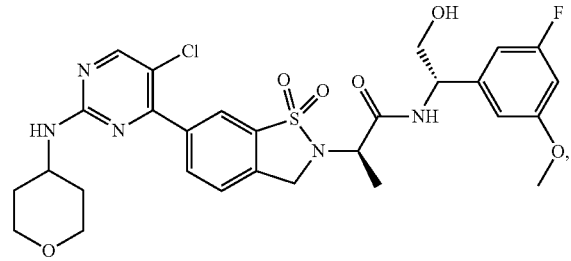
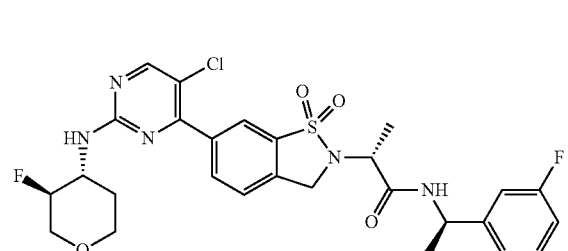

93
-continued
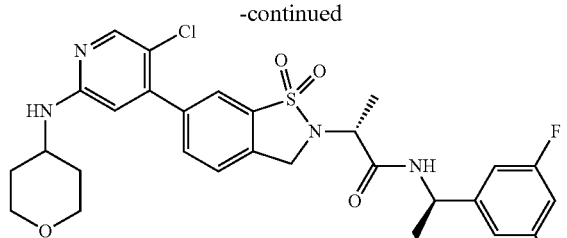
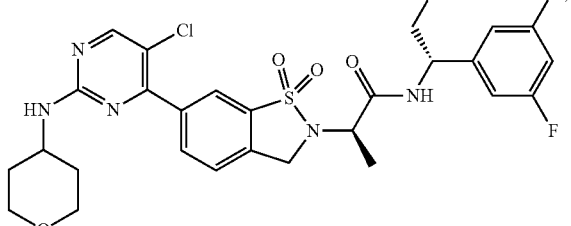
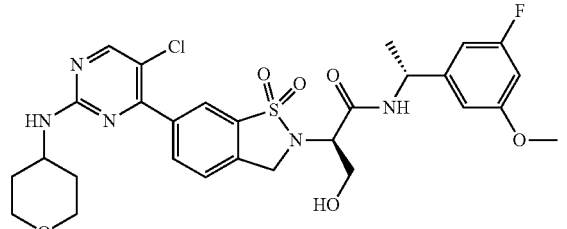
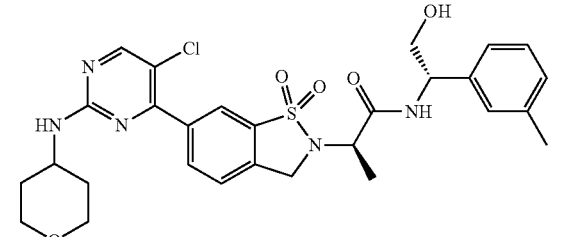
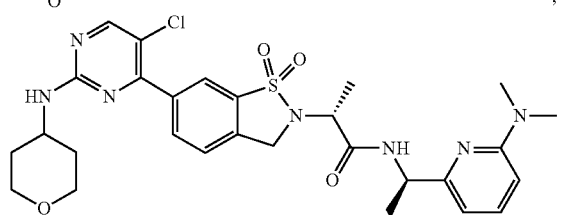
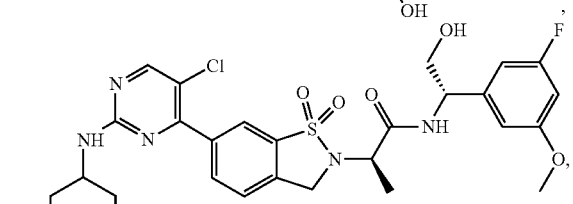
94
-continued
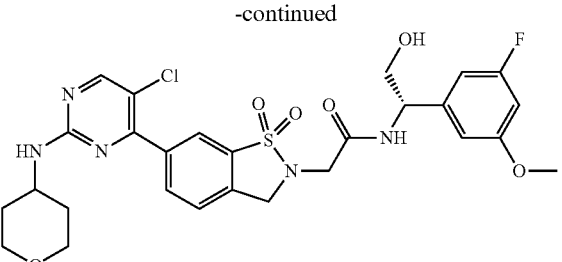
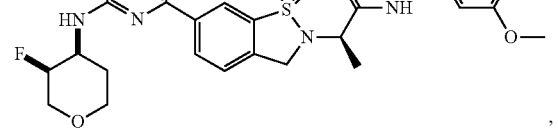
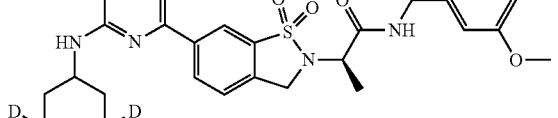
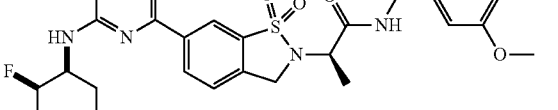
or
* * * * *